US008189901B2

(12) United States Patent
Modiano et al.

(10) Patent No.: US 8,189,901 B2
(45) Date of Patent: May 29, 2012

(54) SEED SORTER

(75) Inventors: Steven H. Modiano, Manchester, MO (US); Kevin L. Deppermann, St. Charles, MO (US); James Crain, Wildwood, MO (US); Sam R Eathington, Ames, IA (US); Mike Graham, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 955 days.

(21) Appl. No.: 12/129,444

(22) Filed: May 29, 2008

(65) Prior Publication Data

US 2008/0310674 A1 Dec. 18, 2008

Related U.S. Application Data

(60) Provisional application No. 60/941,155, filed on May 31, 2007.

(51) Int. Cl.
*G06K 9/00* (2006.01)

(52) U.S. Cl. ...... 382/141; 47/14; 47/58.1 R; 250/339.07; 250/339.12; 382/100; 382/108; 382/286; 382/191

(58) Field of Classification Search ............ 250/339.07–339.12; 382/100, 382/108–110, 286, 141, 191, 165; 47/14, 47/58.1 R See application file for complete search history.

(56) References Cited

U.S. PATENT DOCUMENTS

| 2,756,903 A | 6/1952 | Kreidler |
| 3,530,372 A | 9/1970 | Laukien |
| 3,642,128 A | 2/1972 | Westwood et al. |
| 3,861,788 A | 1/1975 | Webster |
| 4,037,970 A | 7/1977 | Webster et al. |
| 4,040,747 A | 8/1977 | Webster |
| 4,251,011 A | 2/1981 | Hamilton et al. |

(Continued)

FOREIGN PATENT DOCUMENTS

CL 3138-2000 9/2001

(Continued)

OTHER PUBLICATIONS

"Seed Meister Luminar 3076," Brimrose Corporation of America, Baltimore, MD, http://www.brimrose.com/seed_meister.html.

(Continued)

*Primary Examiner* — Gregory J Toatley
*Assistant Examiner* — Iyabo S Alli
(74) *Attorney, Agent, or Firm* — James E. Davis; Joseph A. Schaper; Harness, Dickey & Pierce, P.L.C.

(57) ABSTRACT

The present disclosure provides systems and methods for sorting seeds based on identified phenotypes of the seeds. In various embodiments, the system includes an optics and controller station structured and operable to collect image data of a top portion, a bottom portion and a plurality of side portions of each respective seed in a set of seeds, and to analyze the collected image data to determine whether each seed exhibits a desired phenotype. The system further includes a seed loading, transporting and sorting station structured and operable to singulate each seed of the set of seeds from a plurality of seeds in a bulk seed hopper, transport the set of seeds to the optics and controller station, and selectively sort each seed to a respective one of a plurality of seed repositories based on whether each respective seed exhibits the desired phenotype.

38 Claims, 36 Drawing Sheets

U.S. PATENT DOCUMENTS

| | | | |
|---|---|---|---|
| 4,260,262 A | 4/1981 | Webster | |
| 4,375,854 A | 3/1983 | Hedel | |
| 4,401,236 A | 8/1983 | Germaine | |
| 4,480,765 A | 11/1984 | Tonus | |
| 4,654,592 A | 3/1987 | Zens | |
| 4,734,584 A | 3/1988 | Rosenthal | |
| 4,752,689 A | 6/1988 | Satake | |
| 4,818,380 A | 4/1989 | Azegami et al. | |
| 4,863,041 A * | 9/1989 | Bailey ................... 250/226 | |
| 4,884,696 A | 12/1989 | Peleg | |
| 4,931,061 A | 6/1990 | Young | |
| 4,946,046 A | 8/1990 | Affleck et al. | |
| 5,051,699 A | 9/1991 | Hanawa et al. | |
| 5,067,631 A | 11/1991 | Baba | |
| 5,132,538 A | 7/1992 | Norris | |
| 5,221,518 A | 6/1993 | Mills | |
| 5,245,188 A | 9/1993 | Satake et al. | |
| 5,253,302 A | 10/1993 | Massen | |
| 5,308,986 A | 5/1994 | Walker | |
| 5,321,212 A | 6/1994 | Wadell | |
| 5,412,220 A | 5/1995 | Moore | |
| 5,475,221 A | 12/1995 | Wang | |
| 5,533,145 A | 7/1996 | Shofner et al. | |
| 5,590,791 A | 1/1997 | Gschweitl | |
| 5,668,374 A | 9/1997 | DiFoggio et al. | |
| 5,669,511 A | 9/1997 | Satake et al. | |
| 5,733,592 A | 3/1998 | Wettstein et al. | |
| 5,751,421 A | 5/1998 | Wright et al. | |
| 5,764,819 A | 6/1998 | Orr et al. | |
| 5,833,947 A | 11/1998 | Rocklage et al. | |
| 5,836,438 A | 11/1998 | Jung | |
| 5,837,458 A | 11/1998 | Minshull et al. | |
| 5,864,984 A | 2/1999 | McNertney | |
| 5,918,977 A | 7/1999 | Borggaard et al. | |
| 5,991,025 A | 11/1999 | Wright et al. | |
| 6,098,838 A | 8/2000 | Saho et al. | |
| 6,100,526 A | 8/2000 | Mayes | |
| 6,150,158 A | 11/2000 | Bhide et al. | |
| 6,237,286 B1 | 5/2001 | Williams | |
| 6,266,864 B1 | 7/2001 | Barber | |
| 6,397,678 B1 | 6/2002 | Popper | |
| 6,537,826 B1 | 3/2003 | Horigane ................... 436/176 | |
| 6,640,428 B2 | 11/2003 | Barber | |
| 6,646,264 B1 * | 11/2003 | Modiano et al. ............ 356/326 | |
| 6,688,037 B2 | 2/2004 | Keller et al. | |
| 6,705,827 B2 | 3/2004 | Keller et al. | |
| 6,706,989 B2 | 3/2004 | Hunter et al. | |
| 6,782,991 B2 | 8/2004 | Johansson | |
| 6,809,819 B1 | 10/2004 | Vinjamoori et al. | |
| 6,879,389 B2 | 4/2005 | Meyer et al. | |
| 6,959,617 B2 | 11/2005 | Deppermann | |
| 7,044,306 B2 | 5/2006 | Deppermann | |
| 7,258,237 B2 | 8/2007 | Nielsen | |
| 7,367,155 B2 | 5/2008 | Kotyk et al. | |
| 7,483,137 B2 | 1/2009 | Janni | |
| 7,502,113 B2 | 3/2009 | Deppermann et al. | |
| 7,600,642 B2 | 10/2009 | Deppermann | |
| 7,685,768 B2 | 3/2010 | Deppermann | |
| 7,934,600 B2 | 5/2011 | Deppermann | |
| 8,028,469 B2 | 10/2011 | Deppermann et al. | |
| 2001/0013486 A1 | 8/2001 | Yamakawa | |
| 2001/0014750 A1 | 8/2001 | Ulrich et al. | |
| 2003/0142852 A1 | 7/2003 | Lu et al. | |
| 2004/0072143 A1 | 4/2004 | Timmis et al. | |
| 2004/0141641 A1 | 7/2004 | McDonald et al. | |
| 2004/0160607 A1 | 8/2004 | Lin et al. | |
| 2004/0221335 A1 | 11/2004 | Shewmaker et al. | |
| 2005/0082207 A1 | 4/2005 | Deppermann | |
| 2006/0042527 A1 | 3/2006 | Deppermann | |
| 2006/0042528 A1 | 3/2006 | Deppermann | |
| 2006/0046244 A1 | 3/2006 | Deppermann | |
| 2006/0112628 A1 | 6/2006 | Kotyk et al. | |
| 2007/0048872 A1 | 3/2007 | Deppermann et al. | |
| 2007/0204366 A1 | 8/2007 | Deppermann et al. | |
| 2007/0207485 A1 | 9/2007 | Deppermann et al. | |
| 2007/0240242 A1 | 10/2007 | Modiano et al. | |
| 2008/0000815 A1 | 1/2008 | Deppermann | |
| 2008/0113367 A1 | 5/2008 | Becker et al. | |
| 2008/0131254 A1 | 6/2008 | Cope et al. | |
| 2008/0131924 A1 | 6/2008 | Cope et al. | |
| 2008/0317279 A1 | 12/2008 | Deppermann et al. | |
| 2009/0032441 A1 | 2/2009 | Corak et al. | |

FOREIGN PATENT DOCUMENTS

| | | |
|---|---|---|
| CL | 673-03 | 2/2004 |
| CL | 2189-05 | 5/2007 |
| DE | 19845883 A1 | 5/1999 |
| DE | 102004063769 A1 | 7/2006 |
| EP | 0636310 A1 | 2/1995 |
| EP | 0730164 | 9/1996 |
| EP | 0750188 | 12/1996 |
| EP | 0511184 B1 | 6/1998 |
| EP | 0539537 B2 | 12/2000 |
| FR | 2549963 | 2/1985 |
| GB | 1355612 | 6/1974 |
| JP | 401156233 A | 6/1989 |
| JP | 406284806 A | 10/1994 |
| JP | 10319106 | 4/1998 |
| WO | WO 9624830 | 8/1996 |
| WO | WO 9700887 | 1/1997 |
| WO | WO 9844140 | 10/1998 |
| WO | WO 9940419 | 8/1999 |
| WO | WO 9941383 | 8/1999 |
| WO | WO 9958959 | 11/1999 |
| WO | WO 99/63057 | 12/1999 |
| WO | WO 0052990 | 9/2000 |
| WO | WO 0071993 A1 | 11/2000 |
| WO | WO-01/22043 | 3/2001 |
| WO | WO 01/22043 A2 | 3/2001 |
| WO | WO 0144828 A1 | 6/2001 |
| WO | WO 0189288 A1 | 11/2001 |
| WO | WO 0259586 | 1/2002 |
| WO | WO 0216090 A3 | 2/2002 |
| WO | WO 02/48687 | 6/2002 |
| WO | WO-02/071040 | 9/2002 |
| WO | WO-2006/026467 | 3/2006 |

OTHER PUBLICATIONS

Archibald et al., "Development of Short-Wavelength Near-Infrared Spectral Imaging for Grain Color Classification," SPIE vol. 3543, 1998, pp. 189-198.

Bauman, et al., Inheritance of Variation of Oil Content of Individual Corn Kernels, Crop Science, vol. 5, pp. 137-138, 1965.

Daun et al., "Comparison of Three Whole Seed Near-Infrared Analyzers for Measuring Quality Components of Canola Seed," vol. 71, No. 10, 1994, pp. 1063-1068.

Delwiche, "Single Sheat Kernel Analysis by Near-Infrared Transmittance: Protein Content," Analytical Techniques and Instrumentation, vol. 72, No. 1, 1995, pp. 11-16.

Dowell et al., "Automated Single Wheat Kernel Quality Measurement Using Near-Infrared Reflectance," ASAE Annual International Meeting, 1997, paper No. 973022.

Dowell, "Automated Color Classification of Single Wheat Kernels Using Visible and Near-Infrared Reflectance," Cereal Chemistry, vol. 75(1), 1998, pp. 142-144.

Dr. Jolanta Soos, "Industrial Process Monitoring Requires Rugged AOTF Tools," Laser Focus World, Aug. 1994.

Floyd E. Dowell, "An Intelligent Automated System for Determining Peanut Quality," IEEE International Workshop on Intelligent Robots and Systems, Jul. 1990.

Gambhir, et al., Simultaneous Determination of Moisture and Oil Content in Oilseeds by Pulsed Nuclear Magnetic Resonance, JOACS, vol. 62, No. 1, Jan. 1985.

Guy Rubel, "Simultaneous Determination of Oil and Water Contents in Different Oil Seeds by Pulsed Nuclear Magnetic Resonance," XP 001080188, JAOCS, vol. 71, No. 10, Oct. 1994.

J.M. Halloin et al., "Proton Magnetic Resonance Imaging of Llpd in Pecan Embryos", XP 001080187, Journal of the American Oil Chemists' Society, vol. 70, No. 12, Dec. 1993.

J.R. Heil, et al., "Magnetic Resonance Imaging and Modeling of WaterUp-take into Dry Beans", XP 002202044, Dept. of Food Science and Technology, University of California, Davis, CA, Jan. 23, 1992.

K. Saito, et al., "Application of Magnetic Resonance Imaging to Non-Destructive Boid Detection in Watermelon," XP 000656797, Cryogenics, vol. 36, No. 12, 1996.

M.R. Lakshiminarayana et al., "Spatial distribution of oil in groundnut and sunflower seeds by nuclear magnetic resonance imaging," XP 002201726, J. Biosci., vol. 17, No. 1, Mar. 1992, pp. 87-93.

MacNamara, et al., "Multiplex Sample NMR: an Approach to High-Throughput NMR Using a Parallel Coil Probe," Analytica Chimica Acta; vol. 397, No. 1/03; Elsevier Science B.V.; Oct. 1999, pp. 9-16.

Massie and Norris, "Spectral Reflectance and Transmittance Properties of Grain in the Visible and Near Infrared", Transactions of the ASAE, Winter Meeting of the American Society of Agricultural Engineers, 1965, pp. 598-600.

McEntyre, et al., Comparison of Water Absorption Patterns in Two Barley Cultivars, Using Magnetic Resonance Imaging, AACCI, Cereal Chemistry, vol. 76, No. 6, pp. 792-795, 1998.

McGinty, et al., A System for Automatic Weight Determination of Individual Grain Kernels: Principles and Evaluation, Cereal Science Today, vol. 19, No. 5, May 1974.

Orman and Schumann, "Comparison of Near-Infrared Spectroscopy Calibration Methods for the Prediction of Protein, Oil, and Starch in Maize Grain," J. Agric. Food Chem. vol. 39, 1991, pp. 883-886.

P.A. Hailey—Pfizer Central Research, "The Role of NIR Spectroscopy in the Measurement of Pharmaceutical Manufacture," http://www.brimrose.com/hailey.html; date unknown.

Paige, et al., "Apparatus for Automatic Measurement of Kernel Weight, Length, and Thickness," Crop Science, vol. 31, pp. 1314-1318, 1991.

Robutti, "Maize Kernel Hardness Estimation in Breeding by Near-Infrared Transmission Analysis," Analytical Techniques and Instrumentation vol. 72, No. 6, 1995, pp. 632-636.

Sander, et al., System for Automatic Weight Determination of Individual Grain Kernels, Transactions of the American Society Agricultural Engineers, vol. 16, No. 6, pp. 1146-1147, Nov./Dec. 1973.

Siebenmorgen, et al., A Data Acquisition/Control System for Individual Kernel and Thin-Layer Grain Drying Research, The American Society of Agricultural Engineers, No. 91-3042, Jun. 1991.

Song et al., Non-invasive Measurement of Moisture Distribution in Individual Wheat Kernels by Magnetic Resonance Imaging, SPIE vol. 2345, Nov. 2-4, 1994.

Yoshida, et al., "An Automatic Sequential Single-Seed Weighing System: Variation in Soybean Seed Weight," Journal of the Faculty of Agriculture, Hokkaido University, vol. 61, Pt. 2, 1983.

* cited by examiner

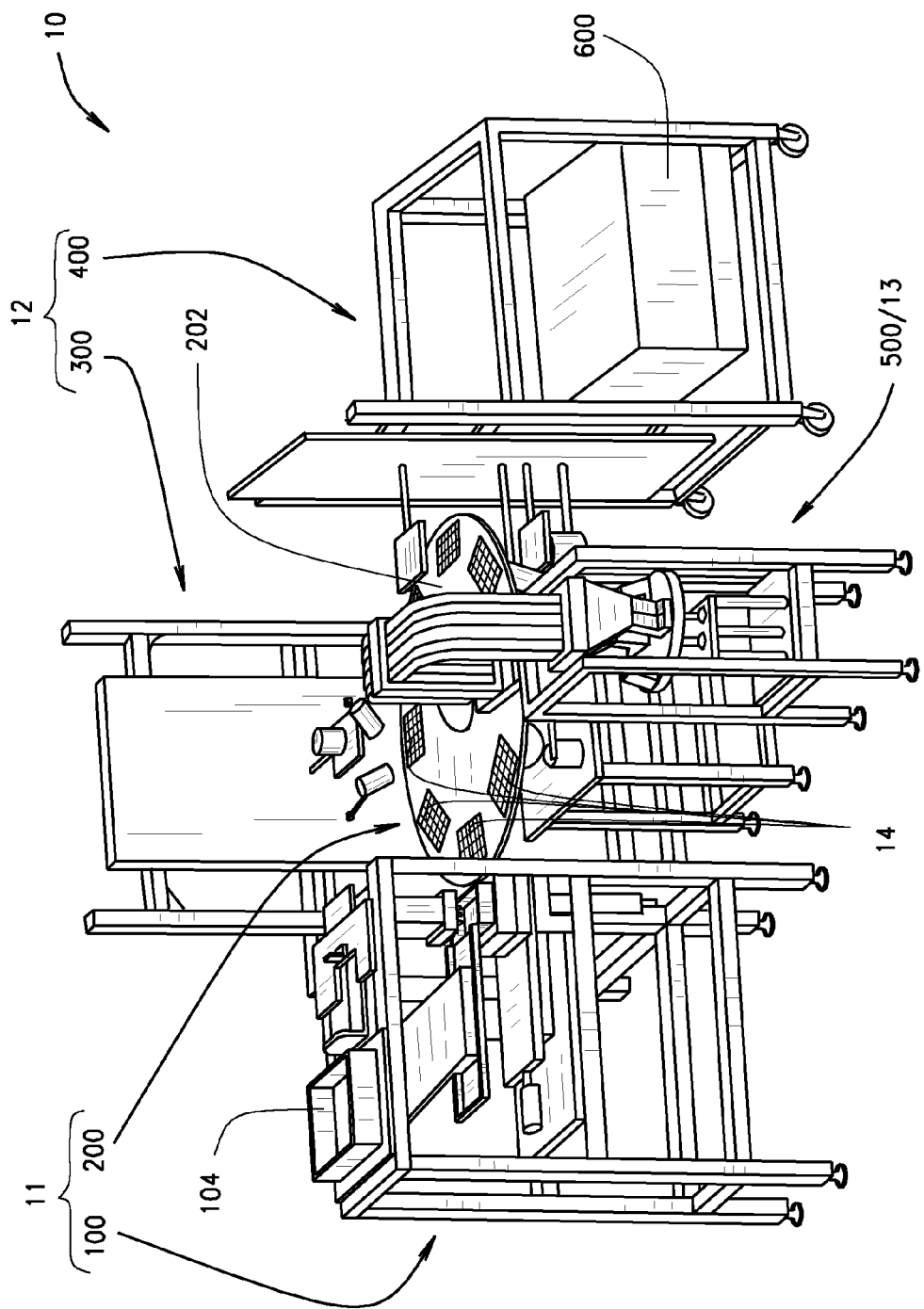

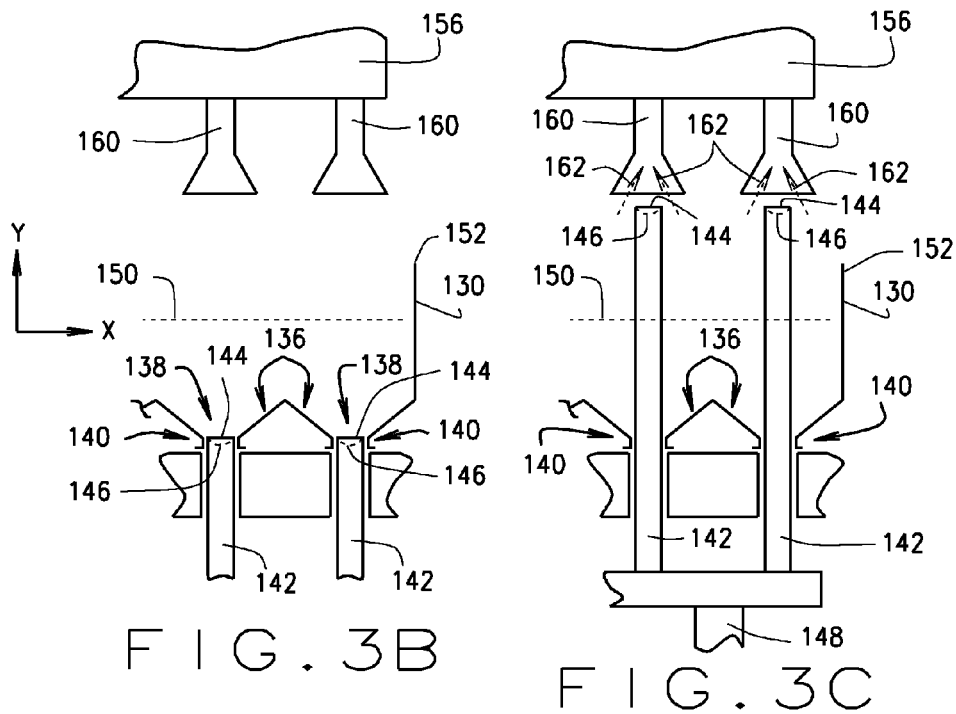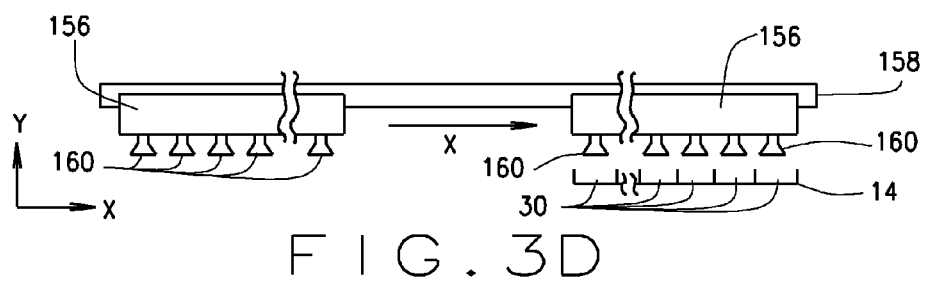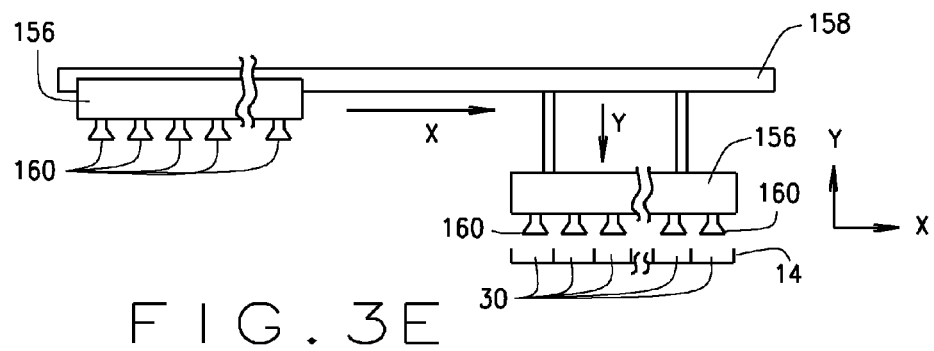

| SEED/ WELL | DIPLOID = 1 HAPLOID = 0 | NUMBER OF BLUE PIXELS | MIN. PIXELS THRESH. | SEED AREA |
|---|---|---|---|---|
| 1,1 | 1 | 321 | 45 | 4654 |
| 1,2 | 1 | 275 | 45 | 4179 |
| 1,3 | 1 | 109 | 45 | 4232 |
| 1,4 | 1 | 284 | 45 | 5763 |
| 1,5 | 1 | 528 | 45 | 5529 |
| 1,6 | 1 | 200 | 45 | 4662 |
| 2,1 | 1 | 230 | 45 | 4765 |
| 2,2 | 1 | 655 | 45 | 4950 |
| 2,3 | 1 | 449 | 45 | 4936 |
| 2,4 | 1 | 613 | 45 | 5238 |
| 2,5 | 1 | 383 | 45 | 4145 |
| 2,6 | 1 | 424 | 45 | 4363 |
| 3,1 | 1 | 544 | 45 | 4517 |
| 3,2 | 1 | 808 | 45 | 5279 |
| 3,3 | 0 | 0 | 45 | 4754 |
| 3,4 | 0 | 12 | 45 | 5472 |
| 3,5 | 1 | 240 | 45 | 4189 |
| 3,6 | 0 | 0 | 45 | 4818 |
| 4,1 | 1 | 227 | 45 | 4877 |
| 4,2 | 1 | 662 | 45 | 5419 |
| 4,3 | 1 | 49 | 45 | 4816 |
| 4,4 | 1 | 77 | 45 | 4284 |
| 4,5 | 1 | 873 | 45 | 4492 |
| 4,6 | 1 | 65 | 45 | 4516 |

FIG. 12D

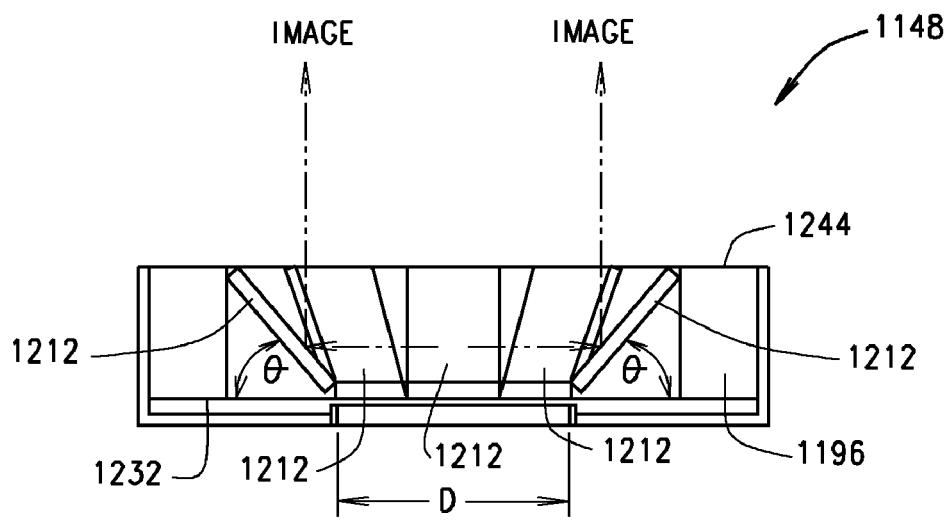
F I G . 1 6 C
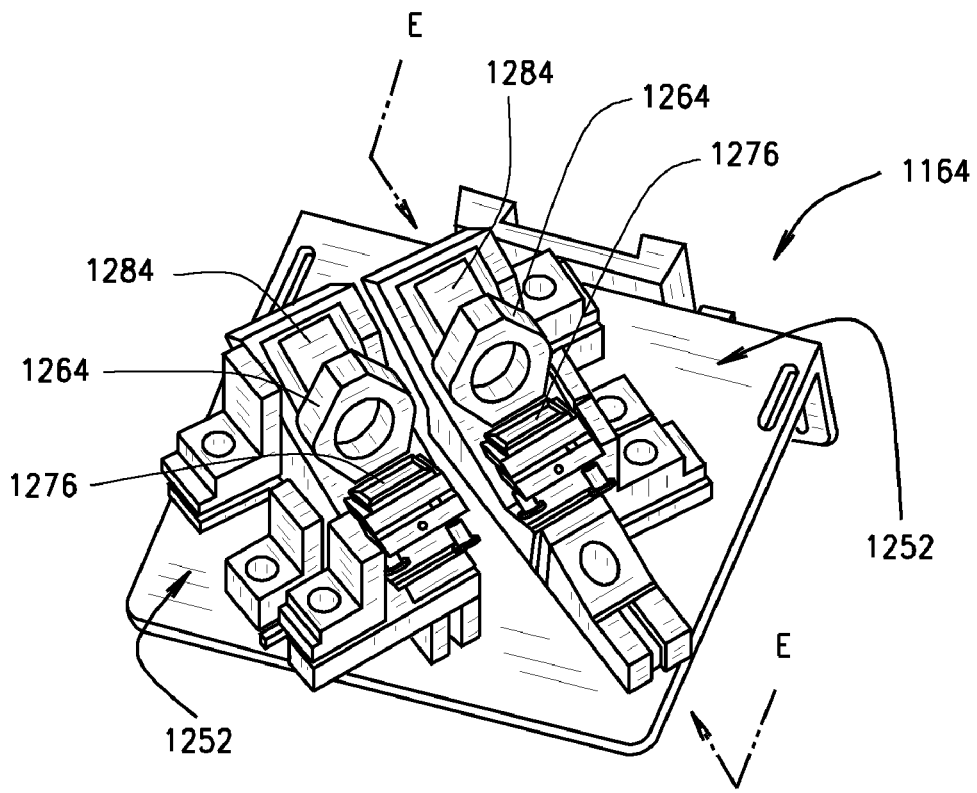
F I G . 1 6 D

SEED SORTER

CROSS-REFERENCE TO RELATED APPLICATIONS

This application claims the benefit of U.S. Provisional Application No. 60/941,155, filed on May 31, 2007, the disclosure of which is incorporated herein by reference in its entirety.

FIELD

The present disclosure generally relates generally to automated systems and methods for sorting small agricultural objects, such as seeds, based on image analysis.

BACKGROUND

The statements in this section merely provide background information related to the present disclosure and may not constitute prior art.

In the agricultural industry, and more specifically in the seed breeding industry, it is important for scientists to be able to analyze seeds with high throughput. By this it is meant that the analysis of the seeds preferably occurs not only quickly, but also reliably and with high total volume. For example, in seed breeding, large numbers of seeds are analyzed to determine whether the seeds possess particular phenotypic traits or markers of interest. Historically, seeds are manually examined, weighed, identified for the presence or absence of the desired trait or marker, and then sorted. Such manual seed analysis is a tedious, cumbersome task subject to human error.

SUMMARY

The present disclosure generally relates to systems and methods of sorting individual seeds from a plurality of seeds based on one or more identified phenotypes of each respective seed. The methods are particularly adapted for automation, which permits a greater sorting efficiency and throughput rate than was previously practical. With the automated seed sorting permitted by the various embodiments of the present disclosure, it is possible to analyze every seed in the population, and separate those identified as having a desired characteristic or trait, e.g., haploid seeds, from the other seeds at a high throughput rate.

In various embodiments, the present disclosure provides a method for determining whether individual ones of a plurality of seeds exhibit a desired phenotype. The method includes loading individual seeds onto an imaging stage, directing light onto the seeds from at least two directional angles and at a plurality of sequentially changing spectral wavelengths, collecting image data from at least two portions of each seed selected from a top portion, a bottom portion and a plurality of side portions of each seed, at each of the spectral wavelengths, and analyzing the collected image data to determine whether each seed exhibits a desired phenotype.

In various other embodiments, the present disclosure provides a seed sorting system for sorting a plurality of seeds based on identified phenotypes of the seeds. The system includes a seed loading station structured and operable to load a plurality of seeds into a seed tray such that each seed is deposited into a corresponding one of a plurality of wells in the seed tray. Additionally, the system includes at least one imaging station structured to acquire image data of the loaded seed tray at each of a plurality of filtered spectral wavelength bands for each of a plurality of viewing angles. The system further includes an off-load and sort station structured to selectably sort each seed to a particular one of a plurality of seed repositories based on whether each respective seed includes a desired phenotype, as determined by analysis of the acquired image data.

In yet other various embodiments, the present disclosure provides a method for automatically separating desired seeds from a population of seeds. The method includes depositing a plurality of the seeds into a seed tray comprising a plurality of wells, each seed being deposited into an individual well of the seed tray and imaging the seeds within the seed tray to identify seeds having a desired phenotype, and sorting the seeds identified as having the desired phenotype to a corresponding seed repository.

In still yet other various embodiments, the present disclosure provides a seed sorting system for sorting a plurality of seeds based on identified phenotypes of the seeds. The system includes a seed loading station structured to load a plurality of seeds into a seed tray such that each seed is deposited into a corresponding one of a plurality of wells in the seed tray. Additionally, the system includes a first imaging station structured and operable to acquire image data of a top portion of the loaded seed tray at each of a plurality of filtered spectral wavelength bands. The system further includes a second imaging station structured and operable to acquire image data of a bottom portion of the loaded seed tray at each of a plurality of filtered spectral wavelength bands. Further yet, the system includes an off-load and sort station structured and operable to selectably sort each seed to a particular one of a plurality of seed repositories based on whether each respective seed includes a desired phenotype, as determined by analysis of the acquired image data.

In still other various embodiments, the present disclosure provides a method for automatically identifying seeds having a desired phenotype in a population of seeds. The method includes loading each of a plurality seeds into a corresponding one of a plurality of wells in a seed tray. Image data of the loaded seed tray is then collected at a plurality of spectral wavelength bands. The collected image data is then analyzed to determine whether each seed exhibits a desired phenotype.

In other various embodiments, the present disclosure provides a method for automatically sorting haploid seeds from a population of seeds. The method includes loading a plurality of the seeds into a seed tray comprising a plurality of wells and a transparent bottom. Each seed is deposited into a respective individual well of the seed tray. Light is then directed onto a top portion of loaded seed tray utilizing at least two first light sources positioned to provide different top illumination angles. The method additionally includes sequentially passing light reflected off the top portion of the loaded seed tray by each separate first light source through a plurality of spectral filters to sequentially filter out specific spectral wavelengths of the reflected light from each first light source. Image data of the top portion of the loaded seed tray is then sequentially collected as each spectral filter is sequentially applied to the reflected light from each separate top illumination angle. The method further includes directing light onto a bottom portion of loaded seed tray utilizing at least one second light source positioned to provide at least one bottom illumination angle. The method still further includes sequentially passing light reflected off the bottom portion of the loaded seed tray, by the at least one second light source, through a plurality of spectral filters to sequentially filter out specific spectral wavelengths. Image data of the bottom portion of the loaded seed tray is then sequentially collected as each spectral filter is sequentially applied to the reflected light from the at least one bottom illumination angle. The collected top and bottom image data is then analyzed to determine whether each seed in the seed tray is absent a phenotype indicative of a diploid trait, such that the seed is classified as a haploid.

In still yet other various embodiments, the present disclosure provides a seed sorting system for sorting a plurality of seeds based on identified phenotypes of the seeds. The system includes at least one imaging station structured to acquire image data, from at least one viewing angle, of the loaded seed tray at each of a plurality of filtered spectral wavelength bands for each of a plurality of illumination angles.

In further embodiments, the present disclosure provides a method for determining whether individual ones of a plurality of seeds exhibit a desired phenotype. The method includes loading each seed of a set of seeds onto a respective one of a plurality of mirrored imaging stages having transparent bottoms, and substantially simultaneously directing light, at a plurality of sequentially changing spectral wavelengths on a top portion and a bottom portion of each loaded mirrored imaging stage. The method further includes substantially simultaneously collecting image data for a top portion, a bottom portion and a plurality of side portions of each loaded seed, at each of the spectral wavelengths, analyzing the collected image data to determine whether each seed exhibits a desired phenotype, and selectively depositing each seed of the set of seeds into a respective selected one of a plurality of seed repositories based on the determination whether each respective seed exhibits the desired phenotype.

In still further embodiments, the present disclosure provides a system for sorting a plurality of seeds based on identified phenotypes of the seeds. The system includes an optics and controller station structured and operable to substantially simultaneously collect image data of a top portion of each respective seed in a set of seeds, a bottom portion of each respective seed in the set of seeds and a plurality of side portions of each respective seed in the set of seeds. The optics and controller station is additionally structured and operable to analyze the collected image data to determine whether each seed exhibits a desired phenotype. The system further includes a seed loading, transporting and sorting station structured and operable to singulate each seed of the set of seeds from a plurality of seeds in a bulk seed hopper, transport the set of seeds to the optics and controller station, and selectively sort each seed to a respective one of a plurality of seed repositories based on whether each respective seed exhibits the desired phenotype.

In yet other embodiments, the present disclosure provides a method for determining whether individual ones of a plurality of seeds exhibit a desired phenotype. The method includes loading each seed of a set of seeds onto a respective one of a plurality of mirrored imaging stages having transparent bottoms, and substantially simultaneously directing light at a plurality of sequentially changing spectral wavelengths on a top portion and a bottom portion of each loaded mirrored imaging stage. The method additionally includes substantially simultaneously collecting image data for a top portion, a bottom portion and a plurality of side portions of each loaded seed, at each of the spectral wavelengths. The method further includes analyzing the collected image data to determine whether each seed exhibits a desired phenotype, and selectively depositing each seed of the set of seeds into a respective selected one of a plurality of seed repositories based on the determination whether each respective seed exhibits the desired phenotype.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 2A is an isometric view of the seed sorter system shown in FIG. 1, in accordance with various embodiments of the present disclosure.

FIGS. 3B and 3C are schematic side views of a picking portion of the loading station shown in FIG. 3A.

FIGS. 3D and 3E are schematic side views of a translation portion of the seed loading station shown in FIG. 3A.

FIGS. 12A-12D are exemplary pictorial and tabular illustrations showing the results of various steps of image analysis process shown in FIG. 11.

FIG. 16C is a cross-sectional view along line C-C of a mirror fixture of the imaging stages 16B, in accordance with various embodiments of the present disclosure.

FIG. 16D is an isometric view of a bottom mirror assembly of the imaging theater shown in FIG. 16, in accordance with various embodiments of the present disclosure.

Figure 19:
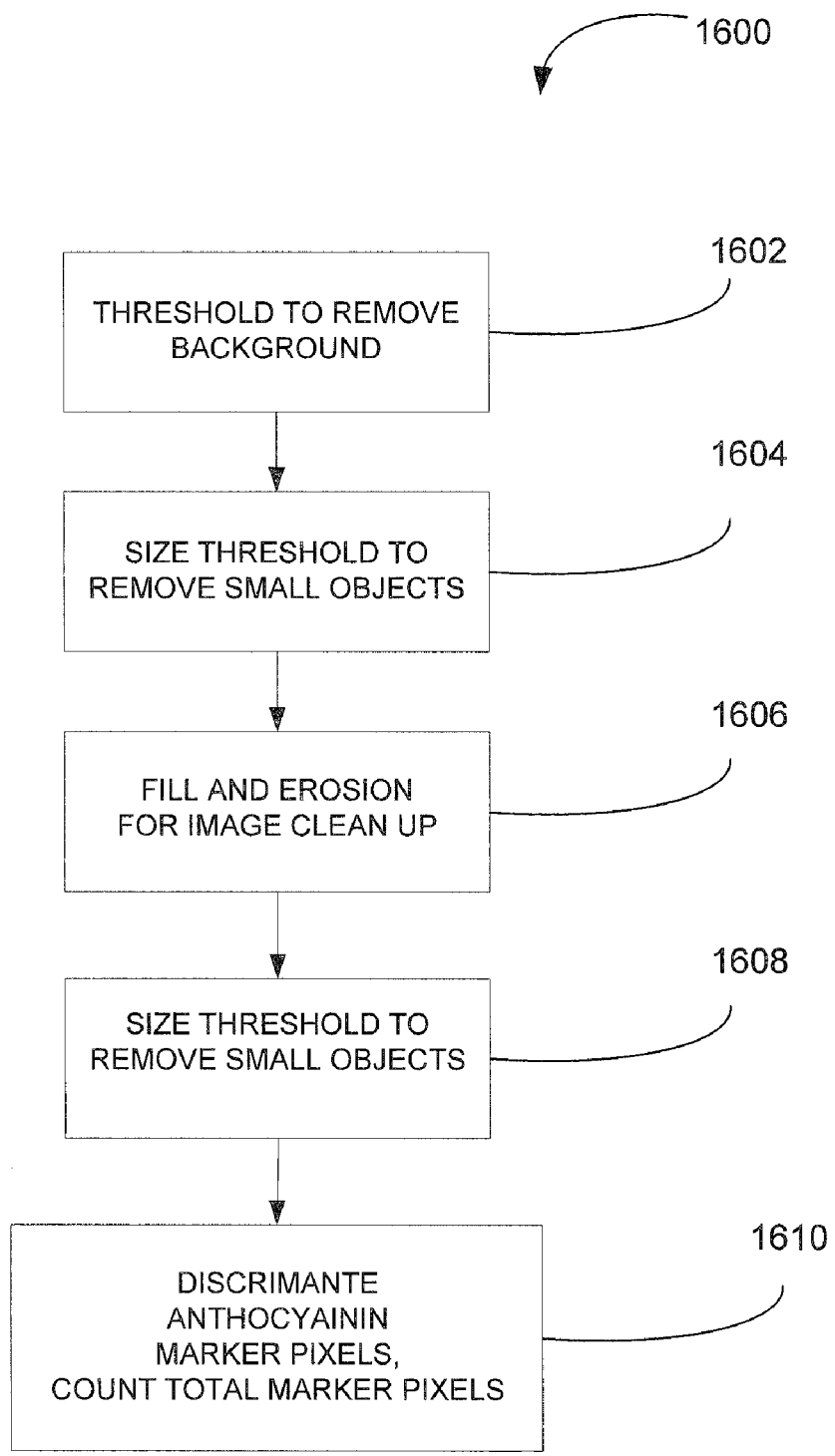
FIG. 19 is flow chart illustrating an overview of an exemplary image analysis process executed by a master controller system of the seed sorter system, shown in FIG. 13A, in accordance with various embodiments of the present disclosure.
Figure 20A:
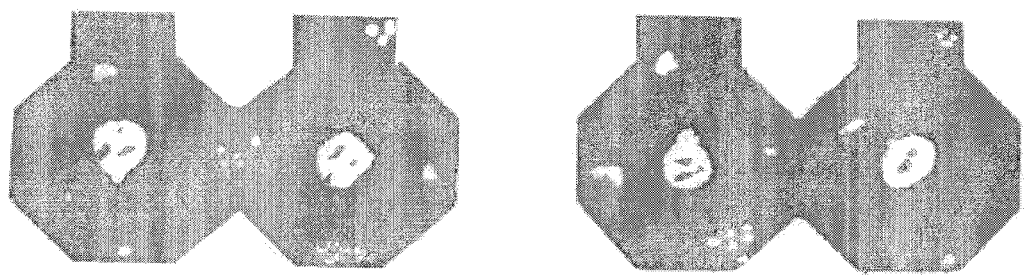
Figure 20B:
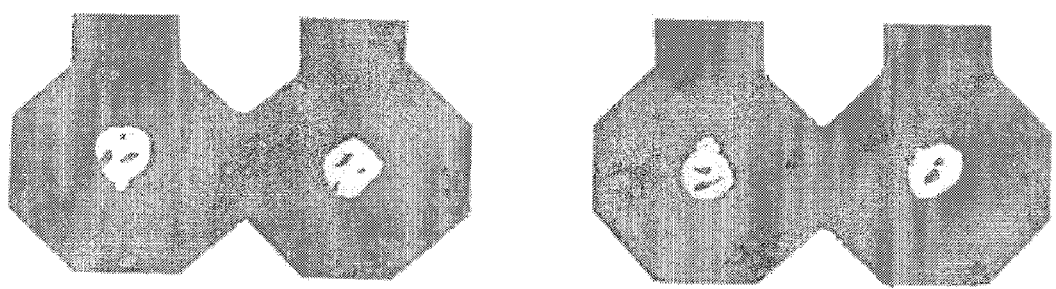
Figure 20C:
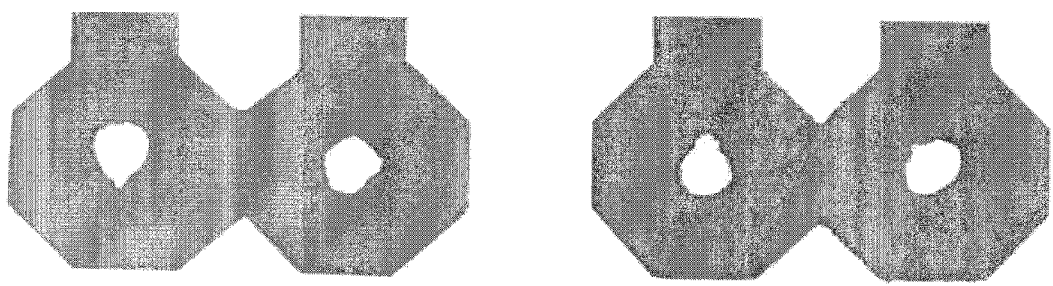

FIGS. 20A, 20B and 20C are exemplary pictorial illustrations showing the results of various steps of image analysis process shown in FIG. 19: FIG. 20A illustrates an exemplary pictorial illustration of a 'top view' image after a background mask has been applied; FIG. 20B illustrates an exemplary pictorial illustration of a 'top view' image after background and first size threshold masks have been applied; and FIG. 20C illustrates an exemplary pictorial illustration of a 'top view' image after the background mask, the first size threshold mask and the fill and erosion mask have been applied.

DETAILED DESCRIPTION

The following description is merely exemplary in nature and is in no way intended to limit the present teachings, application, or uses. Throughout this specification, like reference numerals will be used to refer to like elements.

Figure 1:
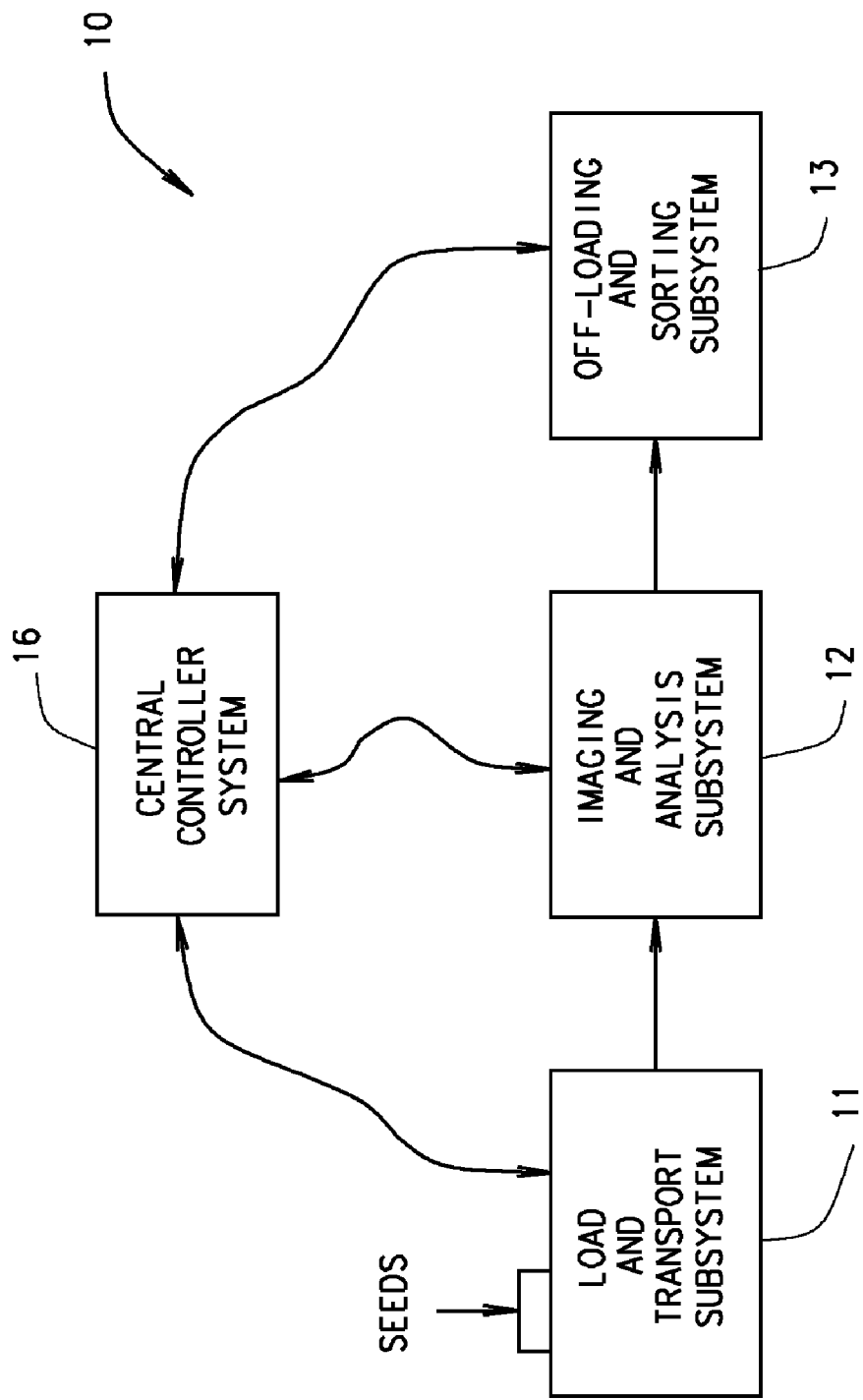
FIG. 1 is a block diagram of an automated seed sorter system structured and operable to singulate a plurality of seeds, image, analyze and categorize each seed, and sort each seeds based on the categorization, in accordance with various embodiments of the present disclosure.

FIG. 1 is a block diagram of an automated seed sorter system 10 that is structured and operable to receive a plurality of any desired type of seed, singulate the seeds, image and analyze each singulated seed to identify desired characteristics or phenotypes, and sort the seeds based on the identified desired characteristics or phenotypes. Generally, the automated seed sorter system 10 includes a load and transport (L&T) subsystem 11 that is structured and operable to receive the plurality of desired type of seeds, singulate the seeds and transport the seeds to an imaging and analysis (I&A) subsystem 12. The I&A subsystem 12 is structured and operable to collect image data of each singulated seed and analyze the collected image data to categorize each respective seed. For example, each seed can be categorized based on whether each respective seed possesses one or more desired characteristics or phenotypes.

An off-loading and sorting (OL&S) subsystem 13 then sorts each respective seed to a particular one or more of a plurality of seed repositories based on categorization of each respective seed. For example, all seeds possessing one or more desired characteristics or phenotypes, as identified by the I&A subsystem 12, can be sorted to one or more corresponding seed repositories, while all seeds not possessing the one or more desired characteristics or phenotypes can be sorted to one or more corresponding other seed repositories. Similarly, all seeds for which it is uncertain whether the seeds possess the one or more desired characteristics or phenotypes can be sorted to one or more corresponding other seed repositories. Further yet, all rejected seeds, e.g., partial seeds, double seeds or seeds that do not meet predetermined size criteria, can be sorted to one or more corresponding other seed repositories. The automated seed sorter system 10 additionally includes a central controller system 16 that is structured and operable to control all the operations of the seed sorter system 10. That is, the central controller system 16 simultaneously controls and coordinates the operations of each of the L&T subsystem 11, the I&A subsystem 12 and the OL&S subsystem 13 to carry out the singulation, imaging, analysis and sorting of each of the plurality of seeds loaded into the L&T subsystem 11, as described below.

It should be understood that the various embodiments of the seed sorter system 10, exemplarily illustrated and described herein, include various stationary braces, beams, platforms, pedestals, stands, etc., to which various components, devices, mechanisms, systems, subsystems, assemblies and sub-assemblies described herein are coupled, connected and/or mounted. Although such braces, beams, platforms, pedestals, stands, etc., are necessary to the construction of various embodiments of the seed sorter system 10, description of their placement, orientation and interconnections are not necessary for one skilled in the art to easily and fully comprehend the structure, function and operation of the various embodiments of the seed sorter system 10. Moreover, such braces, beams, platforms, pedestals, stands, etc., are clearly illustrated throughout the figures and, as such, their placement, orientation and interconnections are easily understood by one skilled in the art. Therefore, for simplicity, such braces, beams, platforms, pedestals, stands, etc., will be referred to herein merely as system support structures, absent further description of their placement, orientation and interconnections.

Referring now to FIG. 2A, in various embodiments, seed sorter system 10 can be a four station rotary transport seed sorter system, wherein the L&T subsystem 11 can comprise a seed loading station 100 and a rotary seed transport subsystem 200, the I&A subsystem 12 can comprise a first seed imaging station 300 and a second imaging station 400, and the OL&S subsystem 13 can comprise a seed off-load and sort station 500. Additionally, the central controller system 16 of the seed sorter system 10 can comprise a main controller system 600.

Figure 2B:
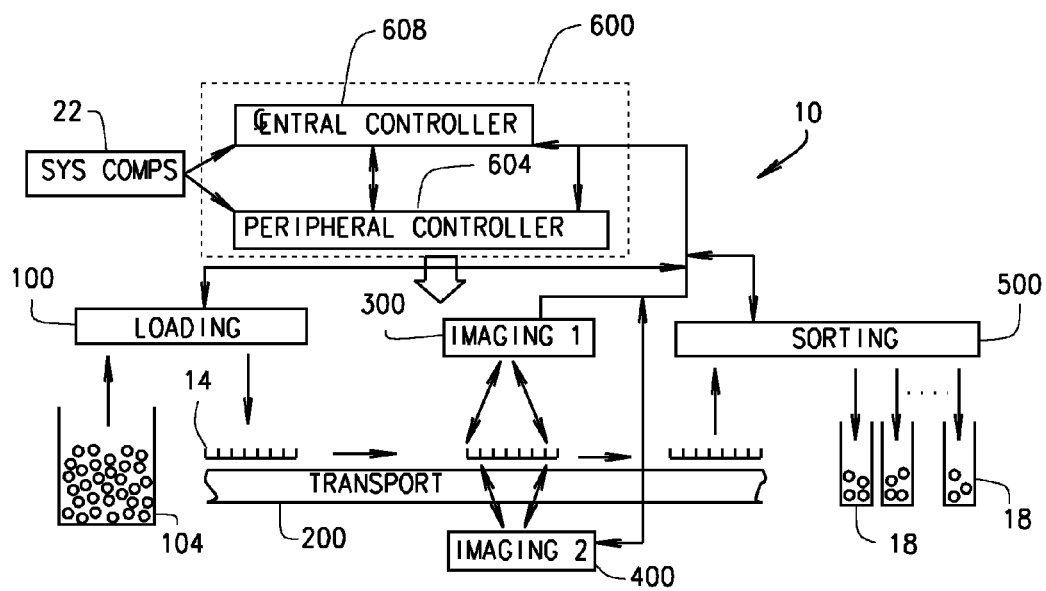
FIG. 2B is a functional block diagram of the seed sorting system shown in FIG. 2A, in accordance with various embodiments of the present disclosure.

Referring to FIGS. 2A and 2B, FIG. 2B illustrates a functional block diagram of the seed sorting system shown in FIG. 2A, in accordance with various embodiments. Generally, in such embodiments, the seed sorter system 10 is structured and operable to isolate a plurality of seeds from a bulk seed hopper 104 and place the isolated seeds in one of a plurality of transparent multi-well seed trays 14 at the seed loading station 100. More particularly, the seed trays 14 include a transparent bottom, for example a quartz bottom, as described below. The seed trays 14 are retained within an indexing transport table 202 of the transport subsystem 200 that is structured and operable to incrementally position each seed tray 14 at, i.e., adjacent to, each of the loading station 100, the first imaging station 300, the second imaging station 400 and the off-loading station 500. The seed sorter system 10 is additionally structured and operable to collect multiple images of at least one side of the seeds within the seed tray 14, via the first imaging station 300. The seed sorter system 10 is further structured and operable to collect multiple images of at least one other side of the seeds within the seed tray 14, via the second imaging station 400. The images collected at the first and second imaging stations 300 and 400 can be any desirable type of images. For example, the images can be visual images, near infra-red (NIR) images or NMR/MRI images, or any other type images. In various embodiments, the first and second imaging stations 300 and 400 collect a plurality of digital images at various spectral wavelengths.

In additional embodiments, this invention contemplates the automated sorting of haploid seed on the basis of characteristics detectable with analytical instruments other than optical detection. For example, seed may be sorted based on a characteristic other than color or fluorescent markers, such as oil content. The invention further contemplates an apparatus and method for the automated screening and sorting of haploid seeds that is based on a variety of analytical techniques that when used in tandem can facilitate the sorting of haploid and diploid seeds in a highly automated manner, wherein MRI or NMR technology is employed either in parallel or in substitution of the optical technology of the present invention.

In a specific aspect, seed would be sorted based on oil content, taking advantage of phenotypic differences between haploid and diploid seed in oil content, which is generally lower in haploid seed than diploid seed. It is possible to increase the difference in oil content between haploid and diploid seed by using a haploid inducer line that has been bred for increased oil, thus enabling automated phenotypic screening of a population of seeds on the basis of oil content. Methods for detecting oil content in seed using magnetic resonance imaging (MRI) have been disclosed in U.S. Pat. No. 7,367,155, which is incorporated herein by reference in its entirety. Oil content screening can greatly reduce the time to select haploid seed for use in germplasm improvement activities, as well as facilitate screening a much larger volume of seed.

As described further below, in various embodiments, the seed sorter system 10 illustrated and described with reference to FIGS. 1 through 12D can be structured and operable to implement multivariate analysis to analyze the image data of the multiple images collected at the first and second imaging stations 300 and 400. More particularly, in such embodiments, the image data can be communicated to the main controller system 600 where multivariate analysis is performed on the collected image data to identify whether individual seeds in the seed tray 14 possess one or more desired phenotypes, i.e., observable traits and/or characteristics. Further yet, the seed sorter system 10 is structured and operable to individually off-load each seed from each seed tray 14 and sort each seed to a particular one of a plurality of seed repositories 18 based on the identified phenotype of the respective seed as determined via the multivariate analysis.

The operation of the seed sorter system 10, as illustrated and described with reference to FIGS. 1 through 12D is controlled and automated by the main controller system 600 such that the operations performed by the loading station 100, the first and second imaging stations 300 and 400, and the off-loading station 500 occur substantially without need for human interaction, intervention or control. However, such actions as loading the seeds into the bulk seed hopper 104 and/or physically manipulating and/or changing the seed repositories 18 (either individually or collectively), and various other necessary hand setup and/or calibration can be performed manually with human participation.

Generally, in various embodiments, the main controller system 600 can include one or more processors and/or microprocessors, and one or more electronic data storage devices utilized to store and execute various custom programs, applications and/or algorithms to effectuate the operation of the seed sorter system 10. Accordingly, the main controller system 600 can comprise a specially programmed computer, or computer system, in communication with associated system devices that enable communication with and control the operations of the various stations and corresponding components 22 of the seed sorter system 10. Although the main controller system 600 is exemplarily illustrated in FIG. 2A as a single unit, the main controller system 600 can be a single computer based system or a plurality of computer based subsystems networked together to coordinate the simultaneous operations of the seed sorter system 10, as described herein. For example, in various embodiments, the main controller system 600 can include a plurality of peripheral controller subsystems 604, e.g., a peripheral controller subsystem 604 for each station described herein. Each peripheral controller subsystem 604 can include one or more processors, microprocessors and electronic data storage devices that effectuate communication with various seed sorter system components 22, e.g., sensors, devices, mechanisms, motors, tools, etc., and are networked together with a main controller subsystem 608 to cooperatively operate all the stations, systems and subsystems of the seed sampler system 10, as illustrated and described with reference to FIGS. 1 through 12D. Or, alternatively, the main controller system 600 can comprise a single computer communicatively connected to all the various system components 22 to cooperatively operate all the stations, systems and subsystems of the seed sampler system 10, as illustrated and described with reference to FIGS. 1 through 12D.

In addition to storing programming for controlling the operation of the seed sorter system 10, the electronic data storage device(s) (or other data storage functionality, not explicitly shown but inherently present) provided within the main controller system 600 is used to store the collected images and related image data relating to each individual seed within the seed tray 14 in a database or other suitable format. Additionally, the data storage device(s) of the main controller system 600 can also store location data received from, or derived in connection with controlling the operation of the off-loading station 500 concerning the repositories 18 where the seeds have been deposited. This location data is correlated in the database or other format with the image data on an individual seed-by-seed basis.

As described above, the main controller system 600 communicates with various seed sorter system components 22 that include various system sensors. The system sensors operate to detect conditions of interest during operation of the seed sorter system 10 and communicate that information to the main controller system 600. With this information, the main controller system 600 generates control commands that effectuate the operations and actions taken by the various stations and components of the seed sorter system 10. For example, the sensed condition information may concern: the successful loading of the seeds from the seed hopper 104; the positioning of the tray(s) 14 along the transport path during operation of the transport subsystem 200; the deposition of each seed into the proper seed repository 18; the status (for example, position, location, vacuum, pressure, and the like) of various component parts of the various stations 100, 300, 400 and 500; operation, maintenance, performance, and error feedback from the various components of each station 100, 300, 400 and 500 (separate from, or perhaps comprising or in conjunction with, collected data); and the like. More specifically, sensor information that is collected and processed for use in controlling the operation of the seed sorter system 10 can include information like: device or component status; error signals; movement; stall; position; location; temperature; voltage; current; pressure; and the like, which can be monitored with respect to the operation of each of the stations, subsystems and associated components of the seed sorter system 10.

Figure 3A:
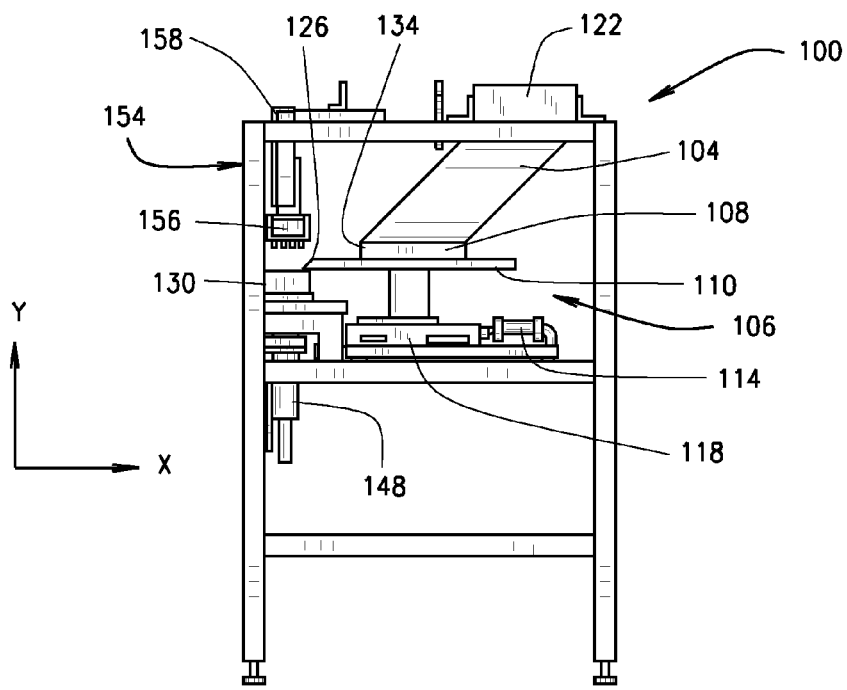
FIG. 3A is an isometric view of a seed loading station of the seed sorter system shown in FIG. 2A, in accordance with various embodiments of the present disclosure.

Referring now to FIGS. 2A and 3A, in accordance with various embodiments, the seed loading station 100 includes a seed feeder mechanism 106 positioned beneath an outlet 108 of the bulk seed hopper 104. The seed feeder mechanism generally includes a feed platform 110 operably connected to an X-axis linear actuator 114 via a translation stage 118. In operation, a large quantity of seeds is placed, either manually or via an automated means, in the bulk seed hopper 104, via a bulk seed hopper inlet 122. The seeds are then dispersed at a desired rate onto the feed platform 110 that is being linearly reciprocated along the X axis such that a leading edge 126 of the feed platform 110 linearly moves back and forth across a portion of an open top of a seed picking reservoir 130. The bulk seed hopper outlet 108 is structured such that as the feed platform 110 moves in a first direction toward the seed picking reservoir 130, a desired amount of seeds are dispensed onto the feed platform 110. Then, as the feed platform reciprocates in a second direction away from the seed picking reservoir 130, a leading lip 134 of the hopper outlet 108 pushes the newly dispensed seeds toward the leading edge 126 of the feed platform 110. This causes a certain amount of the seeds near the feed platform leading edge 126 to fall into the seed picking reservoir 130.

Referring additionally to FIGS. 3B and 3C, the seed picking reservoir 130 includes a plurality of concave-shaped (inwardly sloped) bottom portions 136. The sloped portions 136 serve to direct the seeds, through the force of gravity, toward a bottom 138 of the seed picking reservoir 130, thereby enabling the seed loading station 100 to isolate and load individual seeds within the seed picking reservoir 130 into a corresponding seed tray 14, as described below. At the bottom 138 of each concave-shaped portion 136 is an opening 140. Positioned within each opening 140 is a linear air piston 142. When positioned in a retracted, or un-actuated, position, as shown in FIG. 3B, an end 144 of each piston 142 is located such that it is substantially flush with the bottom 138 of each respective opening 140. It will be recognized that "substantially flush" in this context includes a position slightly below the bottom 138 where the opening 140 may act to hold or funnel an individual seed for subsequent capture by the respective piston 142, as described below.

The end 144 of each piston 142 is provided with a concave depression 146 (illustrated in dotted lines) having a perimeter that is slightly smaller than the outer diameter of the piston 142. The perimeter of the depression 146 is generally sized to be commensurate with, or slightly larger than, the expected average size of the seeds deposited into the seed picking reservoir 130. This allows for the handling of individual seeds of non-uniform size and/or shape. An air drive 148 operates under the control of the main controller system 600 to linearly move the pistons 142 between the retracted position, shown in FIG. 3B, and an extended, or actuated, position, shown in FIG. 3C. Although the air drive 148 is shown as a single air drive configured to simultaneously manipulate the position of each of the pistons 142, it will be understood that the seed loading station 100 could include a separate, independent air drive 148 for each piston 142.

In operation, when the pistons 142 begin to move from the retracted position to the extended position, the concave depression 146 at each piston end 144 captures an individual one of the seeds from the collected mass of seeds (generally indicated at 150) in the seed picking reservoir 130. As the pistons 142 move to the extended position, the captured seeds are raised above the collected mass of seeds 150 to a location approximately at a top edge 152 of the seed picking reservoir 130. Once the pistons 142 are in the extended position and the seeds have been raised to the top edge 152, it is necessary to remove the captured seeds from the ends of the respective pistons 142 for further handling.

To remove the captured seeds and place them into a seed tray 14 retained in, or on, the indexing transport table 202, shown in FIG. 2A, the seed loading station 100 further includes a pick and place device 154. The pick and place device 154 generally includes a head unit 156 operably coupled to an X-Y translation stage operable to bi-directionally move the head unit along the X and Y axes. The head unit 156 includes a plurality of vacuum cups 160 arranged and oriented to longitudinally, collinearly correspond with the pistons 142. Accordingly, when the pistons 142 are in the extended position, the captured seeds on each piston are positioned adjacent a corresponding one of the vacuum cups 160. In various embodiments, when the pistons 142 are in the extended position, the captured seeds are lightly in contact with the respective corresponding vacuum cups 160. To minimize the likelihood of damage caused by such contact, each vacuum cup 160 can be spring loaded such that each vacuum cup 160 contacts the respective seeds with desired, non-damaging pressure.

Once the pistons are in the extended position and captured seeds are near, or in light contact with, the vacuum cups 160, a slight vacuum is drawn (illustrated by dotted arrows 162) to remove the seeds from the pistons and hold the seeds within the vacuum cups 160. The vacuum pressure used to remove and retain the seeds is controlled by the main controller system 600. This vacuum can be drawn using Venturi forces in a manner well known in the art. The pistons 142 are then withdrawn to the retracted position, leaving the head unit 156 'loaded', i.e., having the seeds retained within the vacuum cups 160, and the process for capturing a subsequent set of seeds is begun.

Referring now to FIGS. 3A-3D, once the individual seeds are removed from the pistons and held by the vacuum cups 160, the seeds are placed in a seed tray 14. More particularly, each seed tray includes a plurality of wells 30 and each individual seed is placed in a corresponding one of the seed tray wells 30. To place the seeds in the seed tray wells 30, the X-Y translation stage 158 moves the head unit 156, including the vacuum cups 160 and the seeds held therein, along the X-axis to a position above a seed tray 14 positioned adjacent the seed loading station 100. More specifically, the X-Y translation stage 158 positions the 'loaded' head unit 156 over the respective seed tray 14 such that each vacuum cup 160 and respective seed held therein is aligned above a respective seed tray well 30. As described above, the indexing transport table 202 is controlled by the main controller system 600 to incrementally advance one or more seed trays 14 to sequentially position each seed tray 14 adjacent each of the loading station 100, the first imaging station 300, the second imaging station 400 and the off-loading station 500.

Each vacuum cup 160, under the control of the main controller system 600, then releases the respective seeds, thereby depositing each seed in the corresponding seed tray well 30. In various embodiments, the vacuum cups 160 can emit a positive pressure to aid gravitational forces in releasing the seeds from the vacuum cups 160 and depositing the seeds in the respective seed tray wells 30.

Referring now to FIG. 3E, in various embodiments, when the head unit 156 is positioned above a seed tray 14, the indexing transport table 202 and the seed trays 14 can be a distance below the head unit 156 such that movement of the head unit 156 along the Y axis is required to accurately and consistently deposit the seeds in the seed tray wells 30. In such embodiments, the X-Y translation stage 158, under the control of the main controller system 600, operates to move the head unit 156 along the Y axis to position the seeds retained within the vacuum cups 160 in close proximity of the seed tray wells 30. The seeds can then be released, or ejected, from the vacuum cups 160 such that each seed is deposited into a respective one of the seed tray wells 30.

In various embodiments, the head unit 156 includes the same number and arrangement of vacuum cups 160 as the wells 30 in the seed trays 14. For example, if the seed trays 14 have twenty-four wells 30 arranged in a 4×6 array format, the head unit 156 will also include twenty-four vacuum cups 160 arranged in a 4×6 array format that corresponds with the 4×6 array format of the seed tray wells 30. In this way, one seed tray 14 can be fully loaded with seeds using a single 'pick-and-place' operation of the pick and place device 154, as described above.

In various other embodiments, the head unit 156 can include an even submultiple number and arrangement of vacuum cups 160 as the number and arrangement of the seed tray wells 30. For example, if the seed tray 14 includes ninety-six wells 30 arranged in a 16×24 array format, then the head unit 156 can include twenty-four vacuum cups 160 in a 4×6 array format. Accordingly, to deposit a seed in each of the ninety-six wells 30, the pick and place device 154 will be required to complete four consecutive 'pick-and-place' operations. Appropriate X-Y translation by the X-Y translation stage 158 will be implemented to accurately position the vacuum cups 160 for each consecutive 'pick-and-place' operation to deposit a seed in each of the ninety-six seed tray wells 30.

Figure 4A:
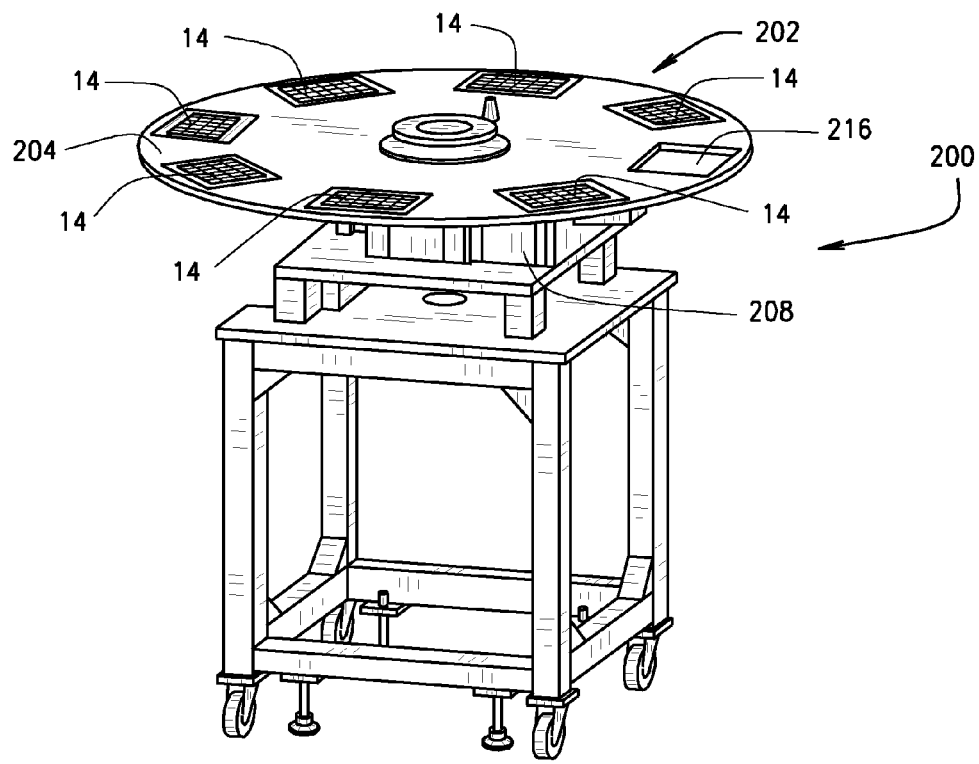
FIG. 4A is an isometric view of a seed transport subsystem of the seed sorter system shown in FIG. 2A, in accordance with various embodiments of the present disclosure.
Figure 4B:
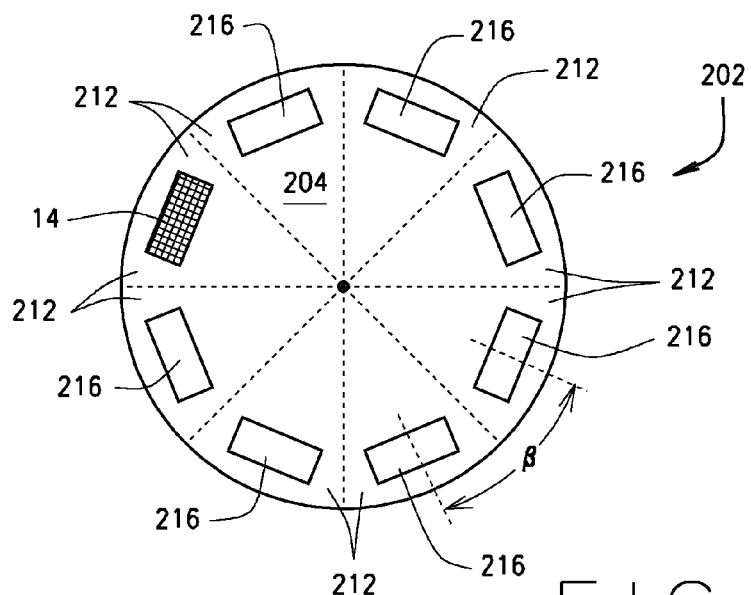
FIG. 4B is a top view of the transport subsystem shown in FIG. 4A.

Referring now to FIGS. 2A, 4A and 4B, as described above, the seed transport subsystem 200 includes an indexing transport table 202. In various embodiments, the indexing transport table 202 comprises a round platform 204 that is rotationally mounted to a drive device 208, such as a high torque stepper motor, controlled by the main controller system 600. The round platform 204 is virtually divided into a plurality of pie-shaped sectors 212, with each sector 212 including a seed tray cut-out 216 sized and shaped to receive and support a single seed tray 14. The round platform 204 can have an even or odd number of sectors 212 based in large part on the diameter of the round platform 204, the size of the seed trays 14 and the needs of the transport application.

In operation, the drive device 208 for the indexing transport table 202 is controlled by the main controller system 600 to advance, either clockwise or counter clockwise, to incrementally advance each seed tray 14 to positions adjacent each of the stations 100, 300, 400 and 500. For example, upon each advancement, the drive device 208 rotates the platform 204 an angular amount equal to $\beta$, where $\beta$ is equal the angle between centers of adjacent cut-outs 216. Accordingly, very precise rotational advancements are made to accurately align the seed trays 14 adjacent each of the stations 100, 300, 400 and 500 such that each of the stations 100, 300, 400 and 500 can perform its designated function, as described herein, with respect to the seed trays 14 and the seeds retained therein. To the extent necessary, the peripheral edges of the platform 204 can be supported with rollers, guides, slides, or the like, to assist with smooth rotation of the indexing transport table 202.

Alternatively, the indexing transport table 202 can comprise any suitable conveyance mechanism such as, for example, a belt conveyor, roller conveyor, and the like.

Figure 5A:
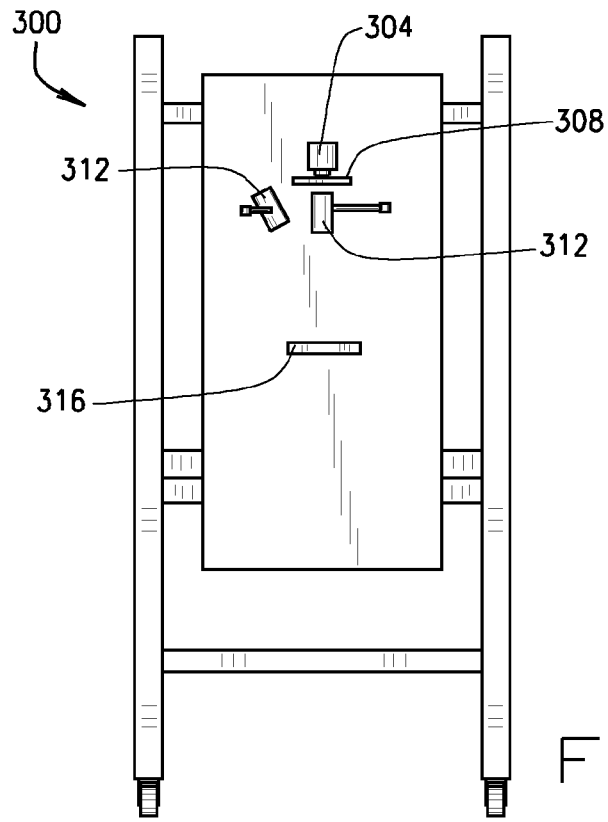
FIG. 5A is a front view of a first imaging station of the seed sorter system shown in FIG. 2A, in accordance with various embodiments of the present disclosure.
Figure 5B:
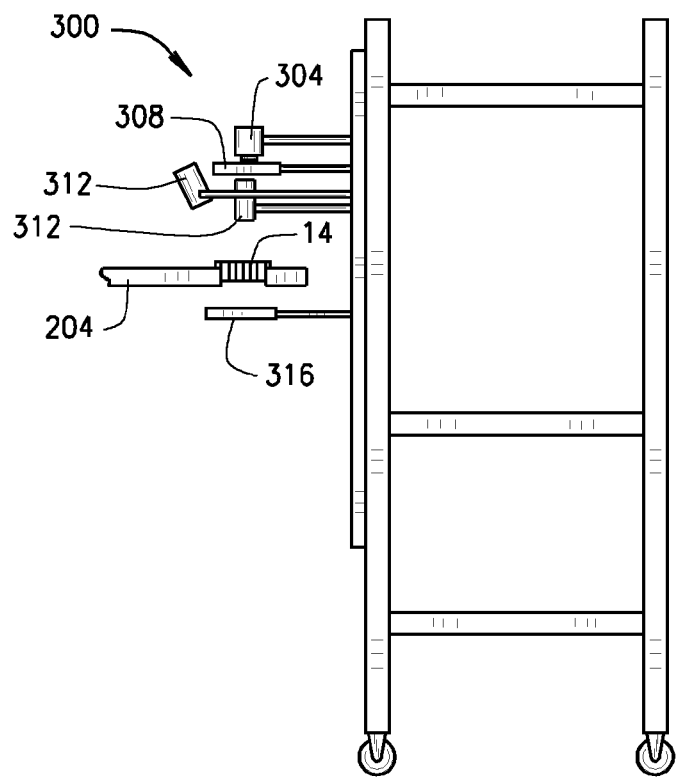
FIG. 5B is a side view of the first imaging subsystem shown in FIG. 5A.

Referring now to FIGS. 2A, 5A and 5B, the first imaging station 300 includes at least one first imaging device 304 suspended over the indexing transport table 202 by the system support structure. The first imaging device 304 is mounted to the system support structure such that a field of view of the first imaging device 304 includes the top, or upward facing, portion of the seed tray 14 positioned adjacent the first imaging station 300. That is, the first imaging device 304 is positioned such that the first imaging device 304 can collect image data of the top of the loaded seed tray 14 and, more particularly, image data of the top portion of each seed in the loaded seed tray 14. Accordingly, the first imaging device 304 can also be referred to herein as the top imaging device 304. As used herein, reference to the top portion of the seed(s) refers to the portion of the seed(s) that is facing upward with respect to the orientation of each seed within the respective seed tray well 30. That is, as used herein, the top portion of the seed(s) refers to the portion of the seed(s) generally facing away from, and not resting on, the transparent bottom of each respective seed tray well 30, and does not refer to the independent structure or anatomy of the seed(s). The image data collected at the first imaging station 300 is transmitted to the main controller system 600 for storage and analysis, as described below.

The first imaging device 304 can be any suitable imaging device selected in accordance with the imaging goals of the seed sorter system 10. For example, in connection with an analysis for external seed coat damage, the first imaging device 304 may comprise a digital camera operable in the visible light range. Alternatively, for internal seed analysis, the first imaging device 304 may comprise a camera operable in the near infra-red light range (see, U.S. Pat. No. 6,646,264, the disclosure of which is hereby incorporated by reference). Still further, the first imaging device 304 may comprise a camera which implements NMR/MRI imaging techniques (see, U.S. Pat. No. 7,367,155, the disclosure of which is hereby incorporated by reference).

In various embodiments, the first imaging station 300 additionally includes at least one first, or top, multi-spectral high-speed filter device 308, i.e., one first multi-spectral high-speed filter device 308 for each first imaging device 304. The first filter device 308 is positioned between the lens of the first imaging device 304 and the respective loaded seed tray 14 adjacent the first imaging station 300. The first multi-spectral high-speed filter device 308 includes a plurality of spectral filters that filter various wavelengths of light such that image data for each of the seeds in the loaded seed tray 14 can be collected at various spectral wavelengths. For example, in various embodiments, the first multi-spectral high-speed filter device 308 can be structured to include a filter wheel including six band pass filters to provide six different bands, i.e., wavelength bands, of spectral filtering. Accordingly, the first imaging device 304 and first filter device 308 can cooperatively operate to collect image data of the top portion of the loaded seed tray 14 adjacent the first imagine station 300 and each seed therein at a plurality of different spectral wavelengths, also referred to herein as multi-spectral imaging.

The first imaging station 300 further includes a plurality of first, or top, light sources 312 for illuminating the field of view of the first imaging device 304, i.e., the top portion of loaded seed tray 14 adjacent the first imaging station 300, from a plurality of different specifically calibrated angles. In various embodiments, the light sources 312 are mounted, via system support structure, at different specifically calibrated angles and controlled to sequentially illuminate the respective seed tray 14 at the different illumination angles. That is, the multi-spectral images are collected using any desired sequence of illuminating one or more of the first light sources 312. For example, in various embodiments the first imaging station includes a pair of first light sources 312. Multi-spectral images are first collected using only one of the first light sources 312 to illuminate the respective seed tray 14 at a first illumination angle. Then multi-spectral images are collected using the other, e.g., second, first light source 312 to illuminate the respective seed tray 14 at a second illumination angle. Thus, the first imaging station 300 collects multi-spectral image data of the top portion of seeds in the respective seed tray 14 using different illumination angles and at a plurality, e.g., six, different spectral wavelengths. Particularly, each light source 312 employs a corresponding filter device 308 for filtering multiple wavelengths. As described in detail below, the first imaging device 304 transmits the collected multi-spectral image data for each illumination angle and each wavelength to the main controller system 600 for storage and analysis.

The first light sources 312 can be any type of light suited for the particular imaging application of the seed sorter system 10. For example, the first light sources 312 can be incandescent lights, fluorescent lights, ultraviolet lights, infrared lights, halogen lights, and the like. In various embodiments, the first light sources 312 are incandescent lights.

In various embodiments, the first imaging station 300 includes a first black background plate 316 suspended by system support structure beneath the indexing table platform 204. More specifically, the first background plate 316 is positioned such that, upon each advancement of the indexing table platform 204, the seed tray cut-out 216 positioned adjacent the first imaging station 300 and the respective transparent bottom seed tray 14 therein is directly above the first background plate 316. The first background plate 316 provides a solid dark background for each respective transparent bottom seed tray 14 during imaging of the top portion of the respective seed tray 14 and seeds retained within the wells 30.

In various embodiments, the seed tray 14 can be constructed to have shallow wells 30 such that the sides of seeds held therein are exposed and viewable by one or more additional imaging devices 304. Therefore, additional image data, at different viewing angles of each seed, is obtainable by adding imaging devices 304 positioned to view the seeds from additional different angles. Alternatively, it is contemplated that additional image data can be collected at different viewing angles of each seed by robotically moving a single first imaging device 304 to collect additional image data from multiple angles of view. It should be understood that in such embodiments, additional and/or robotically moving filter devices 308 and/or first light sources 312 can be implemented to provide desired illumination and spectral filtering.

Still yet in other embodiments, a plurality of mirrors can be utilized to view and collect image data for each seed from a plurality of sides, or angles. Therefore, additional image data, at different viewing angles of each seed, can be obtained, via reflected seed images from the mirror(s), utilizing a minimal number of stationary imaging devices 304. For example, in various implementations, each well 30 of the seed trays 14 can include one or more mirrors, e.g., planar mirrors, on the sides of each respective well 30. Or, in yet other implementations, as further described below in reference to FIGS. 13 through 20C, each seed can be positioned within an annular mirrored imaging stage to view and collect image data for each seed from a plurality of sides, views or angles, utilizing a single stationary imaging device, such as imaging devices 304. In such embodiments, other or additional filter devices and/or lighting sources can be added as necessary to provide desired illumination and spectral filtering.

With further reference to FIGS. 2A, 5A and 5B, the image data collected by the first imaging device 304 includes data relating to the seed tray 14 and to the seeds retained in each well 30 of the seed tray 14. The image data is transmitted to the main controller system 600 and stored (at least temporarily) in an electronic data storage device of the main controller system 600. The main controller system 600 analyzes the data to correlate each seed in the seed tray 14 to the specific, corresponding well 30 location within the seed tray 14. Accordingly, all the collected multi-spectral image data, i.e., all the image data from the first imaging device 304 at each illumination angle and each filtered wavelength, is analyzed and parsed to correlate the image data for each individual seed to the particular well 30 in which the respective seed is retained. In this way, a link exists between each seed, the corresponding well 30 and the corresponding image data.

Figure 6A:
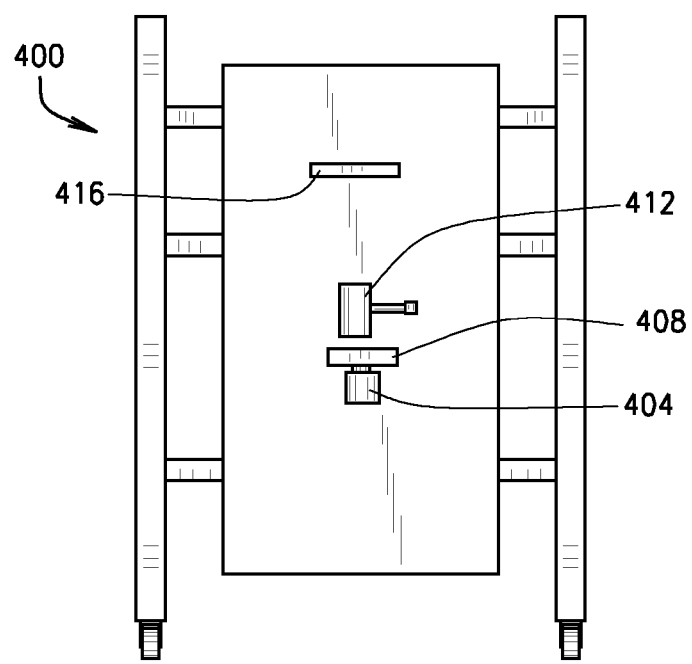
FIG. 6A is a front view of a second imaging station of the seed sorter system shown in FIG. 2A, in accordance with various embodiments of the present disclosure.
Figure 6B:
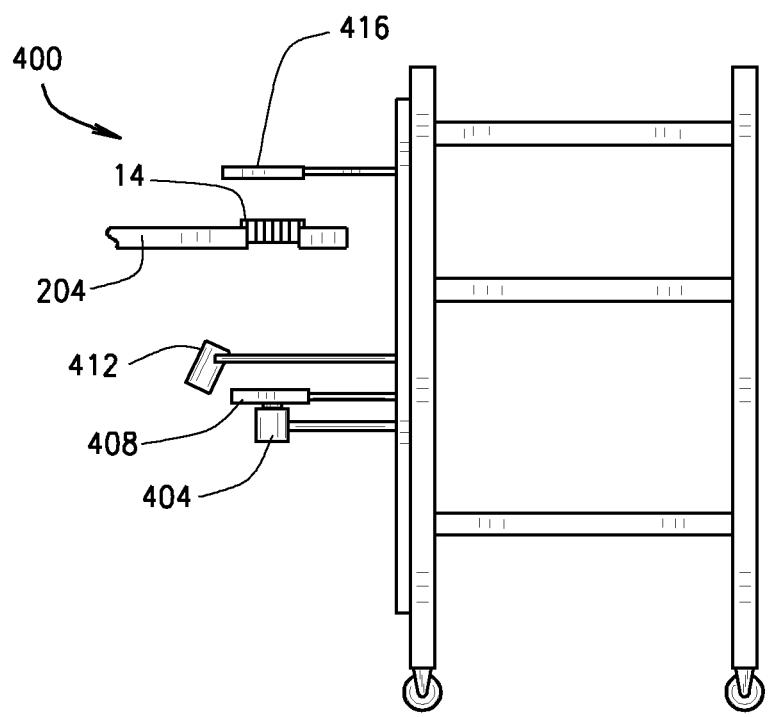
FIG. 6B is a side view of the second imaging subsystem shown in FIG. 6A.

Referring now to FIGS. 2A, 6A and 6B, once the image data of the top portion of the seeds and seed tray 14 is collected at the first imaging station 300, the indexing table platform 204 is advanced to subsequently position the respective seed tray 14 adjacent the second imaging station 400. The second imaging station 400 includes at least one second imaging device 404 suspended beneath the indexing transport table 202 by system support structure. In various embodiments, the second imaging device 404 is substantially identical in form and function to the first imaging device 304 of the first imaging station 300. The second imaging device 404 is mounted to the system support structure such that a field of view of the second imaging device 404 includes the transparent bottom of the seed tray 14 positioned adjacent the second imaging station 300. That is, the second imaging device 404 is positioned such that the second imaging device 404 can collect image data of the transparent bottom of loaded seed tray 14, and more particularly, image data of the bottom portion of each seed in the loaded seed tray 14. Accordingly, the second imaging device 404 can also be referred to herein as the bottom imaging device 404. As used herein, reference to the bottom portion of the seed(s) refers to the portion of the seed(s) that is facing downward with respect to the orientation of each seed within the respective seed tray well 30. That is, as used herein, the bottom portion of the seed(s) refers to the portion of the seed(s) generally facing toward, and generally resting on, the transparent bottom of each respective seed tray well 30, and does not refer to the independent structure or anatomy of the seed(s). The image data collected at the second imaging station 400 is transmitted to the main controller system 600 for storage and analysis, as described below.

As with the first imaging device 304, the second imaging device 404 can be any suitable imaging device selected in accordance with the imaging goals of seed sorter system 10. For example, in connection with an analysis for external seed coat damage, the second imaging device 404 may comprise a digital camera operable in the visible light range. Alternatively, for internal seed analysis, the second imaging device 404 may comprise a camera operable in the near infra-red light range (see, U.S. Pat. No. 6,646,264, the disclosure of which is hereby incorporated by reference). Still further, the second imaging device 404 may implement NMR/MRI imaging techniques (see, U.S. Pat. No. 7,367,155, the disclosure of which is hereby incorporated by reference).

In various embodiments, the second imaging station 400 additionally includes at least one second, or bottom, multi-spectral high-speed filter device 408, i.e., one additional multi-spectral high-speed filter device 408 for each additional imaging device 404. In various embodiments, the second multi-spectral high-speed filter device 408 is substantially identical in form and function to the first multi-spectral high-speed filter device 308 of the first imaging station 300. The second filter device 408 is positioned between the lens of the second imaging device 404 and the respective loaded seed tray 14 adjacent the second imaging station 400. The second multi-spectral high-speed filter device 408 includes a plurality of spectral filters that filter various wavelengths of light such that image data for each of the seeds in the loaded seed tray 14 can be collected at various spectral wavelengths. For example, in various embodiments, the second multi-spectral high-speed filter device 408 can be structured to include a filter wheel including at least six band pass filters to provide at least six different bands, i.e., wavelength bands, of spectral filtering. Accordingly, the second imaging device 404 and second filter device 408 can cooperatively operate to collect multi-spectral image data of the bottom portion of loaded seed tray 14 adjacent the second imagine station 400 and each seed therein at a plurality of different spectral wavelengths The second imaging station 400 further includes one or more second, or bottom, light sources 412 for illuminating the field of view of the second imaging device 404, i.e., the bottom portion of loaded seed tray 14 adjacent the second imaging station 400. In various embodiments, the second light source 412 is mounted, via system support structure, to illuminate the respective seed tray 14 at a specifically calibrated angle. Thus, the second imaging station 400 collects image data of the bottom portion of the seeds in the respective seed tray 14 using a particular illumination angle and at a plurality, e.g., at least six, different spectral wavelengths. As described in detail below, the second imaging device 404 transmits the collected image data for each illumination angle and each wavelength to the main controller system 600 for storage and analysis.

As with the first light sources 312, the second light source 412 can be any type of light suited for the particular imaging application of the seed sorter system 10. For example, the second light sources 412 can be an incandescent light, fluorescent light, ultraviolet light, infrared light, etc. In various embodiments, the first light source 412 is an incandescent light.

In various embodiments, the second imaging station 400 includes a second black background plate 416 suspended by system support structure above the indexing table platform 204. More specifically, the second background plate 416 is positioned such that, upon each advancement of the indexing table platform 204, the seed tray cut-out 216 positioned adjacent the first imaging station 300 and the respective transparent bottom seed tray 14 therein is directly below the second background plate 416. The second background plate 416 provides a solid dark background for each respective transparent bottom seed tray 14 during imaging of the bottom portion of the respective seed tray 14 and seeds retained within the wells 30.

The image data collected by the second imaging device 404 includes data relating to the seed tray 14 and to the seeds retained in each well 30 of the seed tray 14. The image data is transmitted to the main controller system 600 and stored (at least temporarily) in an electronic data storage device of the main controller system 600. The main controller system 600 analyzes the data to correlate each seed in the seed tray 14 to the specific, corresponding well 30 location within the seed tray 14. Accordingly, all the collected image data, i.e., all the image data from the second imaging device 404 at the particular illumination angle and each filtered wavelength, is analyzed and parsed to correlate the image data for each individual seed to the particular well 30 in which the respective seed is retained. In this way, a link exists between each seed, the corresponding well 30 and the corresponding image data.

The image data collected at the first and second imaging stations 300 and 400 can be processed in a number of known ways to identify seed characteristics or phenotypic traits (for example, as described in U.S. Pat. No. 6,646,264 or US 2006/0112628 referenced above). For example, image data analysis can reveal characteristic information of the individual seeds concerning, for example, the presence/absence of bio-chemical traits (like oil content), the presence or absence of damage, the presence or absence of disease, size, color, shape and the like. This characteristic information is obtained by processing the image data using custom algorithms executed on the data by the main controller system 600. The results of this processing are then stored in correlation with particular seeds, and more specifically, in correlation with the well 30 locations of each seed. In this way, a link exists between the image data and characteristic information of each seed.

As described further below, in various embodiments, the main controller system 600 executes various algorithms to perform multi-spectral multi-variate analysis on the image data for each seed to determine specific surface color traits of each respective seed. For example, in various embodiments, the seeds may comprise corn seeds for doubled haploid breeding wherein diploid seeds have a blue anthocyanin marker in the germ area. Multi-spectral multi-variate analysis can be performed on the image data for each corn seed to determine if each individual corn seed has the blue marker. The seeds determined to have the blue marker are therefore identified as diploid seeds, seeds in which the blue marker is absent are identified as haploid seeds, and seeds in which it is uncertain whether the blue marker is present are identified as undetermined. The identified characteristics for each seed, or lack thereof, can then be applied by the main controller system 600 against certain seed sorting criteria in order to effectuate the sorting of the seeds by characteristic, as described below.

Figure 7A:
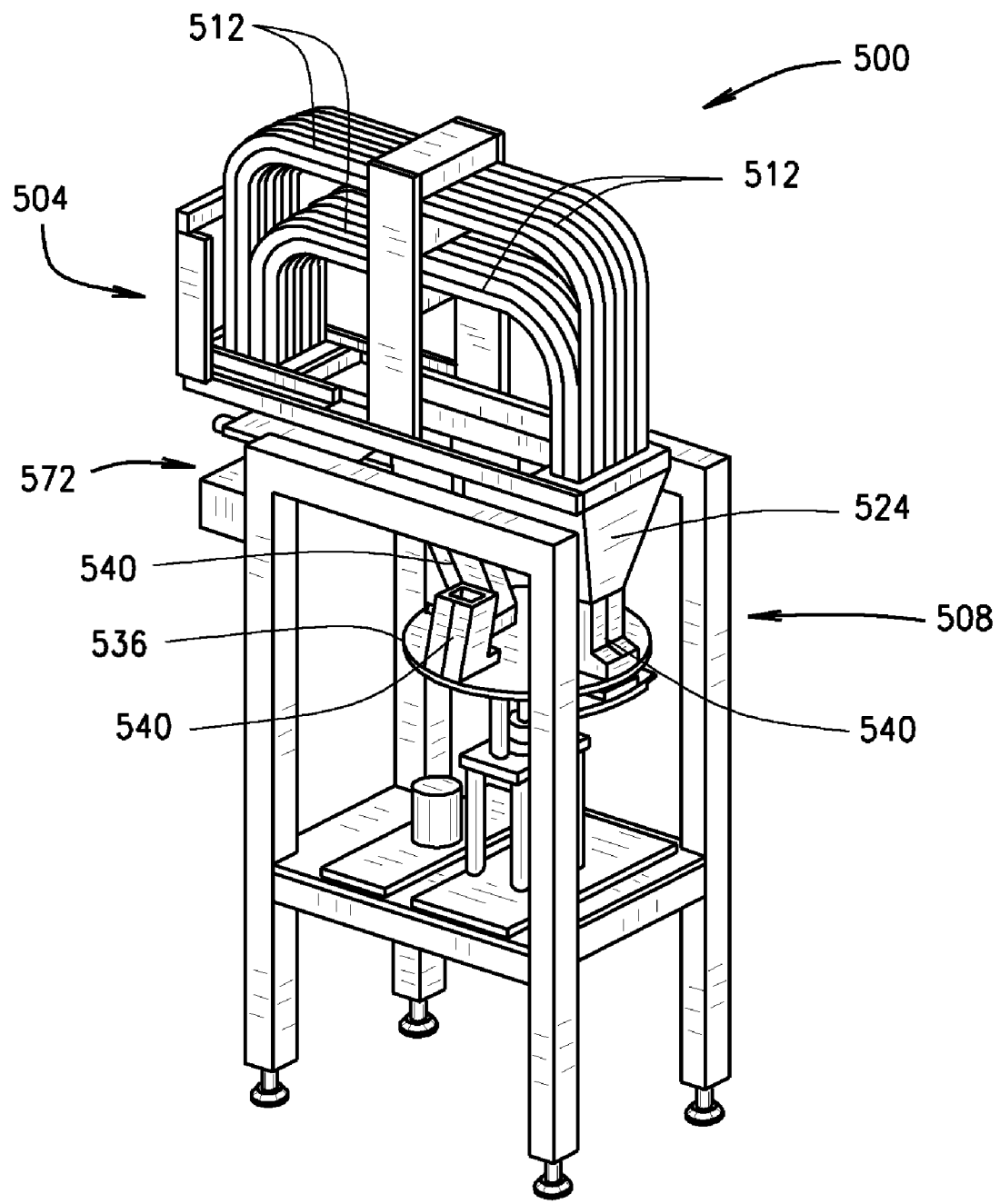
FIG. 7A is an isometric view of an off-loading station of the seed sorter system shown in FIG. 2A, in accordance with various embodiments of the present disclosure.
Figure 7B:
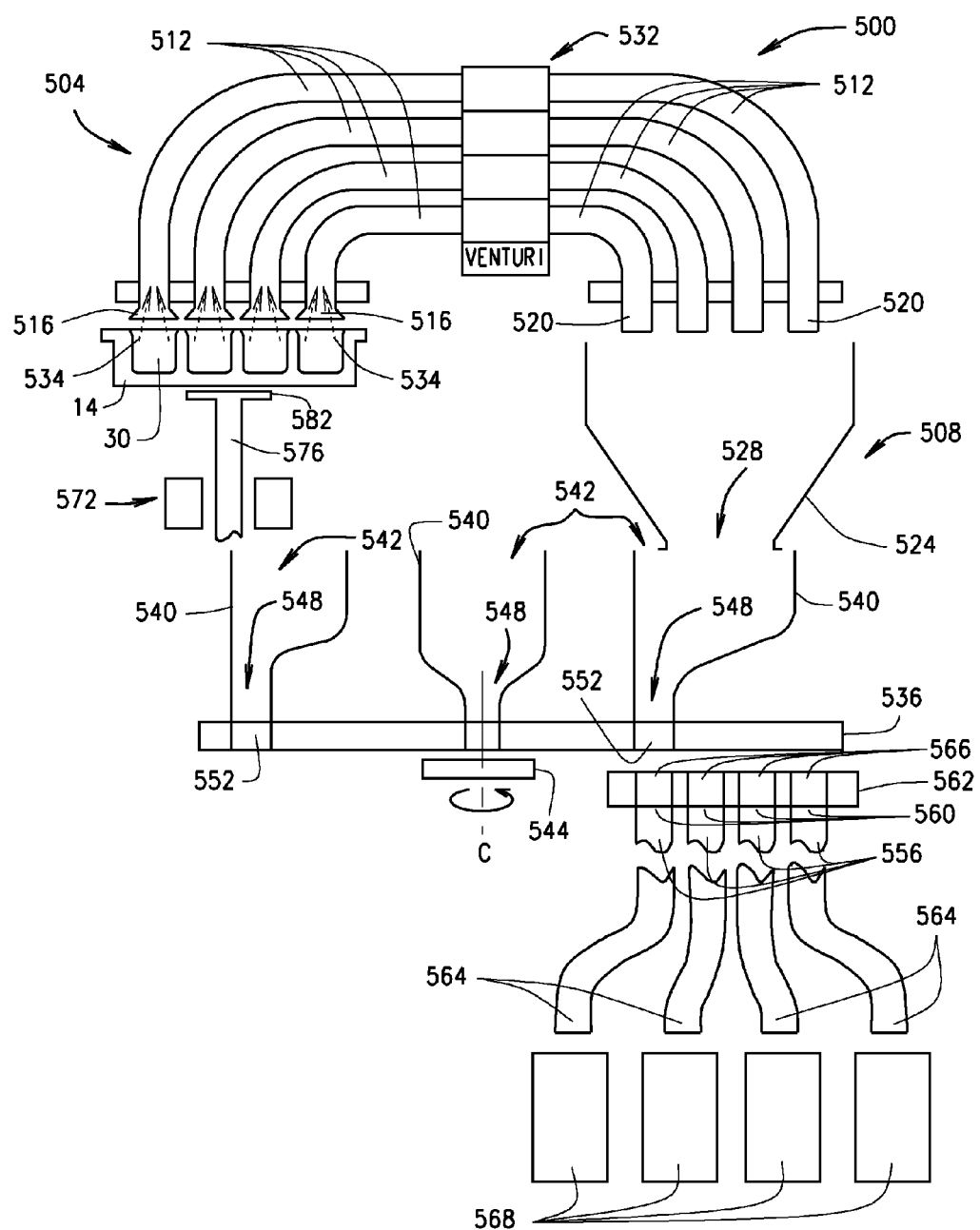
FIG. 7B is a schematic side view of the off-loading station shown in FIG. 7A.

Referring now to FIGS. 2A, 7A and 7B, the off-load and sort station 500 includes an off-loading subsystem 504 and a sorting subsystem 508. The off-loading subsystem 504 removes the seeds from the seed trays 14 after image collection at the first and second imaging stations 300 and 400 and transports the seed to a sorting subsystem 508. The sorting subsystem sorts each seed based on particular identified phenotypes, i.e., traits or characteristics, of the respective seed and deposits each seed in a corresponding collection receptacle (not shown).

The off-loading subsystem 504 includes a plurality of selectively actuable suction tubes 512. Each suction tube 512 includes a first end 516 positioned by a system support structure over a corresponding well 30 in a seed tray 14 that has been positioned underneath the first ends 516 of suction tubes 512 by successive advancement of the indexing table platform 204. In various embodiments, the plurality of suction tube first ends 516 are arranged in an array having a number and arrangement that corresponds to the number and arrangement of the wells 30 in the seed tray 14. In this way, one seed tray 14 can be fully unloaded using a single actuation of the off-loading subsystem 504 without having to engage in any positional adjustment of the subsystems. In other embodiments, an even submultiple arrangement of the suction tube first ends 516, with an appropriate x-y translation stage such as discussed earlier for loading the seed trays 14, can be used for unloading and sorting. Each suction tube 512 additionally includes a second end 520 positioned by system support structure over a collection funnel 524 having downwardly sloped sides that terminate at an opening 528. At about a midpoint of each suction tube 512 is positioned a Venturi block 523 that is controlled by the main controller system 600 to selectively draw a suction, or vacuum, 534 at the first ends 516 of the suction tubes 512.

The sorting subsystem 508 includes a rotatable turntable 536 that is positioned generally underneath the funnel opening 528. The top surface of the turntable 536 supports placement of a plurality of individual sorting guides 540. More specifically, the rotatable turntable 536 is positioned beneath the collection funnel 524 such that upper open ends 542 of the sorting guides 540 can be selectively located, through appropriate rotation of the turntable 536, directly under the funnel opening 528. Movement of the turntable 536 is effectuated through the use of a motor 544 (e.g., a stepper-type motor) controlled by the main controller system 600. Each sorting guide 540 additionally includes a lower open end 548 that aligns with a corresponding hole 552 in the turntable 536. Each individual hole 552 and corresponding sorting guide lower open end 548 is located a different radial distance from an axial center C of the turntable 536.

The sorting subsystem 508 additionally includes a plurality of diverter tubes 556 that are positioned beneath the turntable 536 via system support structure. More particularly, each of the diverter tubes 556 includes a receiving end 560 coupled to a manifold 562 such that each receiving end 560 aligns with a separate one of a plurality of apertures 566 in the manifold. Each manifold aperture 566 is located a different radial distance from the turntable axial center C that corresponds to a respective one of the holes 548 in the turntable 536. Thus, as the turntable rotates to align the upper open end 542 of a particular sorting guide 540 with the collection funnel opening 528, the respective sorting guide lower open end 548 and associated turntable hole 552, align with the aperture 566 and corresponding receiving end 560 of a specific one of the diverter tubes 556. A disposition end 564 of each diverter tube 556 terminates at a specific one of the repositories 18 (shown in FIG. 2B). For example, in various embodiments, the disposition end 564 of each diverter tube 556 can terminate at a specific one of a plurality of removable, replaceable seed repositories 568 (shown in FIG. 7B).

The sorting subsystem 508 further includes a seed tray lifting mechanism 572 that includes a linear air piston 576 that is generally located in alignment with the location of the arrayed suction tube first ends 516. More specifically, the piston 576 is located such that a platform end 582 of the piston 576 is aligned with a center of each of the indexing table seed tray cut-outs 216 as each respective loaded seed tray 14 is successively positioned adjacent the off-load and sort station 500. The piston 576 is controlled by the main controller system 600 to linearly move the piston 576 between a retracted position and an extended position. When moving from the retracted position to the extended position, the platform end 582 of the piston 576 passes through the indexing table platform cut-out 216 and contacts the transparent bottom of respective seed tray 14 held therein. The piston 576 then continues to extend to raise the seed tray 14 above the top surface of the indexing table platform 204. When the piston is fully extended, the respective seed tray 14 resting on the piston platform end 582, is located in alignment with and in close proximity to, or in contact with, the arrayed suction tube first ends 516. The seeds are then selectively removed from the respective seed tray 14 and selectively sorted to one of the seed repositories.

More particularly, prior to each seed being selectively removed from the raised seed tray 14, the main controller system 600 determines which seed or seeds is the next to be removed. The main controller system 600 rotates the turntable 536 to move a selected one of the sorting guides 540 into position under the funnel opening 528. Selection of which sorting guide 540 to position under the funnel opening 528 is based on which seed repository 568 the next to be removed seed or seeds is/are to be deposited into. Accordingly, the main controller system 600 will position under the funnel opening 528 the particular sorting guide 540 having the lower open end 548 that aligns with diverter tube 556 that terminates in the selected seed repository 568.

The main controller system 600 then selectively actuates one or more of the Venturi blocks 523 associated with the one or more suction tubes 512 having the respective first ends 516 positioned over, or in contact with, the wells 30 holding the seeds selected to be removed and sorted. Actuation of the Venturi block(s) 523 causes a suction to be drawn at the first end(s) 516 of the suction tube(s) 512 which draws the selected seed(s) into the respective suction tube(s) 512. Under the Venturi/suction forces, the captured seed is conveyed by an air stream through the suction tube(s) 512 to the second end(s) 520 where the seed(s) is/are deposited into the collection funnel 524. Gravity then causes the seed(s) to fall through the collection funnel opening 528 and into the selectively positioned sorting guide 540. Gravity then causes the seed(s) to fall through the respective sorting guide 540 and manifold 562 into the corresponding diverter tube 556, where the seed (s) then fall into the selected seed repository 568. The process then repeats by selectively positioning the sorting guides 540 into position under the funnel opening 528 and selectively actuating the Venturi block(s) 532 to remove selected seeds from the seed tray wells 30 and deposit the seeds into the proper seed repositories 568.

Thus, the seed sorting system 10 identifies whether each seed deposited into the bulk seed hopper 104 exhibits a particular phenotype and sorts the seeds to the seed repositories 568 based on the identified phenotype. Once the seeds are removed and sorted, the piston 576 returns to the retracted position, thereby returning the now empty seed tray 14 to respective indexing table seed tray cut-outs 216. The seed tray 14 is then available for subsequent loading of seeds, as described above, when the indexing table 202 is advanced to position the seed tray 14 adjacent the loading station 100.

Analysis of the multi-spectral image data collected at the first and second imaging stations to identify particular phenotypes of each seed will now be described. As set forth above, the seeds are selectively removed from the seed trays 14 and selectively sorted to the seed repositories based on the particular phenotype of each seed, as determined by analysis of the image data collected at the first and second imaging stations 300 and 400. More specifically, the main controller system 600 analyzes the image data collected at the first and second imaging stations 300 and 400 to determine particular phenotype(s) of each seed, and then controls the operation of the off-load and sort station 500 to selectively sort the seeds into the seed repositories 568.

In various embodiments, the main controller system 600 has stored therein various programs and/or algorithms executable to perform multi-spectral, multi-variate analysis on the image data collected at the first and second imaging stations 300 and 400. Using multi-variate techniques to analyze the multi-spectral image data provides identification of particular phenotype(s) for each seed in each well 30 of each seed tray 14. Each seed is then sorted to the proper seed repository 568 at the off-load and sort station 500 based on the particular phenotype(s) identified and linked to each respective seed.

Referring now to FIGS. 8, 9 and 10A-10F, an exemplary description of the operation of the seed sorting system 10, in accordance with the various embodiments illustrated in FIGS. 1 through 7B, will now be described. As described above, the seed sorting system 10 includes the seed loading station 100, the first imaging station 300, the second imaging station 400 and the off-load and sort station 500. For ease of illustration, the indexing table platform 204 is shown retaining eight seed trays 14. However, it will be understood that the indexing table platform 204 can be structured to retain more than or less than eight seed trays 14 with an appropriately sized design.

Initially, one or more empty seed trays 14 are retained on or in the indexing table platform 204, such that one of the seed trays 14 is positioned adjacent the seed loading station 100. For simplicity and clarity, the following exemplary description of the operation of the seed sorter system 10 will refer only to the seed tray 14 initially positioned adjacent the seed loading station 100. Additionally, for clarity, the seed tray 14 that is initially positioned adjacent the seed loading station 100 will be referred to in this example as seed tray 14'.

Figure 9:
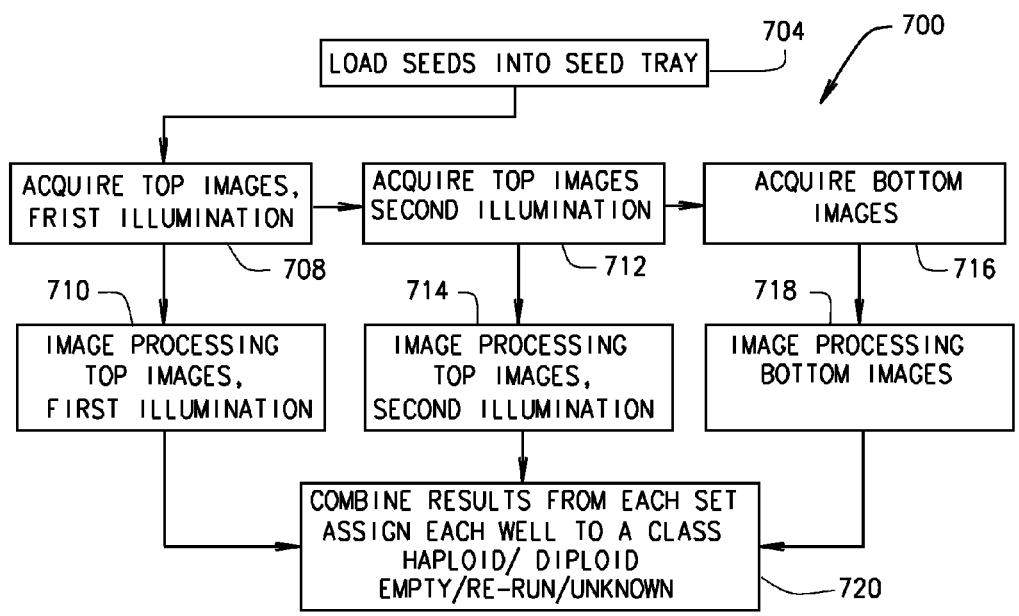
FIG. 9 is a flow chart illustrating an exemplary overview of the operation of the seed sorter system shown in FIG. 2A, in accordance with various embodiments of the present disclosure.
Figure 10A:
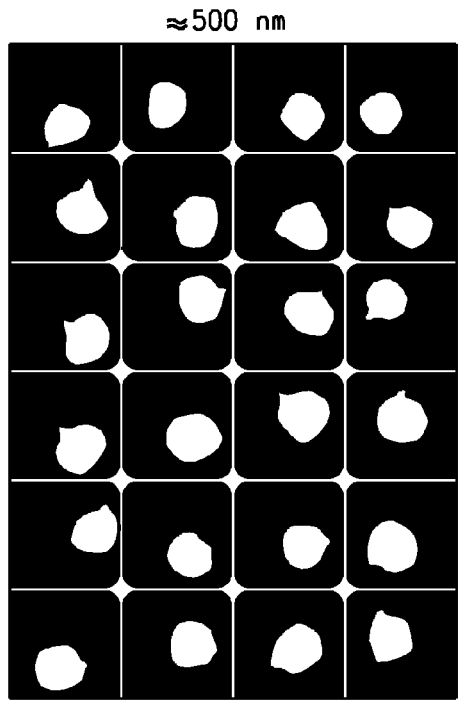
FIGS. 10A-10F are exemplary illustrations of images collected of a single tray of seeds, at various spectral bandwidths, using the seed sorter system shown in FIG. 1.
Figure 10B:
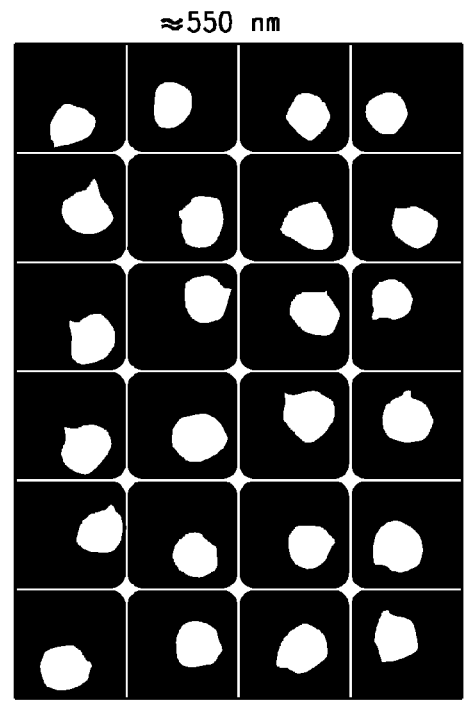
Figure 10C:
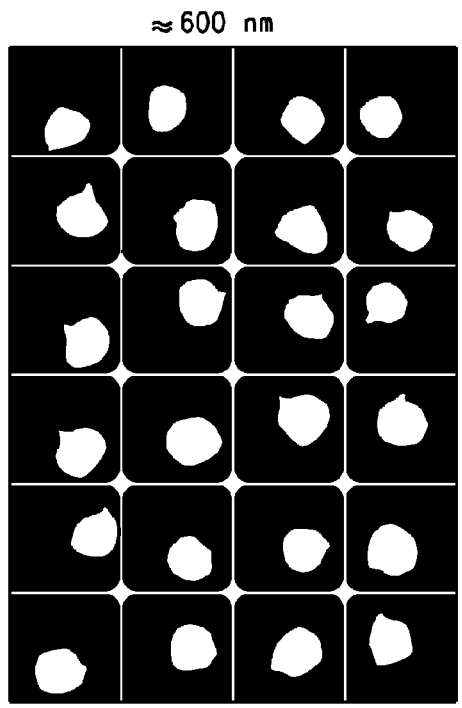
Figure 10D:
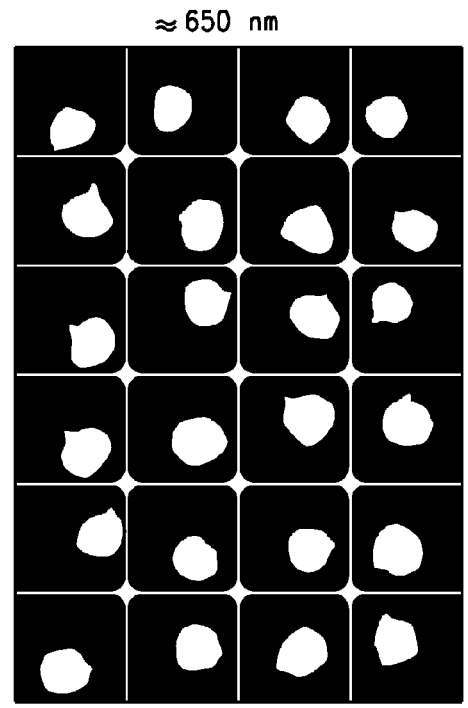
Figures 10E, 10F:
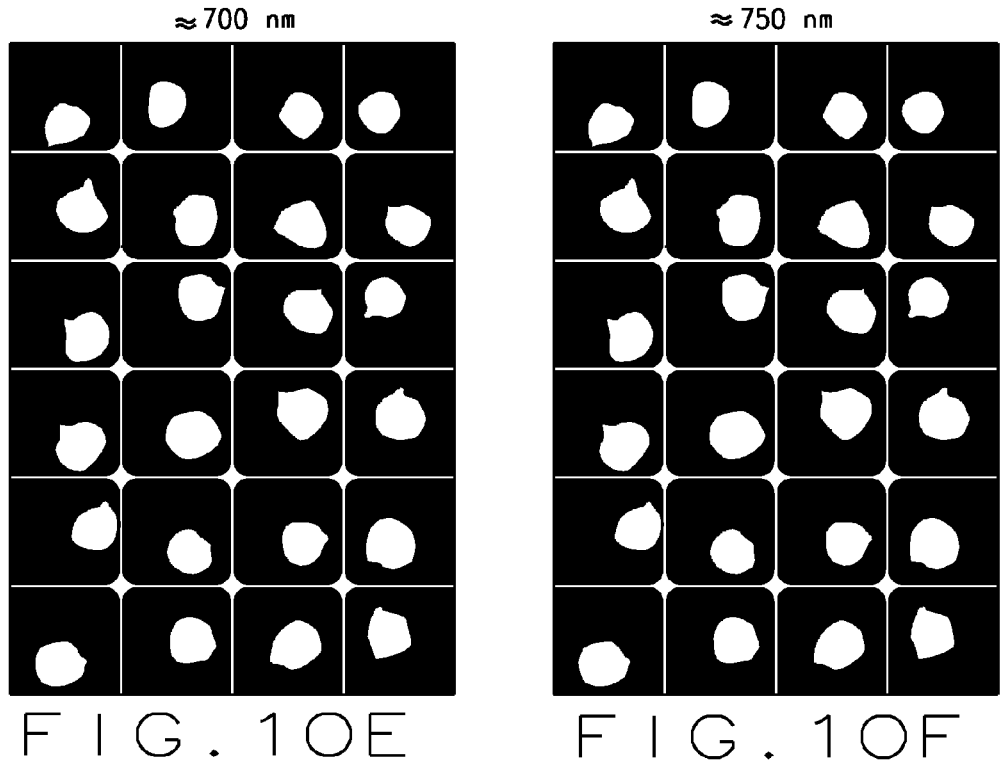
Figure 11:
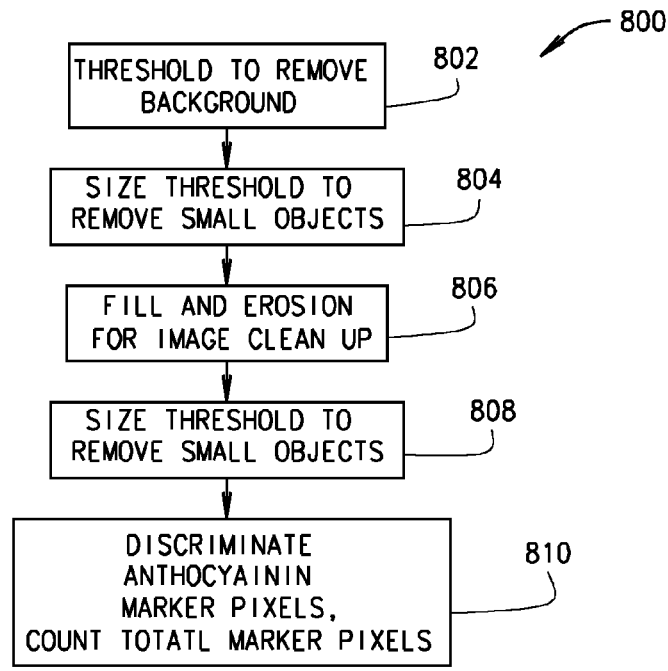
FIG. 11 is flow chart illustrating an overview of an exemplary image analysis process executed by a central controller system of the seed sorter system, shown in FIG. 2A, to classify and sort the seeds imaged by the seed sorter system, in accordance with various embodiments of the present disclosure.

FIG. 9 provides a seed sorter system flow chart 700. As indicated at 704, once the seed tray 14' is retained adjacent the seed loading station 100, the seed loading station 100 loads a single seed into each of the wells 30 of the seed tray 14' as described above. Following completion of the loading operation, the loaded seed tray 14' is sequentially conveyed by one or more advancements of the indexing transport table 202 to a position adjacent the first imaging station 300. The first imaging station 300 then acquires and processes multiple images of the top portion of the seed tray 14' and the seeds contained therein. For example, the first imaging station 300 can collect and transmit to the main controller system 600, images of the top portion of the seeds and seed tray 14' through each of six band pass filters of the first filter device 308 using light from only a first one of the first light sources 312, as indicated at 708. FIGS. 10A-10F are exemplary illustrations of six images that can be collected through the six band pass filters of the first filter device 308 using light from only the first one of the light sources 312. Next, a second set of six images can be collected through the six band pass filters of the first filter device 308 using only a second one of the light sources 312, as indicated at 712. The second set of six images would be similar to those shown in FIGS. 10A-10F, only the images would be collected using the second one of the light sources 312. As the second set of six images are being collected and transmitted to the main controller system 600, the main controller system 600 processes, i.e., analyzes the first set of six images of the top portion of the seeds and seed tray 14', as indicated at 710.

The indexing transport table 202 then sequentially advances the seeds and seed tray 14' to a position adjacent the second imaging station 400, where a third set of images are acquired. More particularly, the second imaging station 400 collects a third set of images including multiple images of the bottom portion of the seeds and seed tray 14' that are collected and transmitted to the main controller system 600. For example, the second imaging station 400 can collect images of the bottom portion of the seeds and seed tray 14' through six band pass filters of the first filter device 308 using light from the second light source 412, as indicated at 716. As the seeds and seed tray 14' are being advanced to the second imaging station 400, the main controller system 600 analyzes the second set of six images of the top portion of the seeds and seed tray 14', as indicated at 714.

After the third set of images, i.e., the images of the bottom portion of the seeds and seed tray 14', is collected and transmitted to the main controller system 600, the seeds and seed tray 14' are sequentially advanced to a position adjacent the off-load and sort station 500. As the seeds and seed tray 14' are being advanced to the off-load and sort station 500, the main controller system 600 processes the third set of images, as indicated at 718.

The processing, i.e., analyzing, of all the images of the top and bottom portions of the seeds and seed tray 14', e.g., the three sets of images, is described further below with reference to FIGS. 11 and 12A-12E. However, generally, the main controller system 600 analyzes each set of image data and then combines the results to determine whether each seed in the seed tray 14' possesses one or more desired phenotypes, i.e., characteristics and/or traits (such as, damage, disease, color, size, and the like), as indicated at 720. More specifically, each well 30 location, e.g., a column and a row, within the seed tray 14' is assigned one of a plurality of particular classes that indicate the class of each respective seed wherein, the class of each seed is determined based on the identified phenotype(s) of the respective seeds. For example, if analysis of the image data of a particular seed indicates that the germ of the seed has a blue marker, the well 30 location of that seed within the seed tray 14' can be flagged by the main controller system 600 as a diploid. Or, if analysis of the image data of a particular seed indicates that the germ of the seed is absent a blue marker, the well 30 location of that seed within the seed tray 14' can be flagged by the main controller system 600 as a haploid. Or, further yet, if analysis of the image data indicates that a well 30 location within the seed tray 14' does not contain a seed, that well 30 can be flagged by the main controller system 600 as empty. Or, still further yet, if analysis of the image data of a particular seed is inconclusive as to whether the germ of the seed has a blue marker, the well 30 location of that seed within the seed tray 14' can be flagged by the main controller system 600 as a unknown, indicating that the seed should be re-imaged and analyzed via the seed sorter system 10. Further yet, if the analysis indicates a blue marker, but the digital data does not overcome the threshold for a diploid, the well 30 location of that seed within the seed tray 14' can be flagged by the main controller system 600 as Re-Run, to reanalyze the seed, as described below.

By the time the indexing transport table 202 sequentially advances the seeds and seed tray 14' to a position adjacent the off-load and sort station 500, the main controller system 600 has assigned each well 30 in the seed tray 14' to one of the plurality of predetermined classes. The off-load and sort station 500 then removes the seeds from the seed tray 14' and sorts the seeds to a proper corresponding one of the seed repository 568, as described above. Each seed repository 568 is designated to receive only seeds identified to have a particular one of the predetermined classes. For example, all seeds removed from well 30 locations of seed tray 14' flagged as a haploid are selectively sorted to a seed repository 568 designated to receive only seeds identified as haploids, while another seed repository is designated to receive only seeds identified as diploids, and so on. This operation is repeated as many times as is needed to remove all seeds from the seed tray 14'. The empty seed tray 14' is then sequentially advanced by the indexing transport table 202 to the position adjacent the seed loading station 100, and the process with respect to seed tray 14' is repeated.

Figure 8:
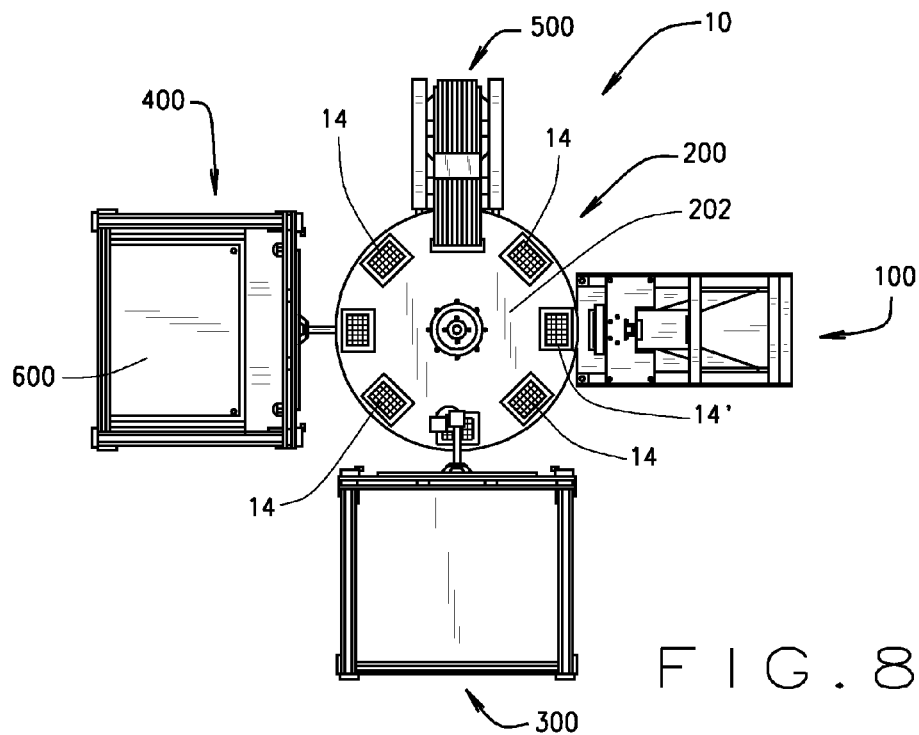
FIG. 8 is a top view of the seed sorter system shown in FIG. 2A.

Although the operation of the seed sorter system 10 has been described above with respect to a single seed tray 14', it will be understood that multiple seed trays 14 are handled simultaneously by the seed sorter system 10, thereby further increasing the throughput rate of the seed sorter system 10. For example, FIG. 8 illustrates simultaneous operation on eight seed trays 14. Accordingly, each of the seed loading station 100, the first imaging station 300, the second imaging station 400 and the off-load and sort station 500 are simultaneously active in performing their assigned task(s) with each rotational advancement of the indexing transport table 202. For example, while one seed tray 14 is being loaded with seeds by the seed loading station 100, previously loaded trays 14 (and the seeds therein) are being imaged, analyzed and sorted to the seed repositories 568 by the first and second imaging stations 300 and 400, and the off-load and sort station 500.

Referring now to FIGS. 11 and 12A-12D, FIG. 11 provides a flow chart 800 illustrating an exemplary analysis process executed by the main controller system 600 on the multi-spectral image data collected at the first and second imaging stations 300 and 400. As indicated at 710 of FIG. 9, while the first imaging station 300 is collecting the second set of images of a particular seed tray 14, the main controller system 600 analyzes the first set of multi-spectral image data.

Figure 12A:
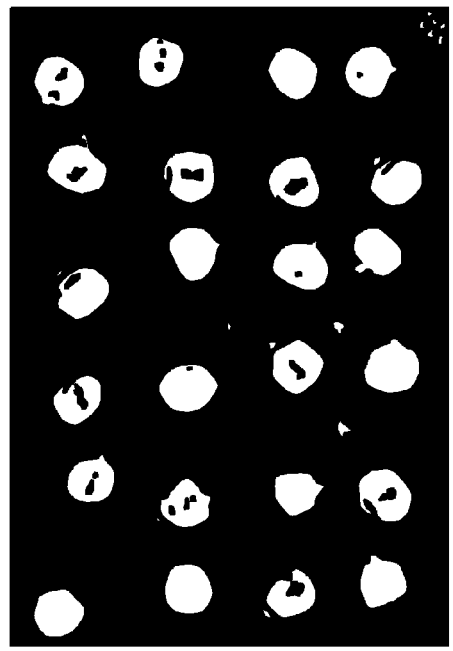

To analyze the first set of multi-spectral image data, the main controller system 600 first develops a background mask, and applies the background mask to the image data of each of the six images to remove approximately all the data points, e.g., pixels, that are considered to be background data, i.e., non-seed related data, as indicated at 802. An exemplary pictorial illustration of an image after the background mask has been applied as shown in FIG. 12A. In various embodiments, the background mask can be constructed using any one of the six images, e.g., the image with the best signal-to-noise ratio, to mathematically determine which data points represent background data.

Figure 12B:
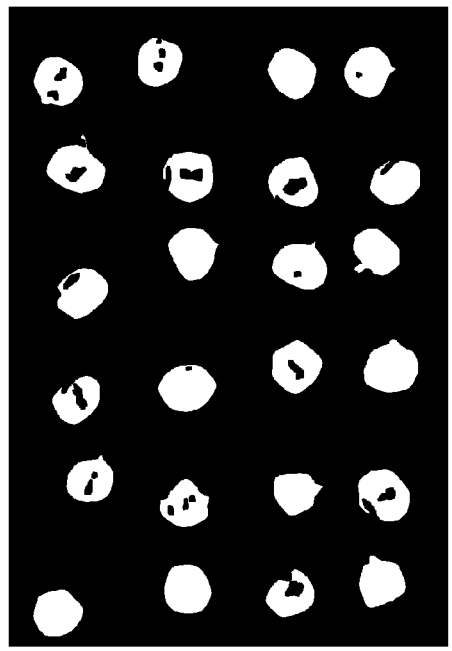

Next, the main controller system 600 applies a first size threshold mask to each of the six images to filter out any data remaining in each image that is too small to be a seed or a whole, in-tact seed, as indicated at 804. An exemplary pictorial illustration of an image after the background and first size threshold masks have been applied is shown in FIG. 12B. For example, noise along the edges or in the corners of each image may remain after the background mask is applied or parts of broken seeds can be present, or image data of the respective seed tray 14 may remain. Such extraneous data is removed by the first size threshold mask. In various embodiments, the first size threshold mask is predetermined based on known size parameters of the type of seeds being analyzed and sorted by the seed sorter system 10.

Figure 12C:
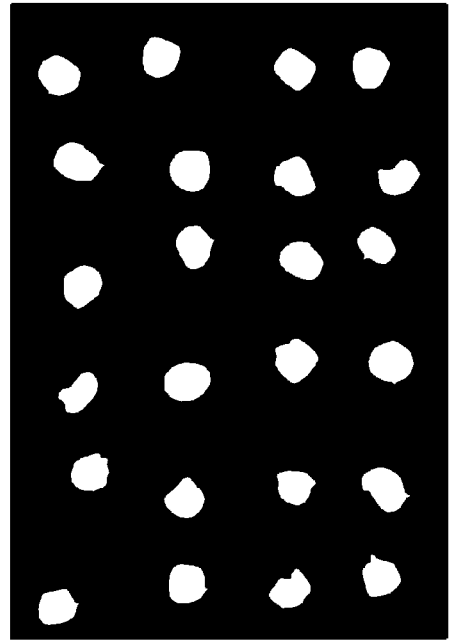

After the first size threshold mask is applied, the main controller system 600 applies a fill and erosion mask to each of the six images, as indicated at 806. The fill and erosion mask mathematically determines if the remaining image data of seed includes any 'dark' spots within each seed image. Such 'dark' spots can be present due to color contrast of each respective seed or shadows caused by the contour of each respective seed. The fill and erosion mask 'fills in' such dark spots and also fills or removes pixels around the edges of each seed image caused by such things as noise and/or background 'bleed-through'. Thus, the fill and erosion mask 'fills in' dark spots within each seed image and 'cleans up' the edges of each seed image. An exemplary pictorial illustration of an image after the background mask, the first size threshold mask and the fill and erosion mask has been applied is shown in FIG. 12C.

The erosion and fill mask can sometimes remove, or filter out, pixels such that the resulting image of a seed includes a large object and a much smaller object at the border of the seed. Therefore, the main controller system 600 applies a second size threshold mask to remove the smaller objects, as indicated at 808. In various embodiments, the second size threshold mask is predetermined based on known size parameters of the type of seeds being analyzed and sorted by the seed sorter system 10.

Thus, the background, first and second size threshold, and fill and erosion masks remove all data points, i.e., pixels, not related to one of the seeds in the respective seed tray 14 for each of the six images. The main controller system 600 then performs mathematical analysis on the six images to determine whether the remaining image data for each individual seed includes data indicative of a desired phenotype, as indicated at 810. The main controller system 600 can employ any mathematical analysis technique or process suitable to make such a determination. For example, in various embodiments, the main controller system 600 employs multivariate analysis to determine whether the remaining multi-spectral image data for each individual seed includes data indicative of an anthocyainin marker in the germ of the seed. More particularly, multivariate analysis is performed on each data point, or pixel, of the remaining multi-spectral image data for each seed to obtain a resultant value that is compared to a predetermined first threshold value. Whether the resultant value is above or below the first threshold is indicative of the desired phenotype, e.g., whether the pixel is indicative of an anthocyainin marker in the germ of the seed. The resultant values above the first threshold and/or below the first threshold are compiled to obtain a total number of resultant values above the first threshold and/or a total number of resultant values below the first threshold for the first set of multi-spectral images.

As indicated at 714 of FIG. 9, while the indexing transport table 202 is advancing the respective seed tray 14 to the second imaging station 400, the main controller system 600 analyzes the second set of multi-spectral image data. Particularly, the main controller system 600 analyzes the second set of multi-spectral image data in the same manner as described above with regard to analysis of the first set of multi-spectral image data. Thus, analysis of the second set of image data provides a second set of resultant values above the first threshold and/or a second set of resultant values below the first threshold.

Similarly, as indicated at 718 of FIG. 9, while the indexing transport table 202 is advancing the respective seed tray 14 to the off-load and sort station 500, the main controller system 600 analyzes the third set of multi-spectral image data. Particularly, the main controller system 600 analyzes the third set of multi-spectral image data in the same manner as described above with regard to analysis of the first and second sets of multi-spectral image data. Thus, analysis of the third set of image data provides a third set of resultant values above the first threshold and/or a third set of resultant values below the first threshold.

Once the main controller system 600 has analyzed the three sets of multi-spectral image data and generated the respective three sets of resultant values, the main controller system 600 sums the three sets of resultant values and compares the sum to a predetermined second threshold value. More specifically, the main controller system 600 combines the three sets of resultant values above the first threshold and/or combines the three sets of resultant values below the first threshold to obtain an aggregate sum of resultant values above the first threshold and/or an aggregate sum of resultant values below the first threshold. The aggregate sum of resultant values above the first threshold and/or the aggregate sum of resultant values below the first threshold are then compared to the second threshold in order to assign a class to the respective seed and well 30 in which the respective seed is retained, as described above. For example, if the aggregate sum of the resultant values is above the second threshold, the seed and corresponding well 30 are flagged as a diploid. But, if the aggregate sum of the resultant values is below the second threshold, the seed and corresponding well 30 are flagged as a haploid, and if the aggregate sum of the resultant values is equal to the second threshold, the seed and corresponding well 30 are flagged as an unknown. An exemplary table of results for a single seed tray 14 of seeds is shown in FIG. 12D. The main controller system 600 then controls the off-load and sort station 500 to off-load and sort the seeds from the respective seed tray 14 to the appropriate seed repositories based on the results of the comparison aggregate sums to the second threshold.

Figure 13A:
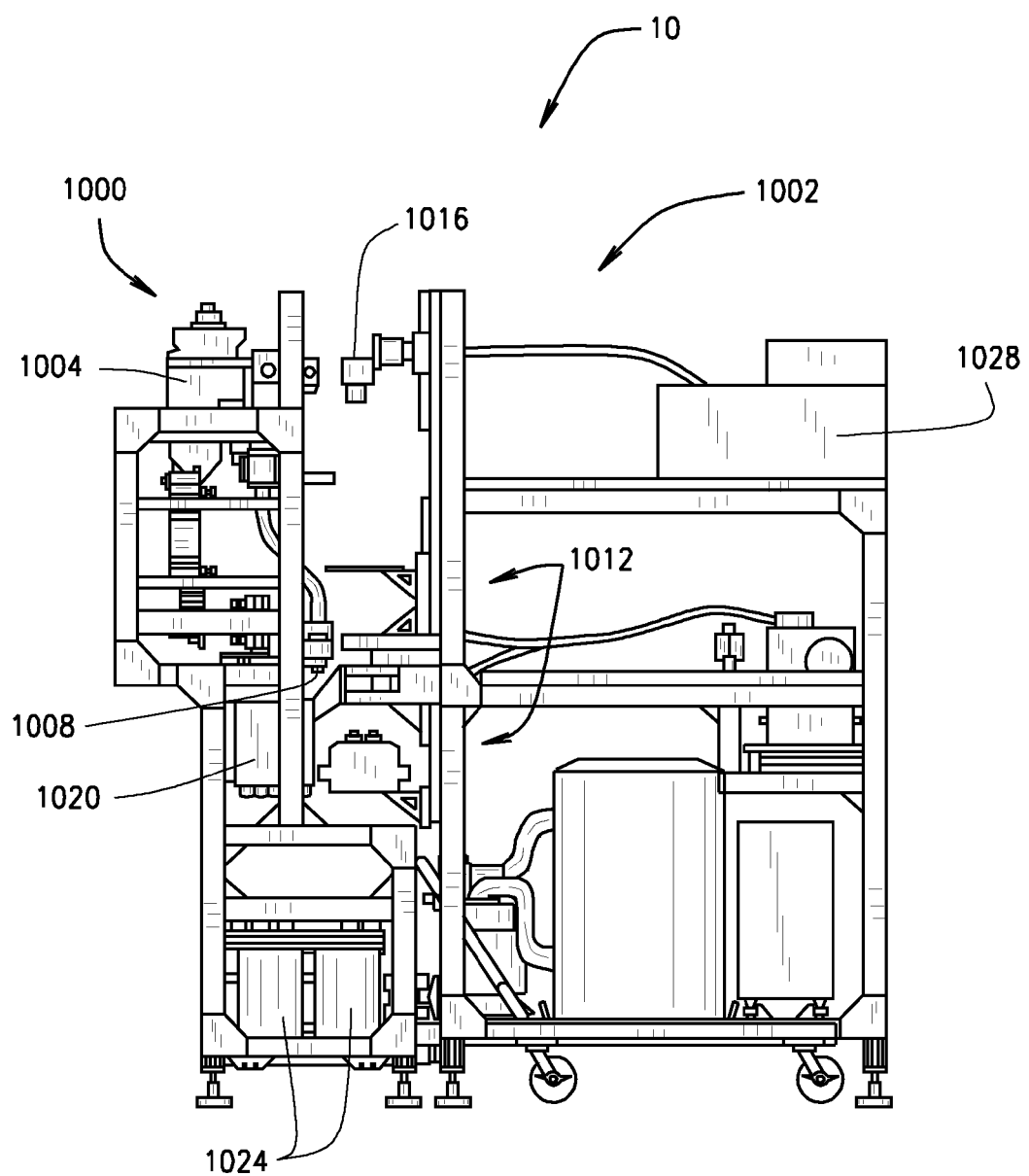
FIG. 13A is a side view of the seed sorter system shown in FIG. 1, in accordance with other various embodiments of the present disclosure.
Figure 13B:
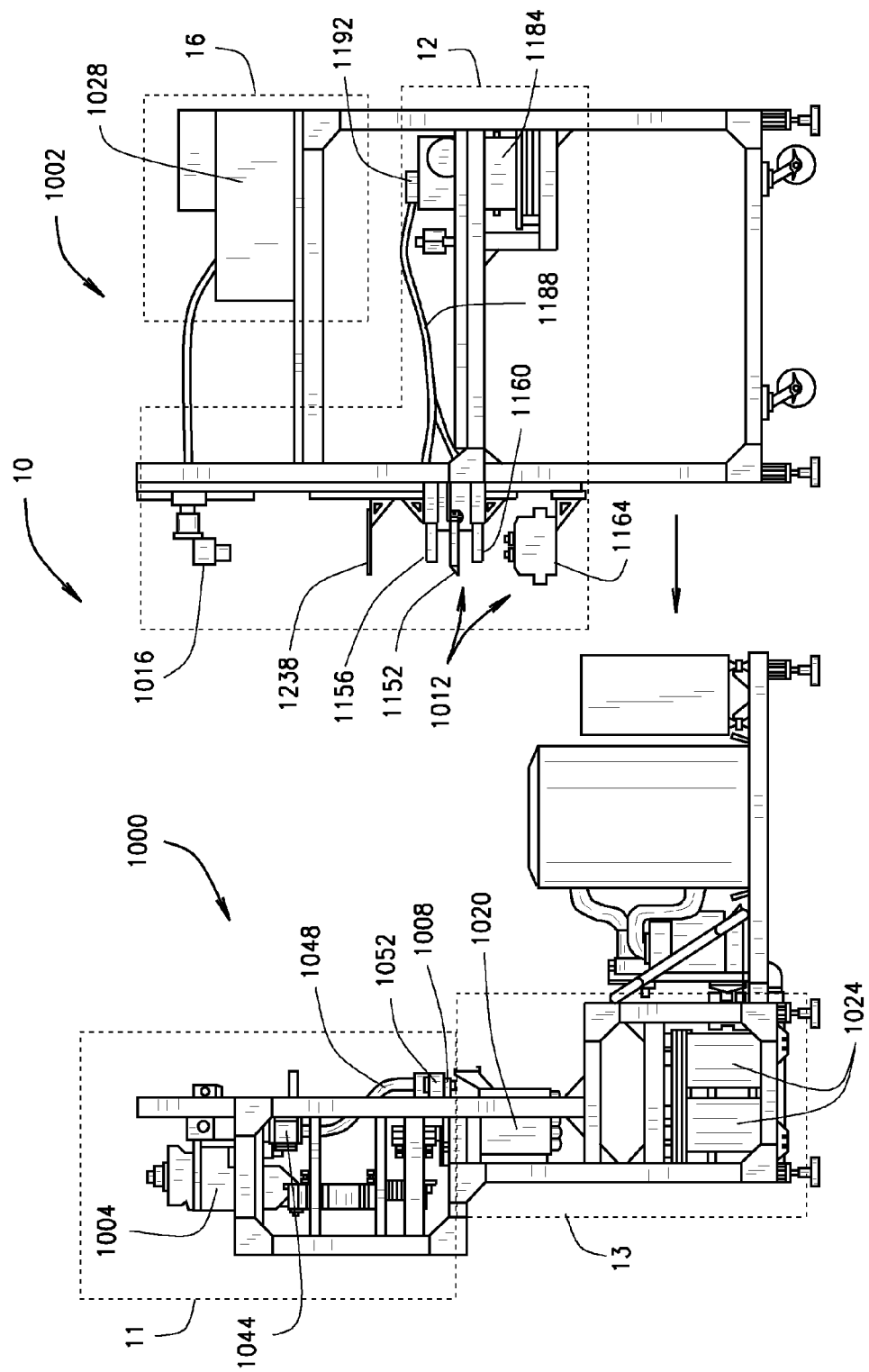
FIG. 13B is a side view of the seed sorter system shown in FIG. 13A separated into a first module and a second module, in accordance with various embodiments of the present disclosure.

Referring now to FIGS. 1, 13A and 13B, in various other embodiments the seed sorter system 10 can be a two station linear transport seed sorter system that includes a seed loading, transporting and sorting station 1000 and an optics and controller station 1002. In such embodiments, the seed loading, transporting and sorting station 1000 can include the L&T subsystem 11 and the OL&S subsystem 13, and the optics and controller station 1002 can include the I&A subsystem 12 and the central controller system 16. In such embodiments, the L&T subsystem generally includes a bulk seed hopper and singulator 1004 and a linear seed on-loader 1008, and the I&A subsystem generally includes an imaging theater, or subassembly, 1012 and one or more imaging devices 1016. Additionally, in such embodiments, the OL&S subsystem generally includes a plurality of imaged seed sorters 1020 and a plurality of seed repositories 1024, and the central controller system generally includes a main, or master, controller system 1028. In various embodiments, in order to avoid vibrations generated by the seed loading, transporting and sorting station 1000 from being transferred to the optics and controller station 1002, the seed loading, transporting and sorting station 1000 and the optics and controller station 1002 are assembled as separate structures that are placed adjacent each other, but not in contact with each other, to form the seed sorter system 10. Moreover, in various embodiments, one or both of the seed loading, transporting and sorting station 1000 and the optics and controller station 1002 can be mounted on wheels such that the respective stations 1000 and 1002 can be easily placed adjacent each other to form the seed sorter system 10.

Figure 14:
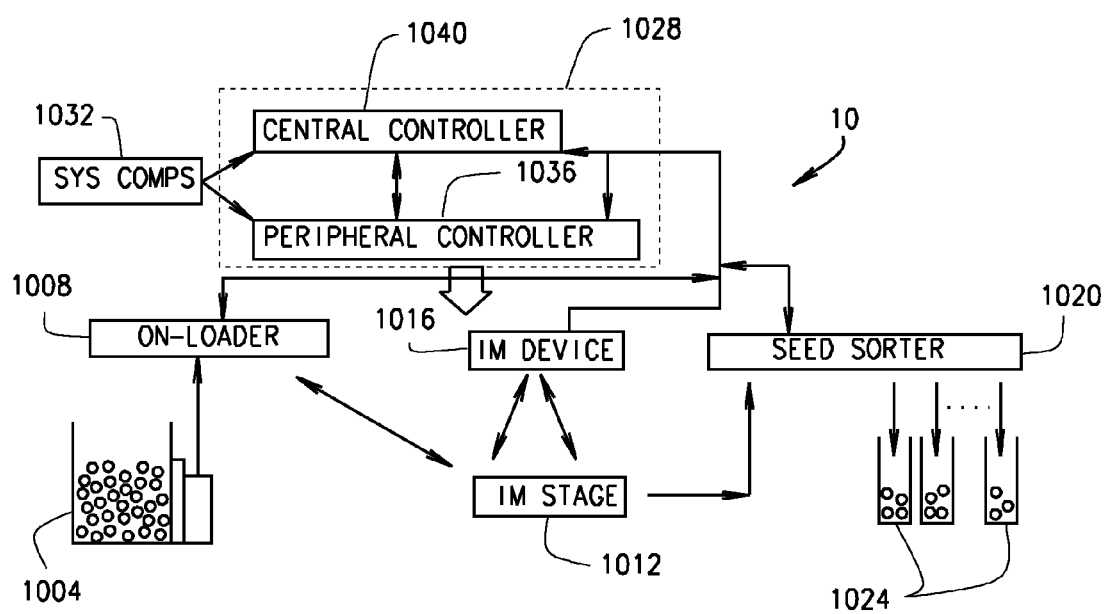
FIG. 14 is a functional block diagram of the seed sorting system shown in FIGS. 13A and 13B, in accordance with various embodiments of the present disclosure.

Referring to FIGS. 13A, 13B and 14, FIG. 14 illustrates a functional block diagram of the seed sorting system shown in FIGS. 13A and 13B, in accordance with various embodiments. Generally, in such embodiments, the seed sorter system 10 is structured and operable to isolate, i.e., singulate, a plurality of seeds utilizing the bulk seed hopper and singulator 1004. Each respective singulated seed is then transferred to the seed on-loader 1008 that transports and loads the singulated seeds on the imaging theater 1012. The seeds are retained on the imaging theater 1012 for imaging by the imaging device(s) 1016. As described further below, the imaging theater 1012, imaging device(s) 1016 and master controller system 1028 are structured and cooperatively operable to collect multiple images from a plurality of angles, or sides, of each seeds on the imaging theater 1012. The images collected can be any desirable type of images. For example, the images can be visual images, near infra-red (NIR) images or NMR/MRI images, or any other type images. In various embodiments, the imaging theater 1012, imaging device(s) 1016 and master controller system 1028 function to collect a plurality of digital images of each seed from a plurality of different viewing angles and at various spectral wavelengths, e.g., four to ten different spectral wavelengths.

As described further below, in various embodiments, the seed sorter system 10 illustrated and described with reference to FIGS. 1 and 13A through 20C, more particularly the master controller system 1028, can be structured and operable to implement multivariate analysis to analyze the image data of the multiple images collected via the I&A subsystem 12. Specifically, the multi-angle-view image data can be communicated to the master controller system 1028 where multivariate analysis is performed on the collected image data to identify whether each respective seed possesses one or more desired phenotypes, i.e., observable traits and/or characteristics. Further yet, each seed is off-loaded from imaging theater 1012 and sorted to a particular one of the seed repositories 1024, via the imaged seed sorters 1020, based on the identified phenotype of the respective seed as determined via the multivariate analysis.

The operation of the seed sorter system 10, as illustrated and described with reference to FIGS. 1 and 13A through 20C, is controlled and automated by the master controller system 1028 such that the operations performed by the L&T subsystem 11, the I&A subsystem 12 and the OL&S subsystem 13, occur substantially without need for human interaction, intervention or control. However, such actions as loading the seeds into the bulk seed hopper and singulator 1004 and/or physically manipulating and/or changing the seed repositories 1024 (either individually or collectively), and various other necessary hand setup and/or calibration can be performed manually with human participation.

Generally, in various embodiments, the master controller system 1028 can include one or more processors and/or microprocessors, and one or more electronic data storage devices utilized to store and execute various custom programs, applications and/or algorithms to effectuate the operation of the seed sorter system 10. Accordingly, the master controller system 1028 can comprise a specially programmed computer, or computer system, in communication with associated system devices that enable communication with and control the operations of the various stations, subsystems and corresponding components 1032 of the seed sorter system 10. Although the master controller system 1028 is exemplarily illustrated in FIG. 14 as a single unit, the master controller system 1028 can be a single computer based system or a plurality of computer based subsystems networked together to coordinate the simultaneous operations of the seed sorter system 10, as described herein. For example, in various embodiments, the master controller system 1028 can include a plurality of peripheral controller subsystems 1036, e.g., a peripheral controller subsystem 1036 for each of the seed loading, transporting and sorting station 1000 and the optics and controller station 1002. Each peripheral controller subsystem 1036 can include one or more processors, microprocessors and electronic data storage devices that effectuate communication with various seed sorter system components 1032, e.g., sensors, devices, mechanisms, motors, tools, etc., and are networked together with a central controller subsystem 1040 to cooperatively operate all the stations, systems and subsystems of the seed sampler system 10, as illustrated and described with reference to FIGS. 1 and 13A through 20C. Or, alternatively, the master controller system 1028 can comprise a single computer communicatively connected to all the various system components 1032 to cooperatively operate all the stations, systems and subsystems of the seed sampler system 10, as illustrated and described with reference to FIGS. 1 and 13A through 20C.

In addition to storing programming for controlling the operation of the seed sorter system 10, the electronic data storage device(s) (or other data storage functionality, not explicitly shown but inherently present) provided within the master controller system 1028 is used to store the collected images and related image data relating to each imaged seed in a database or other suitable format. Additionally, the data storage device(s) of the master controller system 1028 can also store location data received from, or derived in connection with controlling the operation of the OL&S subsystem 13 concerning the repositories 1024 where the seeds have been deposited. This location data is correlated in the database or other format with the image data on an individual seed-by-seed basis.

As described above, the master controller system 1028 communicates with various seed sorter system components 1032 that include various system sensors. The system sensors operate to detect conditions of interest during operation of the seed sorter system 10 and communicate that information to the master controller system 1028. With this information, the master controller system 1028 generates control commands that effectuate the operations and actions taken by the various stations, systems, subsystems and components of the seed sorter system 10. For example, the sensed condition information may concern: the successful singulating and loading of the seeds via the bulk seed hopper and singulator 1004 and the seed on-loader 1008; the sorting and deposition of each seed into the proper seed repository 1024 via the imaged seed sorters 1020; the status (for example, position, location, vacuum, pressure, and the like) of various component parts of the various subsystems 11, 12 and 13; operation, maintenance, performance, and error feedback from the various components of each subsystem 11, 12 and 13 (separate from, or perhaps comprising or in conjunction with, collected data); and the like. More specifically, sensor information that is collected and processed for use in controlling the operation of the seed sorter system 10 can include information like: device or component status; error signals; movement; stall; position; location; temperature; voltage; current; pressure; and the like, which can be monitored with respect to the operation of each of the stations, subsystems and associated components of the seed sorter system 10.

Figure 15A:
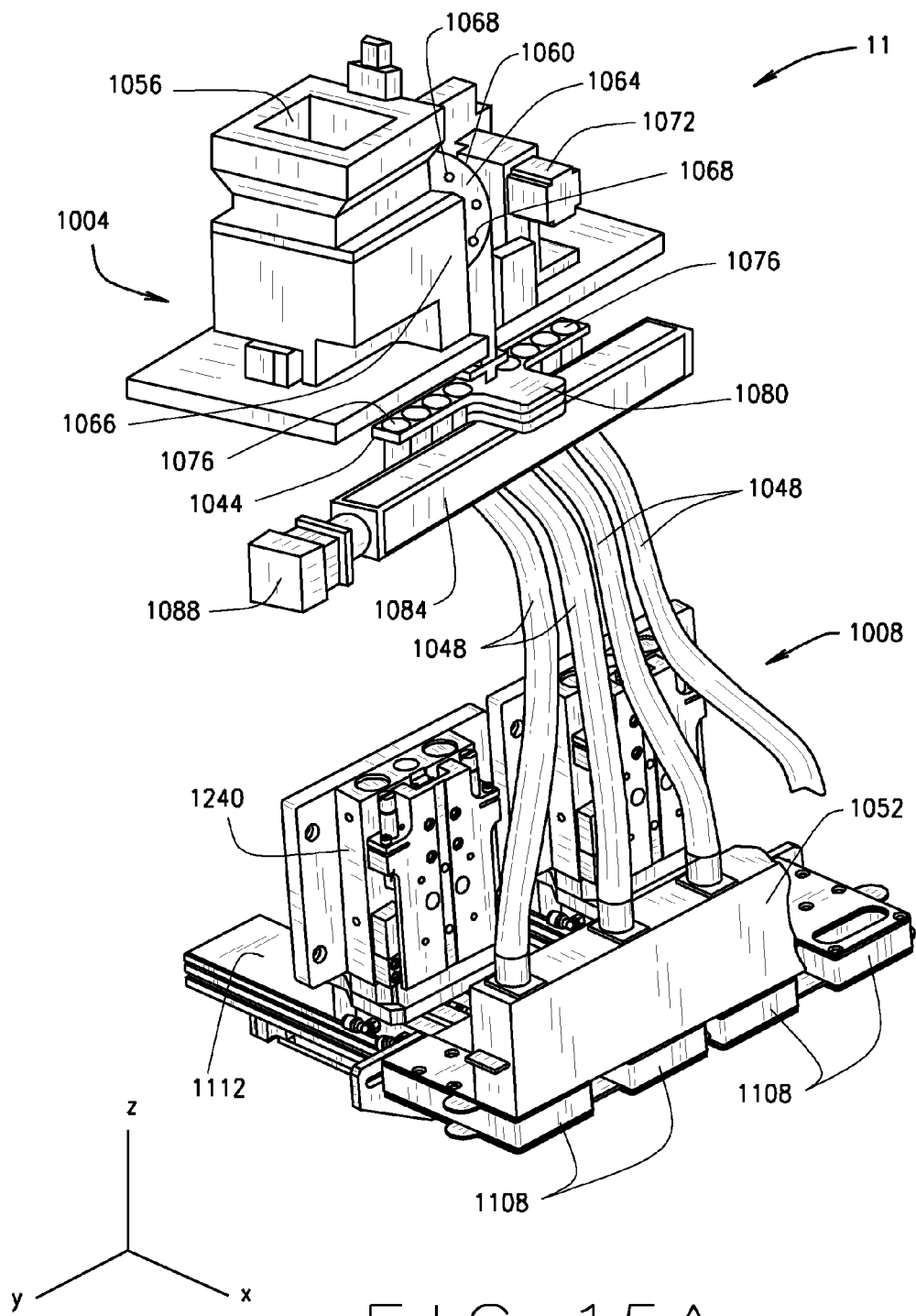
FIG. 15A is an isometric view of a load and transport subsystem of the seed sorter system shown in FIG. 13A, in accordance with various embodiments of the present disclosure.

Referring now to FIG. 15A, as described above, the L&T subsystem 11 generally includes the bulk seed hopper and singulator 1004 and the seed on-loader 1008. In various embodiments, the L&T subsystem additionally includes a tube shuttle 1044 for receiving singulated seeds and sequentially diverting each seed into a respective one of a plurality of first transfer tubes 1048 that terminate at an escapement assembly 1052.

Generally, the bulk seed hopper and singulator 1004 includes a bulk seed hopper 1056 and a singulating wheel 1060. The singulating wheel 1060 is mounted for rotation in a vertical plane such that a portion of the singulating wheel 1060 extends into an interior reservoir of the seed hopper 1056. Another portion of the singulating wheel 1060 extends outside of the seed hopper 1056 such that a face 1064 of the singulating wheel 1060 is positioned adjacent a seed collector 1066. The seed singulating wheel 1060 includes a plurality of spaced apart recessed ports 1068 that extend through the face 1064 and are communicatively coupled to a vacuum system (not shown) such that a vacuum can be provided at each of the recessed ports 1068.

To singulate the seeds, i.e., separate the seeds one at a time from the bulk seed hopper 1056, a plurality of seeds are placed in the interior reservoir the bulk seed hopper 1056. The singulating wheel 1060 is then rotated as a vacuum is provided to at least some of the recessed ports 1068, e.g., the recessed ports 1068 in the face 1064 of the portion of the singulating wheel 1060 extending into the interior reservoir of the seed hopper 1056. Particularly, the seed singulating wheel 1060 is incrementally rotated, via an indexing motor 1072, such that recessed ports 1068 sequentially rotate through the interior reservoir of the seed hopper 1056, out of the seed hopper 1056, and the past seed collector 1066 before re-entering the interior reservoir of the seed hopper 1056. As the singulating wheel 1060 incrementally rotates and the recessed ports 1068 incrementally pass through the seed hopper 1056 interior reservoir, individual seeds are picked up and held at each recessed port 1068 by the vacuum provided at the respective recessed ports 1068. As the singulating wheel 1060 incrementally rotates, the seeds are carried out of the seed hopper 1056 to the seed collector 1066 where each seed is removed from the face 1064 of the singulating wheel 1060.

In various embodiments, the seed collector 1066 includes a wiper (not shown) that physically dislodges each seed from the respective recessed port 1068 as the singulating wheel 1060 incrementally rotates past the seed collector 1066.

Alternatively, in various other embodiments, each seed can be released from respective recessed port 1068 by temporarily terminating the vacuum at each individual recessed port 1068 as the individual recessed port 1068 is positioned adjacent the seed collector 1066. In still other embodiments, each seed can be blown from the respective recessed port 1068 by temporarily providing forced air at each individual recessed port 1068 as the individual recessed port 1068 is positioned adjacent the seed collector 1066.

After each seed is removed from the singulating wheel 1060, the seeds are funneled sequentially into each of the first transfer tubes 1048 having proximal ends connected to openings 1076 in a tube shuttle 1044. The tube shuttle 1044 is mounted to a carriage 1080 that is movably mounted to a linear translation stage 1084 that includes an actuator 1088 controllable by the master controller system 1028 to bi-directionally move the carriage 1080, tube shuttle 1044 and proximal ends of the first transfer tubes 1048 along the translation stage 1084. Therefore, as each seed is removed from the singulating wheel 1060, the seed is funneled into one of the first transfer tubes 1048. The master controller system 1028 then moves the tube shuttle 1044 along the translation stage 1084 such that a subsequent first transfer tube 126 will receive the next seed removed from the singulating wheel 1060. As each seed is removed from the singulating wheel 1060 and deposited into a respective first transfer tube 126, each seed passes through the respective first transfer tube 126, via gravity, vacuum or forced air, to the escapement assembly 1052 to which a distal end of each first transfer tube is connected.

Figure 15B:
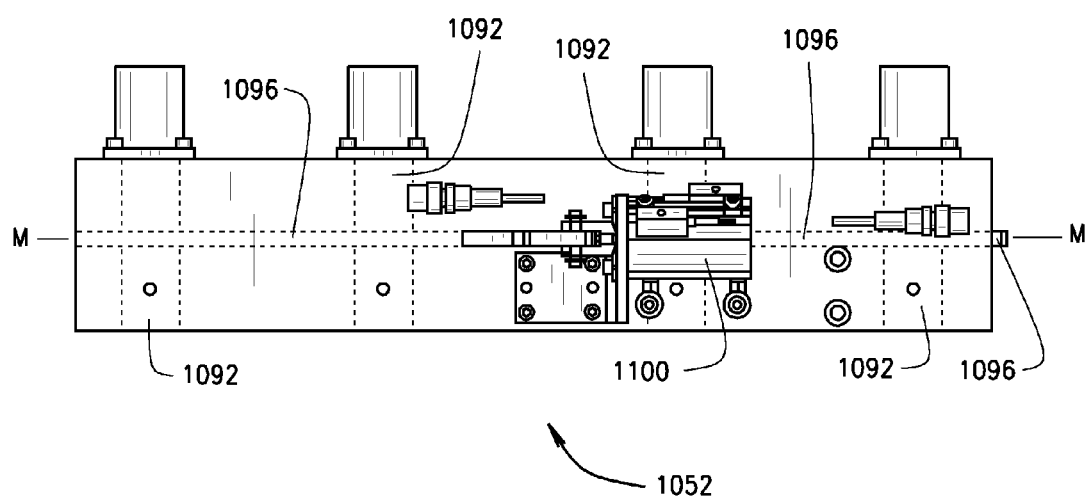
FIG. 15B is a side view of an escapement assembly of the load and transport subsystem shown in FIG. 15A, in accordance with various embodiments of the present disclosure.
Figure 15C:
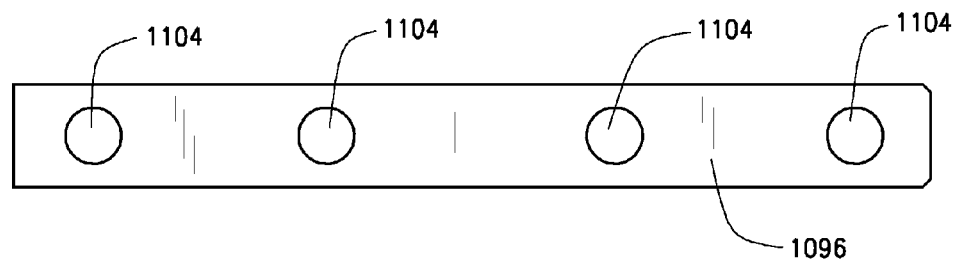
FIG. 15C is a top view of a retention slide of the escapement assembly shown in FIG. 15B, in accordance with various embodiments of the present disclosure.

Referring now to FIGS. 15A, 15B and 15C, in various embodiments, the escapement assembly 1052 includes a plurality of interior chambers 1092 that are laterally dissected by a retention slide 1096. The retention slide 1096 is slidably mounted within the escapement assembly such that the retention slide 1096 can be slidingly transitioned between an 'Open' and a 'Closed' position along a longitudinal axis M of the escapement assembly 1052. More specifically, under the control of the master controller system 1028, the retention slide 1096 can be slidingly transitioned between the 'Open' and the 'Closed' position utilizing an actuator 1100 mounted to the side of the escapement assembly 1052 and operably connected to the retention slide 1096. As illustrated in FIG. 15C, the retention slide 1096 includes a plurality of openings 1104 longitudinally spaced along the length of the retention slide 1096 to coincide, or coordinate, with the longitudinal spacing of the interior chambers 1092 within the escapement assembly 1052.

The retention slide is operable to 'settle' the seeds, i.e., allow seeds received from the hopper and singulator 1004 to come to a rest, within the respective interior chambers 1092 and then timely deposit each seed in a respective one of a plurality of seed loading shoes 1108 of the on-loader 1008. That is, the master controller system 1028 coordinates and synchronizes the operations of the hopper and singulator 1004, the tube shuttle 1044 and the escapement assembly 1052 such that as the seeds are singulated and transferred to the escapement assembly 1052, the retention slide 1096 is initially in the 'Closed' position. When in the 'Closed' position, the retention slide openings 1004 do not align with the respective interior chambers 1092 such that the solid portion of the retention slide 1096 between the openings 1004 blocks the passage of each seed through the interior chamber 1092. The master controller system maintains the retention slide 1096 in the 'Closed' position for a period of time, e.g., 0.5 second to 1.0 second, sufficient to allow each seed to 'settle', i.e., come to a rest and substantially stop moving. Once the seeds are allowed to 'settle', the master controller system transitions the retention slide to the 'Open' position in which the retention slide openings 1004 align with the respective interior chambers 1092, thereby allowing each seed to pass through the respective interior chamber 1092 and fall, via gravity, forced air and/or vacuum, into a respective one of the loading shoes 1108, as described further below. The master controller system 1028 coordinates and synchronizes the operations of the hopper and singulator 1004, the tube shuttle 1044 and the escapement assembly 1052 such that seeds are singulated at a rate calculated to allow seeds transferred to the escapement assembly interior chambers 1092 to be 'settled' and released, i.e., deposited in the on-loader shoes 1108, before subsequent singulated seeds are transferred to the escapement assembly 1052.

Figure 15D:
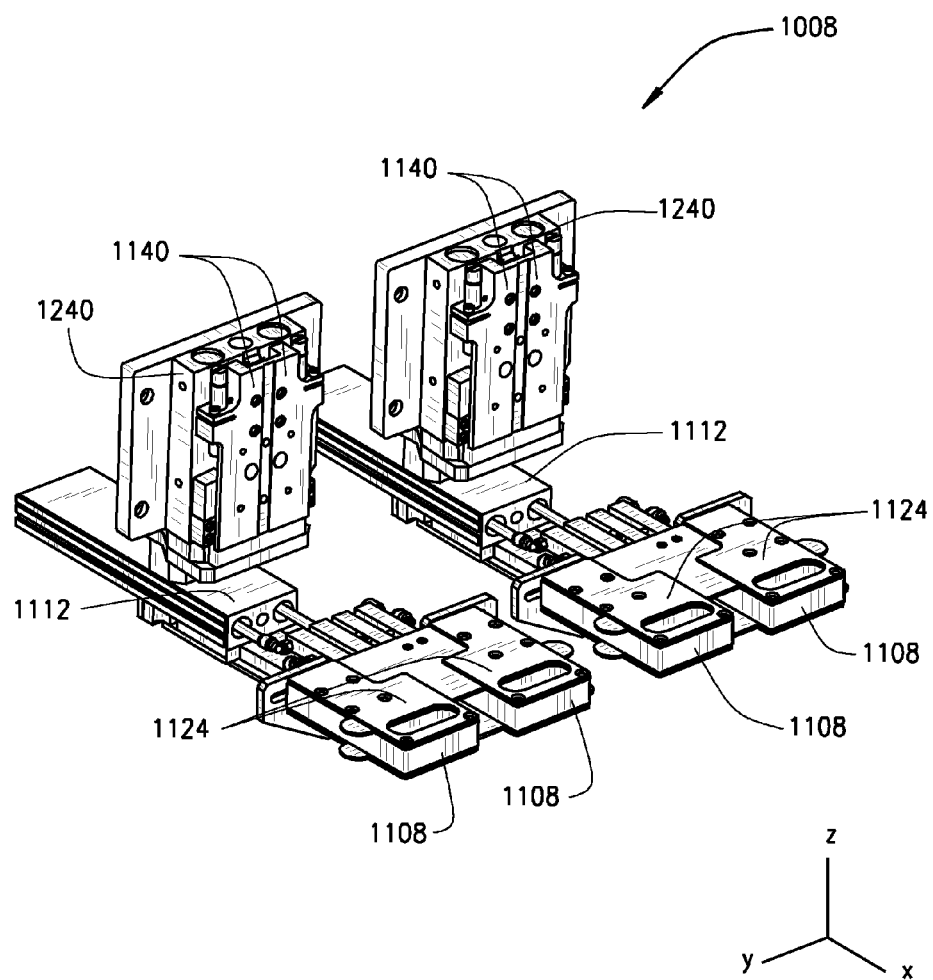
FIG. 15D is an isometric view an on-loader of the load and transport subsystem shown in FIG. 15A, in accordance with various embodiments of the present disclosure.

Referring now to FIGS. 15A and 15D, as described above, the on-loader 1008 includes a plurality of loading shoes 1108. Each loading shoe 1108 is mounted to one or more first linear actuators 1112 that are structured and operable, via commands from the master controller system 1028, to move the respective loading shoes 1108 along an X-axis of the on-loader 1008 between a 'Retracted', or 'Home', position (shown in FIG. 15A) and an 'Extended', or 'Loading', position (shown in FIG. 15D). Although FIGS. 15A and 15D exemplarily illustrate the on-loader 1008 as including two first linear actuators 1112, each having two loading shoes 1108 mounted thereto, it is envisioned that the on-loader 1008 can include more than or less than two first linear actuators 1112, each having more than or less than two loading shoes 1108 mounted thereto. For example, in various embodiments, the on-loader 1008 can include a single first linear actuator 1112 having four loading shoes 1108 mounted thereto, or the on-loader 1008 can include four first linear actuators 1112 each having a single loading shoe 1108 mounted thereto.

Figure 15E:
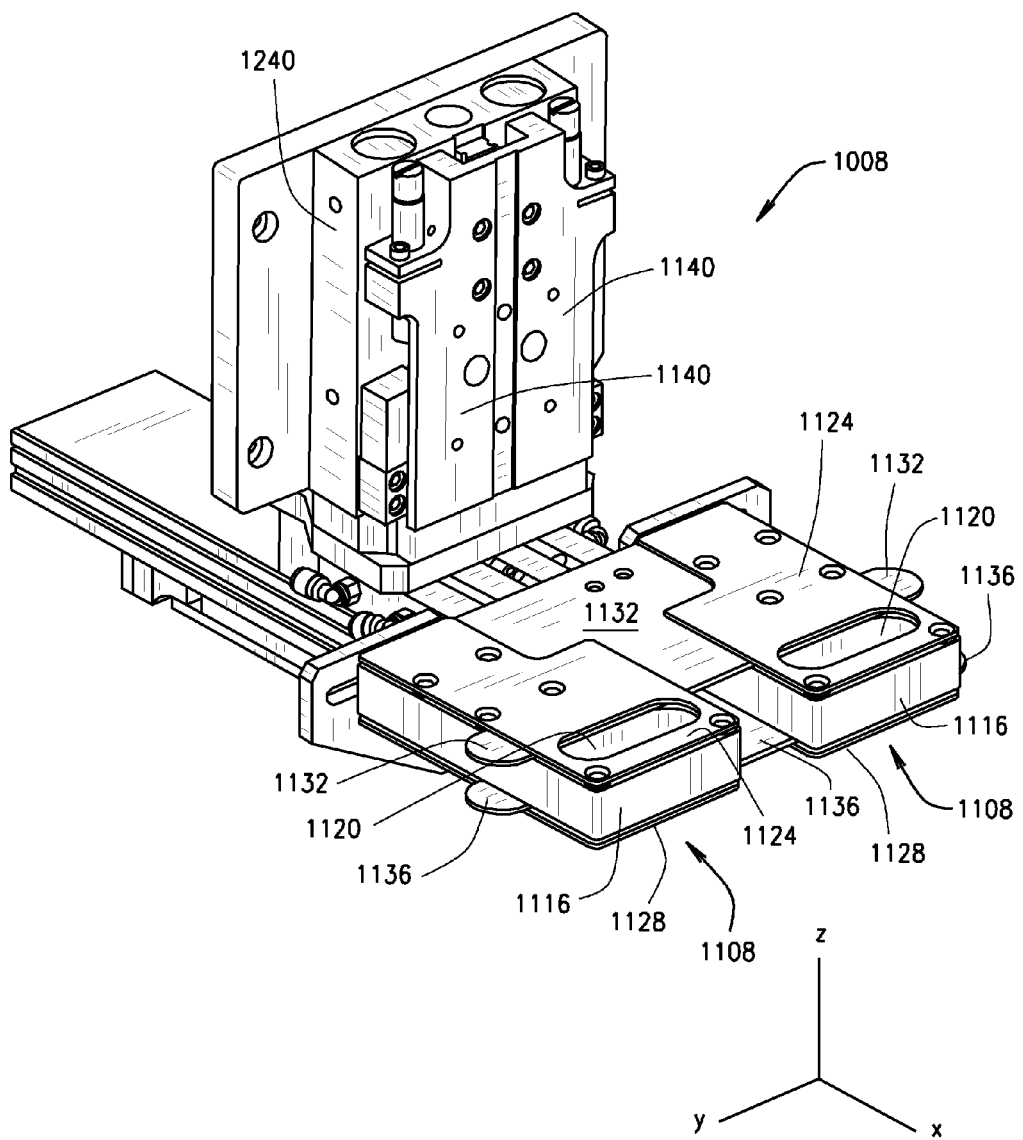
FIG. 15E is an isometric view of a pair of loading shoes of the on-loader shown in FIG. 15D, in accordance with various embodiments of the present disclosure.
Figure 15F:
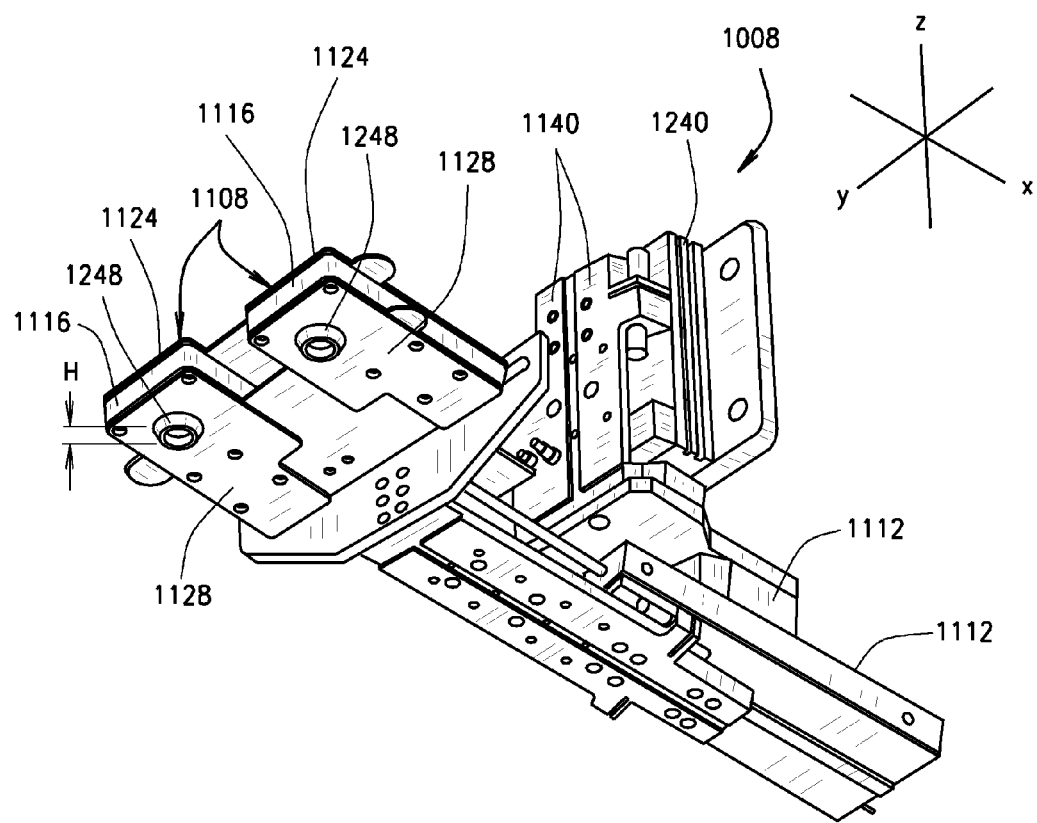
FIG. 15F is an isometric view of a bottom side of pair of loading shoes shown in FIG. 15E, in accordance with various embodiments of the present disclosure.

Referring now to FIGS. 15A, 15D, 15E and 15F, each loading shoe 1108 of the on-loader 1008 includes a body 1116 having a catch funnel 1120 formed in, and extending through, a distal end portion. Each catch funnel 1120 is formed to have a top end, i.e., the end adjacent escapement assembly 1052, and an opposing bottom end, wherein the top end of the catch funnel is larger in size than the bottom end. Each loading shoe 1108 additionally includes a top plate 1124 and a bottom plate 1128 connected to the body 1116. The top plate 1124 includes a hole that is symmetrical in shape and size and located above the top end of the catch funnel 1120 such that a perimeter of the top plate hole is aligned with a perimeter of the catch funnel top end. Similarly, the bottom plate 1128 includes a hole that is symmetrical in shape and size and located below the bottom end of the catch funnel 1120 such that a perimeter of the bottom plate hole is aligned with a perimeter of the catch funnel bottom end. Furthermore, each loading shoe 1108 includes a top aperture cover 1132 slidingly mounted between the body the top plate 1124 and a bottom aperture cover 1136 slidingly mounted between the body and the bottom plate. Each top aperture cover 1132 is structured and operable to be transitioned between an 'Open' position that allows access to the respective catch funnel 1120 (as shown in FIGS. 15A and 15E) and a 'Closed' position that blocks access to the respective catch funnel 1120 (as shown in FIG. 15D). Similarly, each bottom aperture cover 1136 is structured and operable to be transitioned between an 'Open' position that allows egress from the respective catch funnel 1120 (as shown in FIG. 15F) and a 'Closed' position that blocks egress to the respective catch funnel 1120 (as shown in FIG. 15E). Each of the top and bottom aperture covers 1132 and 1136 are transitioned between the 'Open' and 'Closed' position via actuators (not shown).

The first linear actuators 1112 and the loading shoe top and bottom aperture cover actuators (not shown) can be operated using any suitable power/energy source controlled by the master controller system 1028. For example, in various embodiments, each of the first linear actuators 1112 and the loading shoe top and bottom aperture cover actuators are pneumatically operated via one or more pneumatic regulators 1140 controlled by the master controller system 1028. Alternatively, each of the first linear actuators 1112 and the loading shoe top and bottom aperture cover actuators can be operated utilizing an electrical or hydraulic power/energy source. Moreover, the operations and actions taken by the various stations, systems, subsystems, assemblies, subassemblies and various components of the seed sorter system 10 can be operated using any suitable power/energy source, such as pneumatic, electrical and/or hydraulic power/energy sources.

In operation, the master controller system 1028 coordinates and synchronizes the operations of the hopper and singulator 1004, the tube shuttle 1044, the escapement assembly 1052 and the on-loader 1008 such that prior to the escapement assembly retention slide 1096 being transitioned to the 'Open' position to release the 'settled' seeds, the loading shoes 1108 are fully retracted to the 'Home' position. Additionally, the top aperture cover 1132 of each loading shoe 1108 is moved to the 'Open' position and the bottom aperture cover 1136 of each loading shoe 1108 is moved to the 'Closed' position. When the loading shoes 1108 are in the 'Home' position, the catch funnel 1120 of each loading shoe 1108 is located directly below a respective corresponding one of the escapement assembly interior chambers 1092. Therefore, as the escapement assembly retention slide is transitioned to the 'Open' position, the seeds are allowed to pass through the interior chamber 1092, as described above, and fall into the respective corresponding loading shoe catch funnel 1120. Subsequently, each respective loading shoe top aperture cover is moved to the 'Closed' position to enclose each seed within the respective catch funnel 1120.

Once the seeds are enclosed in the catch funnels 1120, the central controller system 1028 commands the on-loader first linear actuators 1112 to transition each of the loading shoes 1108 to the 'Loading' position, thereby positioning each catch funnel 1120 directly above a respective corresponding one of a plurality of mirrored imaging stages 1148 included in an imaging stage assembly 1152 (shown in FIGS. 16, 16A and 16B, and described further below) of the imaging theater 1012.

Referring now to FIG. 13B, in various embodiments, the imaging theater 1012 includes the imaging stage assembly 1152 mounted to system support structure of the optics and controller station 1002 between an upper ring light assembly 1156 and a lower ring light assembly 1160. Additionally, in various implementations, the imaging theater 1012 includes one or more bottom mirror assemblies 1164 mounted to system structure below the lower ring light assembly 1160.

Referring now to FIGS. 13B, 16, 16A and 16B, as described above, the imaging stage assembly 1152 is mounted to system support structure between the upper and lower ring light assemblies 1156 and 1160. More particularly, the upper ring light assembly 1156 includes a plurality of upper ring lights 1168 that are positioned above the imaging stage assembly 1152 such that a desired amount, intensity, type and/or wavelength of light can be provided by the upper ring lights 1168 to uniformly, i.e., evenly, illuminate a top portion of each of the imaging stages 1148. Similarly, the lower ring light assembly 1160 includes a plurality of lower ring lights 1172 that are positioned below the imaging stage assembly 1152 such that a desired amount, intensity, type and/or wavelength of light can be provided by the lower ring lights 1172 to uniformly, i.e., evenly, illuminate a bottom portion of each of the imaging stages 1148. Still more particularly, each of the lower ring lights 1172 includes a lower annular light assembly 1176 that is controllably illuminated to provide the desired amount, intensity, type and/or wavelength of light to the bottom portion of the imaging stages 1148 during image data collection for the seeds deposited onto each of the imaging stages, as described below. Similarly, each of the upper ring lights 1168 includes an upper annular light assembly 1180 that is controllably illuminated to provide the desired amount, intensity, type and/of wavelength of light to the top portion of the imaging stages 1148 during image data collection for the seeds deposited onto each of the imaging stages, as described below.

The upper and lower annular light assemblies 1180 and 1176 can be any luminary light assembly suitable to, independently or in combination with other devices, uniformly illuminate the imaging stages 1148 with a desired amount, intensity, type and/or wavelength of light. For example, as illustrated in FIG. 13B, in various embodiments the I&A subsystem 12 can include a light source 1184, and the upper and lower annular light assemblies 1180 and 1176 can comprise fiber optic light rings optically coupled to light source 1184 via fiber optic cables 1188. Accordingly, the light source 1184 can uniformly provide a light source of a particular amount and intensity that is transmitted through the fiber optic cables 1188 to the upper and lower fiber optic light rings, i.e., upper and lower annular light assemblies 1180 and 1176. The light source 1184 can be any light source that can be controlled by the master controller system 1028 to provide light a selectable and changeable amount and intensity.

Additionally, in various embodiments, the light source 1184 can include, or be operably coupled to, a multi-spectral high-speed optic filter device 1192 operable to filter various wavelengths of the light produced by the light source 1184 such that image data for each seed can be collected at various spectral wavelengths. For example, in various embodiments, the multi-spectral high-speed filter device 1192 can be structured to include a filter wheel including two, three, four, five six, seven, eight or more band pass filters to provide a plurality of different bands, i.e., wavelength bands, of spectral filtering. Accordingly, as described below, the imaging device (s) 1016, light source 1184 and filter device 1192 can be cooperatively operated to collect image data of the seeds deposited onto the imaging stages 1148 at a plurality of different spectral wavelengths, also referred to herein as multi-spectral imaging.

Alternatively, in various other embodiments, the upper and lower annular light assemblies 1180 and 1176 can comprise a plurality of light emitting diodes (LEDs) wherein different particular ones of the LEDs are structured to emit light at different particular intensities and/or wavelengths. For example, selected first ones of the LEDs can be illuminated to emit light of a particular first intensity and/or wavelength to collect first image data, then selected second ones of the LEDs can be illuminated to emit light of a particular second intensity and/or wavelength to collect second image data, and so on. Thus, the plurality of LEDs can be selectively illuminated by the master controller system 1028 to collect image data of the seeds deposited onto the imaging stages 1148 at a plurality of different spectral wavelengths.

Furthermore, the upper and lower annular light assemblies 1180 and 1176, and/or light source 1184, can be any type of light suited for the particular imaging application of the seed sorter system 10. For example, the upper and lower annular light assemblies 1180 and 1176, and/or light source 1184, can be incandescent lights, fluorescent lights, ultraviolet lights, infrared lights, etc.

Referring now to FIGS. 16, 16A, 16B and 16C, as described above, each imaging stage assembly 1152 includes a plurality of imaging stages 1148. In various embodiments, each imaging stage 1148 includes an annular mirror fixture 1196 fixedly mounted to system support structure and a trap-door bottom 1200 mounted to a controllably rotatable shaft 1204. Each annular mirror fixture 1196 includes a center opening 1208 and a plurality of, e.g., eight, imaging mirrors 1212, e.g., planar mirrors, mounted around an interior wall of each respective annular mirror fixture 1196. The imaging mirrors 1212 are substantially equally spaced around the respective annular mirror fixture 1196 interior wall and mounted at an angle θ calculated to reflect an image of a seed located substantially in the center of the opening 1208 to the imaging device(s) 1016. Thus, as described further below, image data can be collected for a plurality of different side portions, i.e., side views, of each seed. That is, the imaging device(s) 1016 and master controller system 1028 can collect image data of the top of each seed and image data reflected from each of the plurality imaging mirrors 1212 spaced around each respective seed. Additionally, the imaging device(s) 1016 and master controller system 1028 can collect image data of the bottom of each seed, via the one or more bottom mirror assemblies 1164.

The trap-door bottom 1200 of each imaging stage 1148 is generally formed as a basin having a perimeter wall opening to an egress chute 1216. Additionally, each trap-door bottom 1200 includes a clear, or transparent, center window 1220 fitted within a center aperture 1224 that is substantially concentric with the opening 1208 of the respective annular mirror fixture 1196 when the respective trap-door bottom 1200 is in a 'Seed Imaging' position. The center windows 1220 are sized to have a diameter D calculated to be significantly longer than the width of any seed to be imaged so that images of the bottom of each respective seed, i.e., the side of the seed resting on the window 1220, can be reflected from the respective bottom mirror assembly 1164 and pass around the seed and through the respective center window 1220 to the imaging device(s) 1016, as described further below. Additionally, the center windows 1220 can comprise any suitably clear, or transparent, material that will allow the images reflected from each bottom mirror assembly 1164 to pass around the seeds and through the windows 1220 without distorting, inhibiting or corrupting the reflected images. For example, in various embodiments, center windows 1220 can comprise a quartz glass window having high clarity and a very low refractive index, i.e., being very clear and having a refractive index that will not distort, inhibit, corrupt or otherwise negatively affect the quality of reflected images.

Each trap-door bottom 1200 is connected to the rotatable shaft 1204, which, in turn, is connected to a rotary actuator 1228 that is operable to bidirectionally rotate the shaft 1204. More particularly, the rotary actuator 1228, as commanded by the master controller system 1028, is operable to bidirectionally rotate the shaft 1204 to move the trap-door bottoms 1200 of each imaging stage 1148 between the 'Seed Imaging' position (shown in FIGS. 16A and 16C) and a 'Seed Off-load' position (shown in FIG. 16B). When the trap-door bottoms 1200 are in the 'Seed Imaging' position, the trap-door bottoms 1200 are positioned to be planarly parallel, and in close proximity to, or generally in contact with, a bottom 1232 of the respective annular mirror fixtures 1196. Therefore, when the trap-door bottoms 1200 are in the 'Seed Imaging' position and a seed is loaded, or deposited, onto each of the windows 1220 (as described below), each seed will steadily rest on the respective window 1220. Once the image data is collected for the seeds resting on the windows 1220, the rotary actuator 1228 is commanded to rotate the shaft 1204 to move the trap-door bottoms to the 'Seed Off-load' position, whereby the imaged seeds are allowed to slide off the respective windows 1220, via gravity, vacuum and/or forced air, through the respective egress chutes 1216 and into a mouth 1236 of a respective corresponding one of the imaged seed sorters 1020 (shown in FIGS. 17A and 17B), as described further below.

Referring now to FIGS. 15E, 15F, 16, 16A, 16B and 16C, in various embodiments, each on-loader 1008 additionally includes one or more second linear actuator 1240 that are structured and operable, via commands from the master controller system 1028, to move the respective loading shoes 1108 along a Z-axis of the on-loader 1008 between a "Raised" position (shown in FIGS. 15A and 15E) and a 'Lowered' position (shown in FIG. 15D). Although FIGS. 15A and 15D exemplarily illustrate the on-loader 1008 as including two second linear actuators 1240, each having two loading shoes 1108 mounted thereto, it is envisioned that the on-loader 1008 can include more than or less than two second linear actuators 1240, each having more than or less than two loading shoes 1108 mounted thereto. For example, in various embodiments, the on-loader 1008 can include a single second linear actuator 1112 having four loading shoes 1108 mounted thereto, or the on-loader 1008 can include four second linear actuators 1240 each having a single loading shoe 1108 mounted thereto.

As described above, when the seeds are enclosed in the catch funnels 1120 and the loading shoes 1108 are moved to the 'Loading' position, each catch funnel 1120 is positioned directly above a respective corresponding one of the mirrored imaging stages 1148. More particularly, when each catch funnel 1120 is positioned directly above the corresponding mirrored imaging stage 1148, the bottom end of each catch funnel 1120 is positioned directly above a center of the trap-door bottom window of the respecting imaging stage 1148. In various embodiments, the loading shoes 1108 are in the 'Raised' position as the seeds enclosed in the catch funnels 1120 and the loading shoes 1108 are moved to the 'Loading' position. Then, once the catch funnels 1120 are positioned directly above the corresponding mirrored imaging stages 1148, each second linear actuator 1240 is commanded to move the loading shoes 1108 to the 'Lowered' position such that each loading shoe bottom plate 1128 is in close proximity to a top 1244 of the annular mirror fixture 1196, i.e., approximately 0.5 to 2.0 mm above the top 1244 of the annular mirror fixture 1196. Each loading shoe bottom aperture cover is then commanded to 'Open' position such that each seed falls out of the respective catch funnel 1120 is deposited onto the center of the respective trap-door bottom window 1220.

Moreover, in various embodiments each loading shoe 1108 includes a damping ring 1248 attached to the respective bottom plate 1128 around the perimeter of the bottom plate hole and aligned with the bottom end of the respective catch funnel 1120. When the catch funnels 1120 are positioned directly above the corresponding mirrored imaging stages 1148 and the loading shoes 1108 are moved to the 'Lowered' position, each damping ring 1248 will protrude into the respective annular mirror fixture center opening 1208. Thus, as each seed is released from the respective catch funnel 1120, the damping rings 1248 will locate each respective seed approximately in the center of the respective trap-door bottom window 1220. More specifically, each damping ring 1248 has a height H that is calculated such that when the loading shoes 1108 are moved to the 'Lowered' position, each damping ring 1248 will be centered with, and in close proximity to, the respective trap-door bottom window 1220, i.e., approximately 0.5 to 2.0 mm above the center of the trap-door bottom window 1220. Therefore, as the seeds are released from the catch funnels 1120 the seeds will fall onto the center trap-door bottom windows 1220 and will be retained within the damping rings 1248, at the center of the trap-door bottom windows 1220 until the seeds 'settle' and come to rest at the center of the trap-door bottom windows 1220. Subsequently, the master controller system 1028 will command the first and second on-loader linear actuators 1112 and 1240 to raise loading shoes 1108, along the Z-axis, and retract loading shoes 1108, along the Y-axis, to return the loading shoes 1108 to the 'Home' position.

Figure 16:
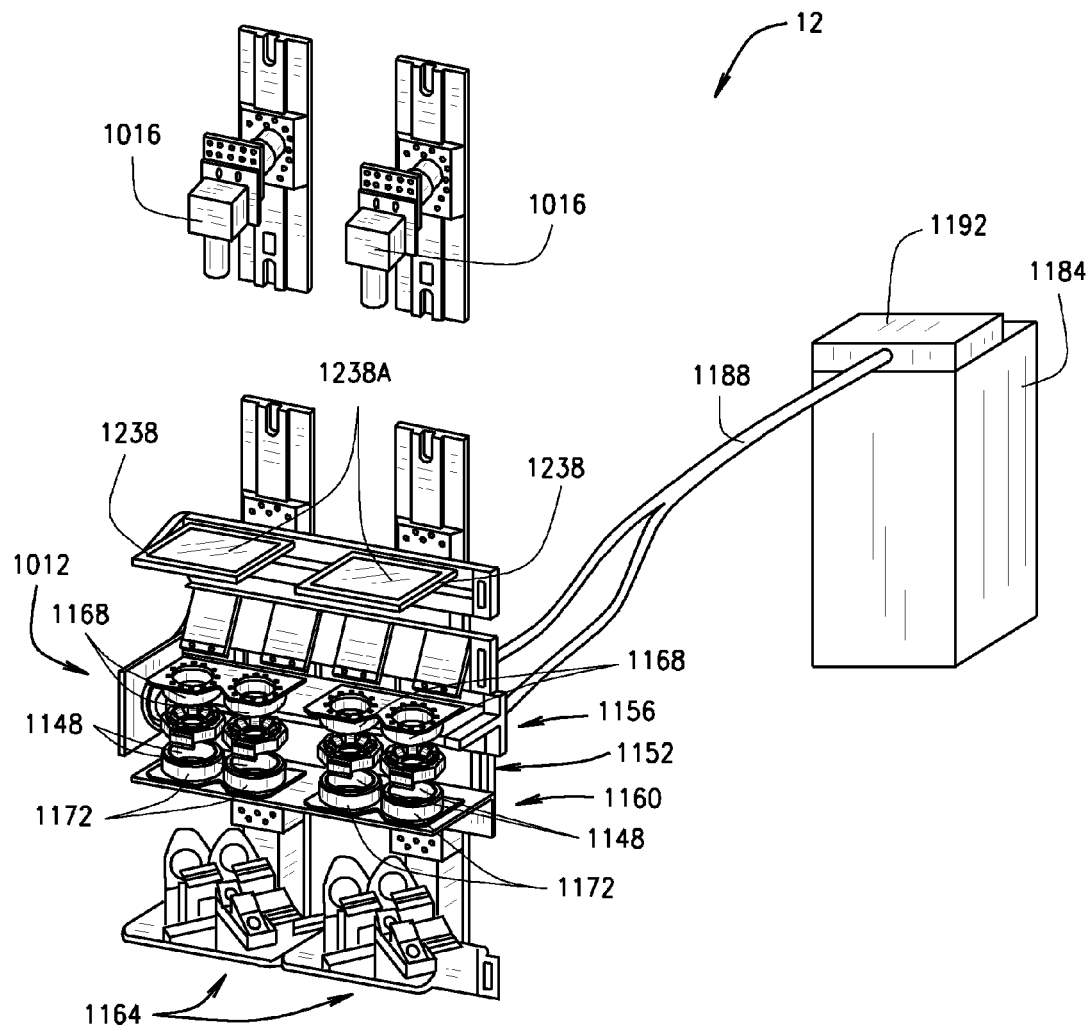
FIG. 16 is an isometric view of an imaging and analysis subsystem of the seed sorter system shown in FIG. 13A, in accordance with various embodiments of the present disclosure.
Figure 16A:
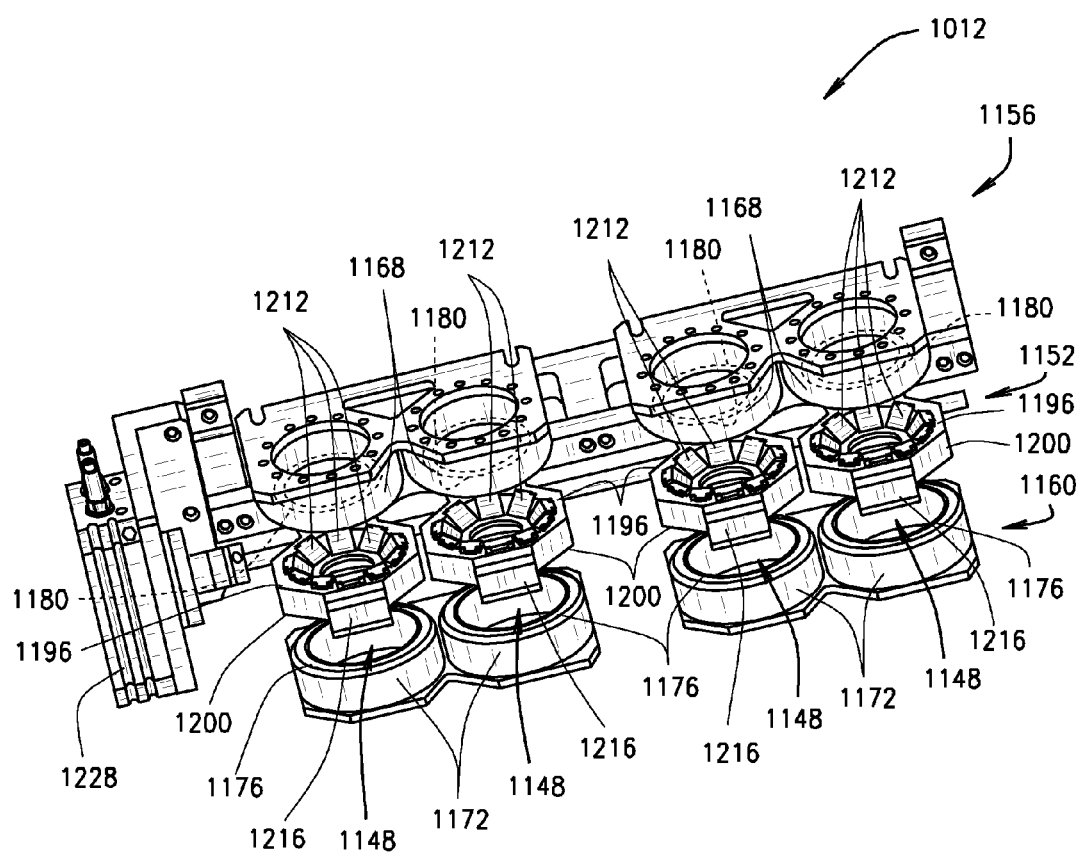
FIG. 16A is an isometric view of a portion of an imaging theater included in the imaging and analysis subsystem shown in FIG. 16, in accordance with various embodiments of the present disclosure.
Figure 16B:
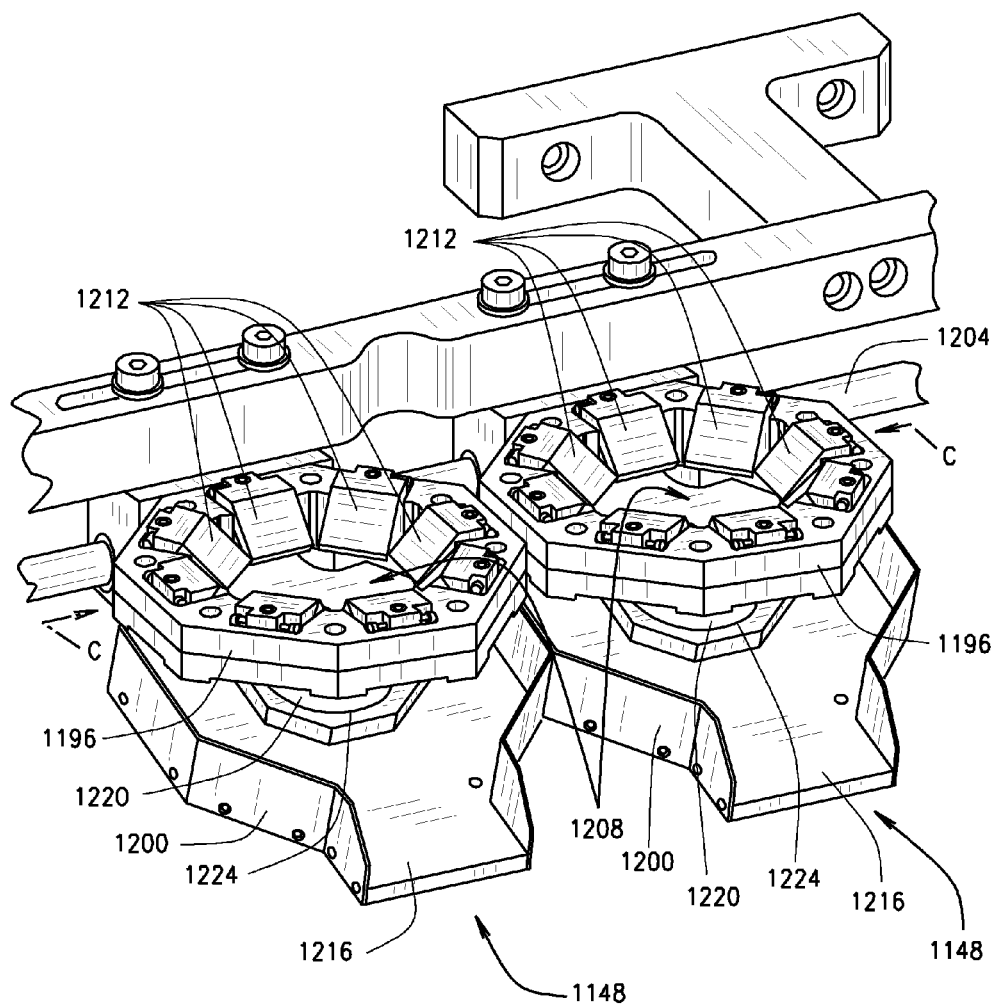
FIG. 16B is an isometric view of an imaging stage assembly included in the portion of the imaging theater shown in FIG. 16A, illustrating trap-door bottoms of a plurality of imaging stages in a seed dump position, in accordance with various embodiments of the present disclosure.
Figure 16E:
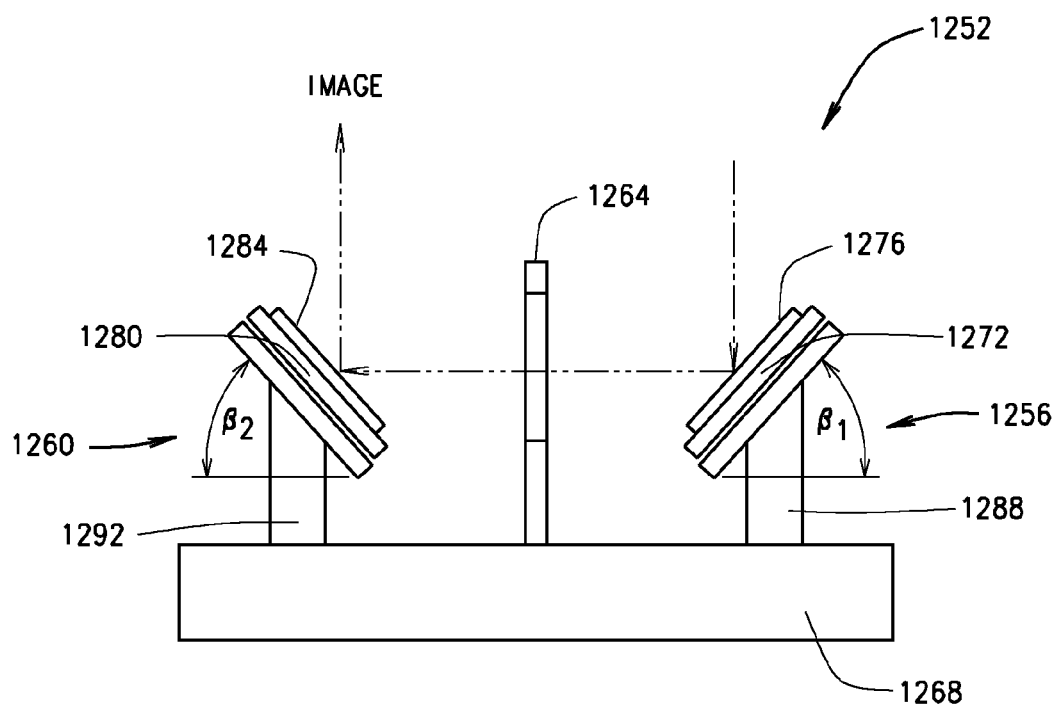
FIG. 16E is a cross-sectional view along line E-E of the mirror assembly shown in FIG. 16D, in accordance with various embodiments of the present disclosure.

Referring now to FIGS. 16, 16D and 16E, as described above, image data of the bottom of each seed loaded onto the imaging stages 1148 is collected utilizing the one or more bottom mirror assemblies 1164 mounted to system support structure below the imaging stage assembly 1152. In various embodiments, each bottom mirror assembly 1164 includes one or more stanchion mirror fixture 1252. Specifically, the imaging theater 1012 includes one or more bottom mirror assemblies 1164 that cumulatively include a stanchion mirror fixture 1252 for each imaging stage 1148. Each stanchion mirror fixture 1252 includes a first mirror stand 1256, a second mirror stand 1260 and a focal lens 1264, each of which are mounted to a base 1268. The first mirror stand 1256 includes a first angled table 1272 having a first bottom mirror 1276, e.g., a planar mirror, mounted thereto. Similarly, the second mirror stand 1260 includes a second angled table 1280 having a second bottom mirror 1284, e.g., a planar mirror, mounted thereto. The first angled table 1272 is adjustably mounted to a first post 1288 such that first angled table 1272, and thus, the first bottom mirror 1276, can be positioned at an angle $\beta_1$ with respect to the base 1268, and the second angled table is adjustable mounted to a second post 1292 such that second angled table 1280, and thus, the second bottom mirror 1284, can be positioned at an angle $\beta_2$ with respect to the base 1268. Each focal lens is structured to optically focus the image reflected from the first bottom mirror 1276 to the second bottom mirror 1284 to accommodate the focal length between the first and second bottom mirrors 1276 and 1284.

As described above, the center windows 1220 of each imaging stage 1148 is sized to have a diameter D calculated to allow images of the bottom of each respective seed to be reflected from the respective bottom mirror assembly 1164 and pass around the seed and through the respective center window 1220 to the respective imaging device 1016. More particularly, to acquire image data for the bottom of each seed, the angles $\beta_2$ and $\beta_1$ of the first and second angled tables 1272 and 1280 for each stanchion mirror fixture 1252 are adjusted such that a reflected image of the bottom of each respective seed is directed from the first bottom mirror 1276 through the focal lens 1264 to the second bottom mirror 1284, and then through the respective center window 1220 to the respective imaging device 1016. Each focal lens 1264 focuses the respective image reflected from the first bottom mirror 1276 to the second bottom mirror 1280. The lower ring lights 1172 are controlled by the master controller system 1028 to provide the desired amount, intensity, type and/or wavelength of light used to illuminate the bottom of each seed as the bottom image data can be acquired. Moreover, as described above, in various embodiments, the light source 1184 can include, or be operably coupled to, the multi-spectral high-speed optic filter device 1192 to filter various wavelengths of the light produced by the light source 1184 such that bottom image data for each seed can be collected at various spectral wavelengths.

In various embodiments, the I&A subsystem 12 can further include one or more transparent image intensity buffer lens shelves 1238 mounted to system support structure between the upper ring light assembly 1156 and the imaging device(s) 1016. Each image intensity buffer lens shelf 1238 comprises a transparent plate 1238A on which one or more image intensity buffer lenses can be placed. Each transparent plate 1238A can comprise any suitably clear, or transparent, material that will allow the images projected and reflected imaging theater 1012 to pass through the transparent plates 1238A without distorting, inhibiting or corrupting the image data. For example, in various embodiments, each transparent plate 1238A can comprise a quartz glass plate having high clarity and a very low refractive index, i.e., being very clear and having a refractive index that will not distort, inhibit, corrupt or otherwise negatively affect the quality of the projected and reflected image data.

Due to the various different focal distances between the imaging devices and the various sources of image data, i.e., the top portion of the seeds, the imaging stage image mirrors 1212 and the first and second bottom mirrors 1276 and 1284, intensity of the image data provided by the image data sources can vary. To substantially equalize the intensity of the image data provided by the various image data sources, one or more image intensity buffer lens (not shown) can be strategically placed on the one or more image intensity buffer lens shelves 1238. Generally, the image intensity buffer lenses reduce the intensity of particular image data so that the intensity level of all the image data from the various sources is substantially the same. The various image intensity buffer lenses can have different intensity buffer coefficients and can be manually or automatically located on respective image intensity buffer lens shelf 1238 to substantially equalize the intensity of the image data provided by the various image data sources.

Referring now to FIGS. 13A, 13B, 16, 16A, 16B, 16C, 16D and 16E, as described above, the I&A subsystem 12 includes the one or more imaging devices 1016. Each imaging device 1016 is mounted to system support structure above the imaging stage assembly 1152 to have a field of view that includes one or more imaging stages 1148. For example, in various embodiments, the I&A subsystem 12 can include an imaging stage assembly 1152 that includes four imaging stages 1148, and two imaging devices 1016, wherein each imaging device 1016 is mounted to system support structure to have a field of view that includes a respective corresponding pair of imaging stages 1148. Although the I&A subsystem 12 can include more than or less than two imaging devices 1016, and/or more than or less than four imaging stages 1148 and remain within the scope of the present disclosure, for simplicity and clarity, the I&A subsystem 12 will be exemplarily described hereafter as including two imaging devices 1016 and four imaging stages, wherein each imaging device 1016 has a field of view that encompasses a respective corresponding pair of imaging stages 1148.

Therefore, once a seed is loaded, or deposited, onto each trap-door bottom window 1220, each imaging device 1016 has a field of view of the seed that includes the top, or upward facing, portion of the respective corresponding two imaging stages 1148, imaging mirrors 1212 and the seeds therein.

That is, each imaging device 1016 is positioned to collect image data of the top of the respective corresponding two imaging stages 1148 and the top of the seeds therein. Furthermore, each imaging device 1016 is positioned to collect image data of a plurality of side portions, i.e., side views, of each seed reflected from each of the imaging mirrors 1212 and image data of the bottom portion of each seed reflected from the respective stanchion mirror fixtures 1252. Thus, each imaging device 1016 is oriented and operable to collect, and transmit to the master controller system 1028, image data of the top portion, a plurality of side portions and the bottom portion of each seed deposited onto each of the respective corresponding imaging stages 1148. The image data of the top portion, bottom portion and plurality of side portions, i.e., side views, of each seed collected by each imaging device 1016 is transmitted to the master controller system 1028 for storage and analysis, as described below.

As used herein, reference to the top portion of the seeds refers to the portion of the seeds that is facing upward with respect to the orientation of each seed within the respective seed imaging stage. That is, as used herein, the top portion of the seeds refers to the portion of the seeds generally facing away from, and not resting on, the trap-door bottom window 1220 of each respective imaging stage 1148, and does not refer to the independent structure or anatomy of the seeds. Similarly, as used herein, the bottom portion of the seeds refers to the portion of the seeds generally facing toward, and generally resting on, trap-door bottom window 1220 of each respective imaging stage 1148, and does not refer to the independent structure or anatomy of the seeds.

Each imaging device 1028 can be any suitable imaging device selected in accordance with the imaging goals of the seed sorter system 10. For example, in connection with an analysis for external seed coat damage, each imaging device 1028 can comprise a digital camera operable in the visible light range. Alternatively, for internal seed analysis, each imaging device 1028 can comprise a camera operable in the near infra-red light range (see, U.S. Pat. No. 6,646,264, the disclosure of which is hereby incorporated by reference). Still further, each imaging device 1028 can comprise a camera which implements NMR/MRI imaging techniques (see, United States Published Application No. US 2006/0112628, the disclosure of which is hereby incorporated by reference).

Furthermore, in various embodiments, the master controller system 1028 coordinates and synchronizes the operation of each imaging device 1016 with the operation of the respective upper and lower ring light assemblies 1156 and 1160 to collect multi-spectral image data, i.e., image data at a plurality of different spectral wavelength and/or intensities, of the tops, the bottoms and a plurality of side views of each seed retained within the respective imaging stages 1148.

Figure 16F:
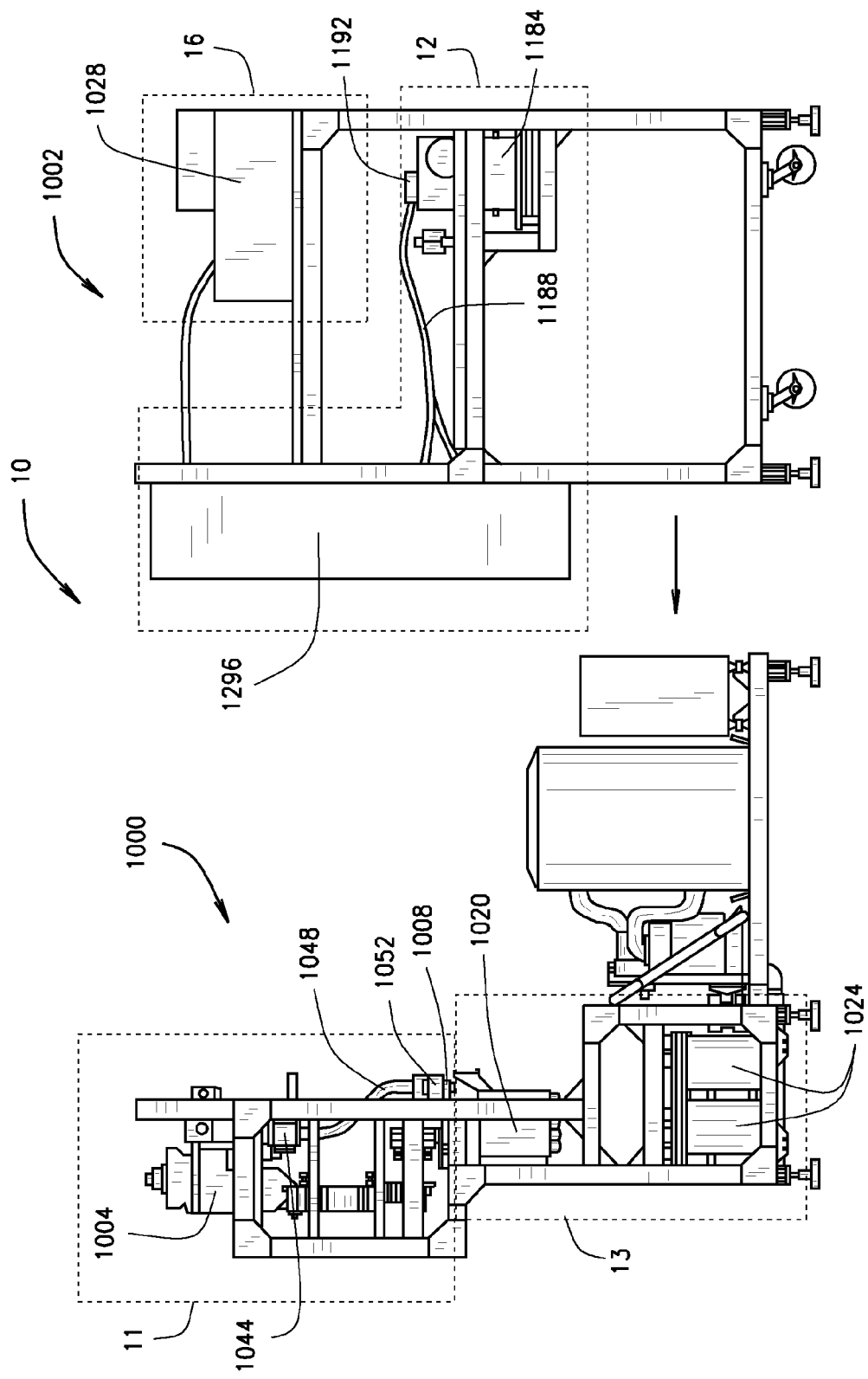
FIG. 16F is a side view of the seed sorter system shown in FIG. 13A, including a dark room enclosure, in accordance with other various embodiments of the present disclosure.

Referring now to FIG. 16F, in various embodiments, the I&A subsystem 12 further includes an opaque dark room enclosure 1296 that encloses the imaging devices 1016 and the imaging theater 1012 to provide dark environment in which the image data can be collected. In various embodiments, the dark room enclosure 1296 can be constructed to be removably attached to the system support structure of the optics and controller station 1002. Moreover, in various embodiments, the dark room enclosure 1296 can be constructed to include removable sides that are removably connectable to each other to form the dark room enclosure 1296.

With further reference to FIGS. 13A, 13B, 16, 16A, 16B, 16C, 16D and 16E, the image data collected by each imaging device 1016 includes data relating to the respective imaging stage 1148 and to the seeds retained therein. The image data is transmitted to the master controller system 1028 and stored (at least temporarily) in an electronic data storage device of the master controller system 1028. The master controller system 1028 analyzes the image data and correlates, or links the collected image date with each respective corresponding seed. Accordingly, all the collected image data, is analyzed and parsed to correlate the image data for each individual seed to the particular imaging stage 1148 in which the respective seed is retained. In this way, a link exists between each seed, the corresponding imaging stage 1148 and the corresponding image data.

The collected image data can be processed in a number of known ways to identify seed characteristics or phenotypic traits (for example, as described in U.S. Pat. No. 6,646,264 or US 2006/0112628 referenced above). For example, image data analysis can reveal characteristic information of the individual seeds concerning, for example, the presence/absence of biochemical traits (like oil content), the presence or absence of damage, the presence or absence of disease, size, color, shape and the like. This characteristic information is obtained by processing the image data using custom algorithms executed on the collected image data by the master controller system 1028. The results of this processing are then stored, at least temporarily, in correlation with particular seeds, and more specifically, in correlation with respective imaging stage 1148 in which each seed is retained during imaging. In this way, a link exists between the image data and characteristic information of each seed.

As described further below, in various embodiments, the master controller system 1028 executes various algorithms to perform multi-spectral multi-variate analysis on the image data for each seed to determine specific surface color traits of each respective seed. For example, in various embodiments, the seeds may comprise corn seeds for doubled haploid breeding wherein diploid seeds have a blue anthocyanin marker in the germ area. Multi-spectral multi-variate analysis can be performed on the image data for each corn seed to determine if each individual corn seed has the blue marker. The seeds determined to have the blue marker are therefore identified as diploid seeds, seeds in which the blue marker is absent are identified as haploid seeds, and seeds in which it is uncertain whether the blue marker is present are identified as undetermined. Additionally, in various embodiments, analysis of the collected image data of a particular seed might reveal that the size of the seed does not meet or exceed a particular size threshold, indicating that the particular seed is a broken seed or seed fragment. In such instances, the master controller system 1028 can identify the seed as a seed fragment. The identified characteristics for each seed, or lack thereof, can then be applied by the master controller system 1028 against certain seed sorting criteria in order to effectuate the sorting of the seeds by characteristic, as described below.

Referring now to FIGS. 13A, 16, 16A, 16B, 17A, 17B and 17C, once the image data is collected for each of the seeds resting on the trap-door bottom windows 1220, the rotary actuator 1228 is commanded to rotate the shaft 1204 to move the trap-door bottoms 1200 to the 'Seed Off-load' position, whereby each imaged seed is allowed to slide off the respective window 1220, through the respective egress chute 1216 and into a mouth 1236 of a respective corresponding one the imaged seed sorters 1020. Although, for simplicity and clarity, the figures generally only illustrate a single imaged seed sorter 1020, it should be understood that the OL&S subsystem 13 includes a plurality of imaged seed sorters 1020. More particularly, the OL&S subsystem 13 includes an imaged seed sorter 1020 for each imaging stage 1148 of the imaging stage assembly 1152. For example, if the imaging stage assembly 1152 includes four imaging stages 1148, the OL&S subsystem 13 will include four imaged seed sorters 1020. Or, if the imaging stage assembly 1152 includes six imaging stages 1148, the OL&S subsystem 13 will include six imaged seed sorters 1020.

Each imaged seed sorter 1020 is mounted to system support structure such that the mouth 1236 of each imaged seed sorter 1020 is adjacent to and aligned with the egress chute

1216 of the respective corresponding imaging stage 1148. More particularly, each imaged seed sorter 1020 is located such that when the trap-door bottoms 1200 are moved to the 'Seed Off-load' position, each of the imaged seeds will slide off the respective windows 1220, through the respective egress chutes 1216 and into the mouths 1236 of the respective corresponding imaged seed sorters 1020.

Figure 17A:
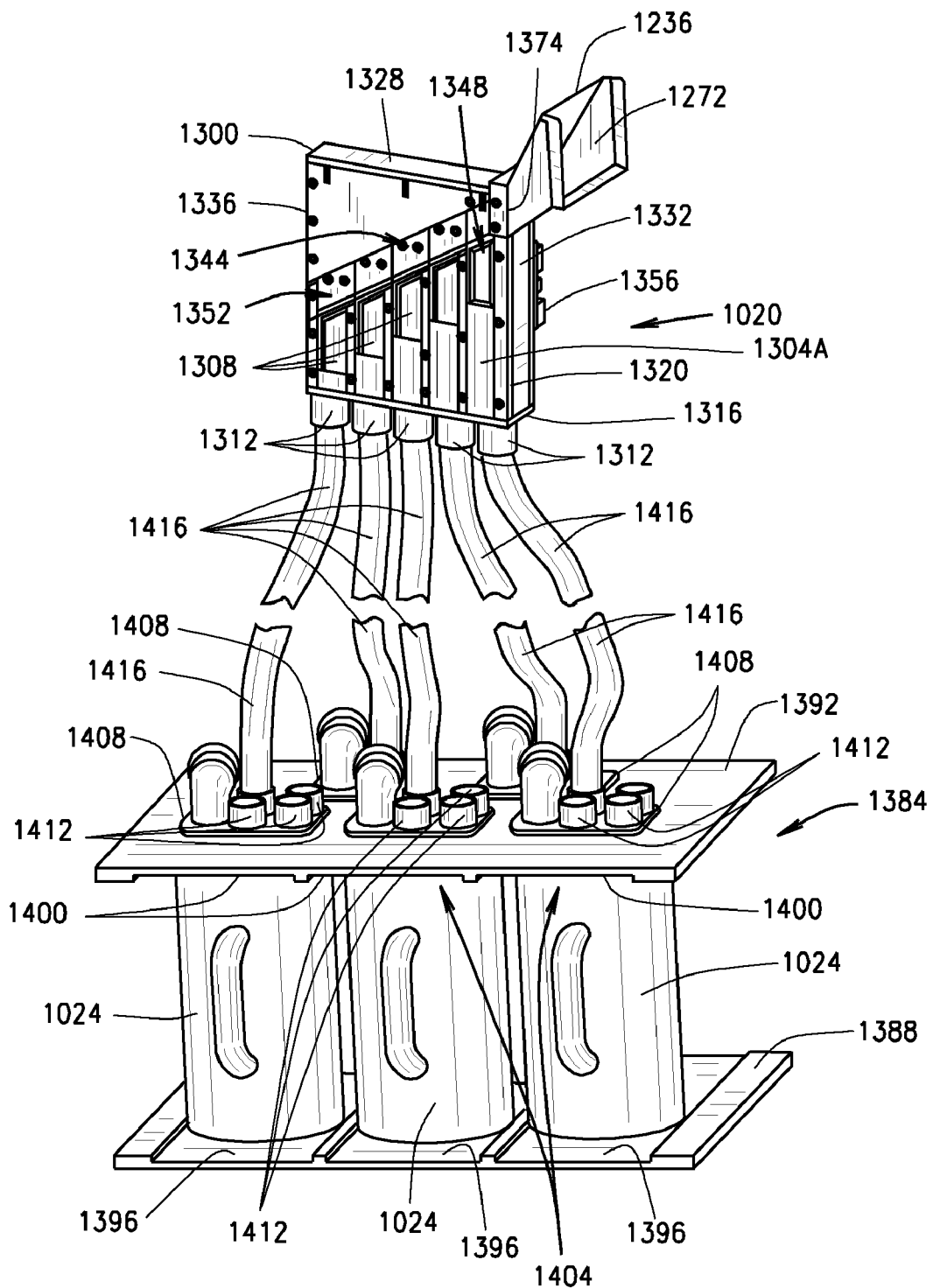
FIG. 17A is an isometric view of an off-loading and sorting subsystem of the seed sorter system shown in FIG. 13A, in accordance with various embodiments of the present disclosure.
Figure 17B:
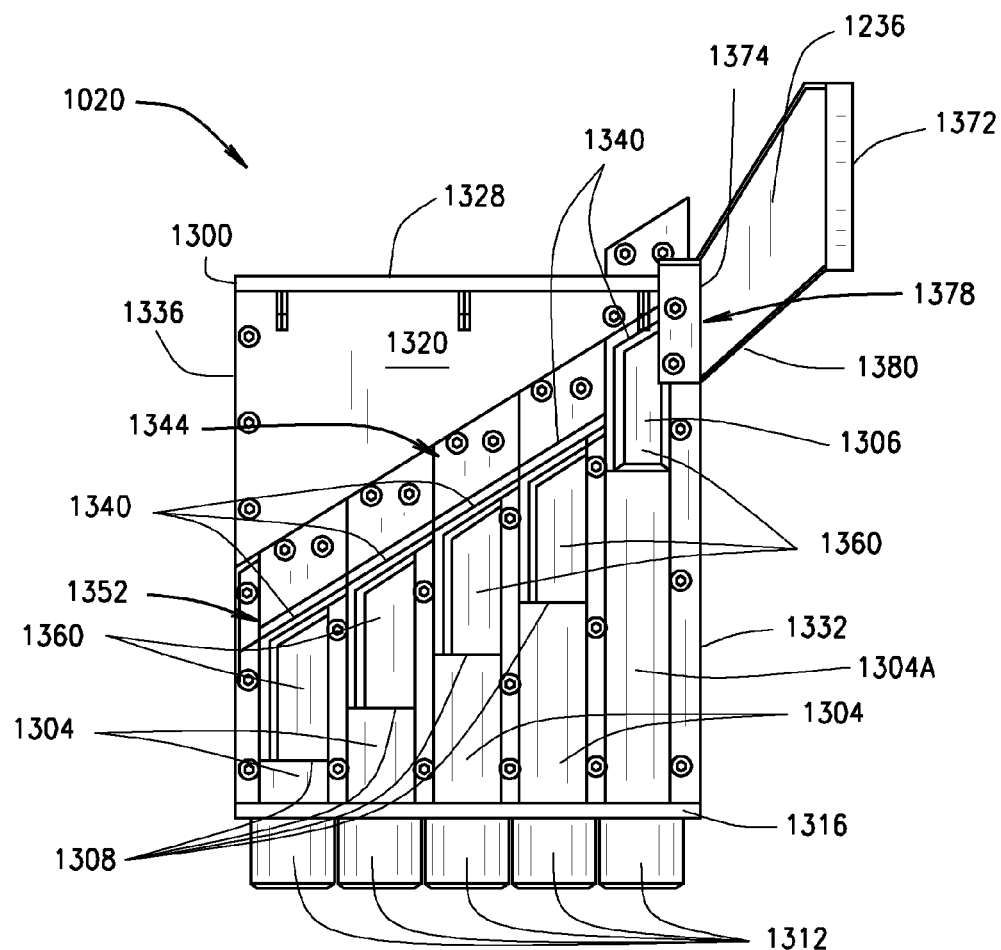
FIG. 17B is side view of an imaged seed sorter of the off-loading and sorting subsystem shown in FIG. 17A, in accordance with various embodiments of the present disclosure.
Figure 17C:
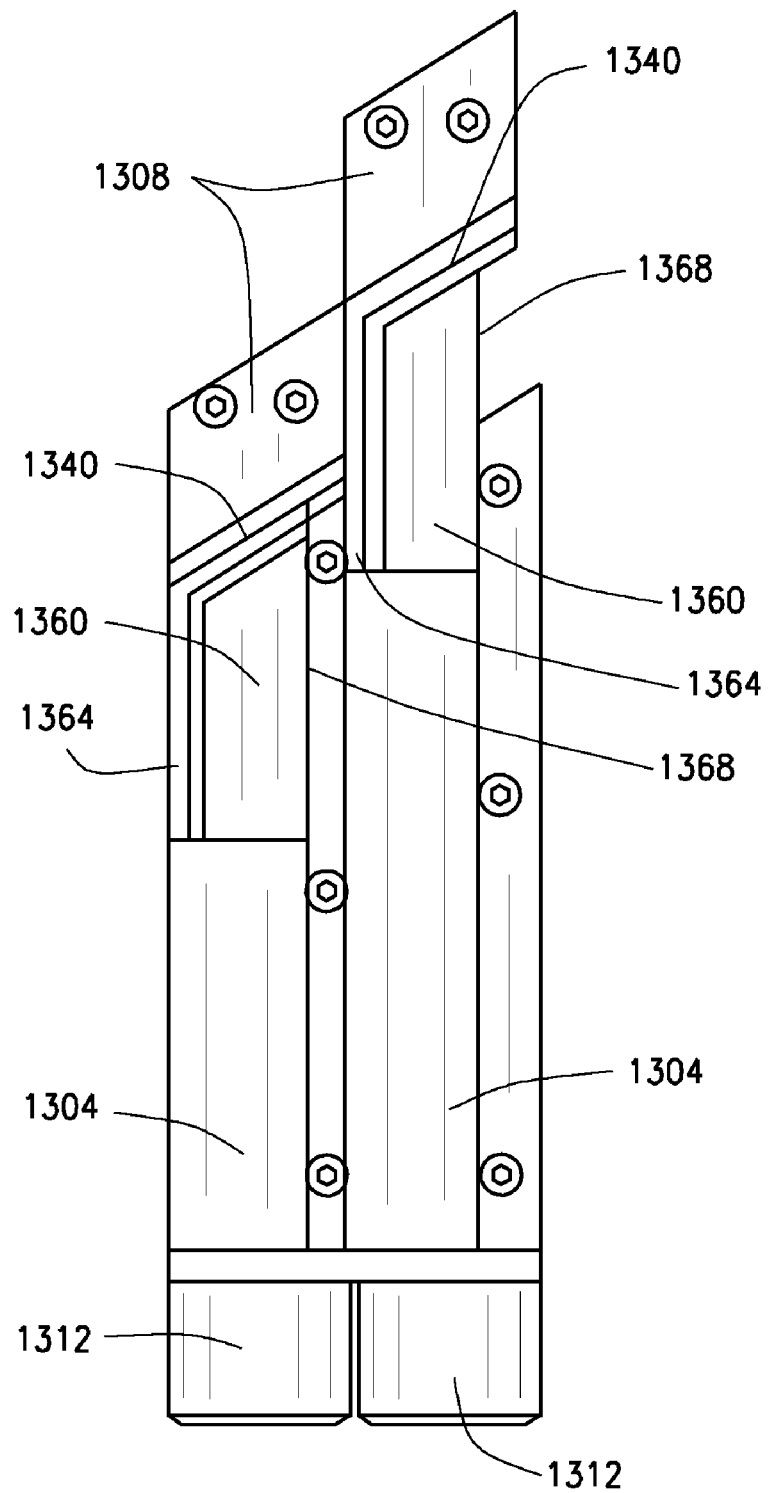
FIG. 17C is a side view of a pair of sorting channels and seed diverter plugs included in the imaged seed sorter shown in FIG. 17B, in accordance with various embodiments of the present disclosure.

Referring now to FIGS. 17A, 17B and 17C, each imaged seed sorter 1020 generally comprises a box-like housing 1300 that encloses a plurality of sorting channels 1304. Controllably slideable within a top portion of a first sorting channel 1304A, i.e., the sorting channel 1304 closest to the imaged seed sorter mouth 1236, is a cueing plug 1306. As described further below, the cueing plug 1306 is structured and operable to momentarily retain seeds within the imaged seed sorter mouth 1236 and momentarily block the seeds from entering the imaged seed sorter 1020. Controllably slideable within a top portion of each of the remaining sorting channels 1304 is respective corresponding one of a plurality of diverter plugs 1308. As described further below, each diverter plug 1308 is structured and operable to divert seeds into the respective shorting channel 1304. A bottom portion of each sorting channel 1304/1304A terminates at a respective corresponding one of a plurality of collared exit ports 1312 spaced along a bottom 1316 of the respective imaged seed sorter 1020. The housing 1300 includes a first side panel 1320 and an opposing second side panel 1324 that are connected to the bottom 1316, a top 1328, a front 1332 and a back 1336 to form the housing 1300. The first side panel 1320 is shown as being transparent to illustrate sorting channels 1304 and diverter plugs 1308, however the first side panel can be opaque and remain within the scope of the present disclosure.

Each diverter plug 1308 and the cueing plug 1306 includes an angled top wall 1340. The angled top wall 1340 of each diverter plug 1308 and the cueing plug 1306 linearly aligns with the angled top wall 1340 of each immediately adjacent diverter plug 1308 or cueing plug 1306 to form an angled sorting ramp 1344. Moreover, the angle top walls 1340 cumulatively linearly align such that the sorting ramp 1344 has downward or declining slope from a high end 1348 of the sorting ramp 1344 to a low end 1352 of the sorting ramp 1344. Each diverter plug 1308 and the cueing plug 1306 is connected to a respective corresponding one of a plurality of plug actuators 1356 mounted to the second panel 1324. Although only a single plug actuator 1356 is shown in FIG. 17A, it will be easily and readily understood that each diverter plug 1308 and the cueing plug 1306 is connected to a respective corresponding plug actuator 1356 mounted to the second panel 1324. Each plug actuator 1356 coupled to a diverter plug 1308 is operable, via commands from the master controller system 1028, to move each respective diverter plug 1308 between a 'Seed Diverting' position (as shown in the right most sorting channel 1304 of FIG. 17C) and a 'Seed By-pass' position (as shown in the left most sorting channel 1304 of FIG. 17C). Similarly, the plug actuator 1356 coupled to cueing plug 1306 is operable, via commands from the master controller system 1028, to move the cueing plug 1306 between a 'Cueing' position (as shown in FIG. 17B) and a 'Access' position (as shown in FIG. 17A).

As best illustrated in FIG. 17C, each diverter plug 1308 includes a seed catch cavity 1360 formed by the respective top wall 1340 and a respective back wall 1364. Each seed catch cavity 1360 includes an open side 1368 that opens toward the imaged seed sorter mouth 1236 when the respective diverter plug 1308 is in the 'Seed Diverting' position. The mouth 1236 of each imaged seed sorter 1020 includes a open seed receiving end 1372 that opens toward the aligned egress chute 1216 of the respective corresponding imaging stage 1148, and an opposing open funneled end 1374. Additionally, the imaged seed sorter front 1332 includes an opening 1378 adjacent the sorting ramp high end 1348. The imaged seed sorter mouth 1236 is connected to the housing 1300 such that the open funneled end 1374 aligns with the opening 1378. More particularly, the imaged seed sorter mouth 1236 is connected to the housing 1300 such that a bottom 1380 of the seed sorter mouth 1236 aligns with the opening 1378 and the sorting ramp 1344. Therefore, as described below, a seed deposited into the seed sorter mouth 1236 at the seed receiving end 1372 will slide along the bottom 1380 to the funneled end 1374 and smoothly transition, i.e., absent obstruction, through the imaged seed sorter front opening 1378 onto the angled sorting ramp 1344.

Referring now to FIG. 17A, in various embodiments, the plurality of seed repositories 1024 are retained within a seed repository retention fixture 1384. The seed repository retention fixture 1384 includes a base plate 1388 and a ported top plate 1392 between which the seed repositories 1024 are removably retained. That is, the base plate 1388 and the top plate 1392 are mounted to system support structure and spaced apart a sufficient distance to allow the seed repositories 1024 to be easily inserted and removed from between the base and top plates 1388 and 1392. In various implementations, the base plate 1388 includes a plurality of recessed seed repository bottom alignment slips 1396, and the top plate 1392 includes a plurality of recessed seed repository top alignment slips 1400. The bottom and top alignment slips 1396 and 1400 are structured to retain each of the seed repositories 1024 in a particular location within the retention fixture 1384. More specifically, the bottom and top alignment slips 1396 and 1400 are located within the respective base and top plates 1388 and 1392 to retain each of the seed repositories 1024 such that an open top 1404 aligns with a respective corresponding one of a plurality of collared port manifolds 1408 coupled to the top plate 1392.

Each collared port manifold 1408 is mounted to the top plate 1392 over a respective corresponding one of a plurality of apertures (not shown) in the top plate 1392. Additionally, each collared port manifold 1408 includes a plurality of collared entry ports 1412 that are located over the respective aperture such that seeds passing through any of the collared entry ports 1412, as described further below, will be deposited into the respective seed repository 1024. The OL&S subsystem 13 further includes a plurality of second transfer tubes 1416 that are interconnected between each collared exit ports 1312 of each imaged seed sorter 1020 and the collared entry ports 1412 of the collared port manifolds 1408.

More specifically, in various embodiments, the seed repository retention fixture 1384 can include a number of collared port manifolds 1408 and seed repositories 1024 equal to the number of collared exit ports 1312 and sorting channels 1304/1304A of one of the imaged seed sorters 1020. Additionally, each collared port manifold 1408 can include a number of collared entry ports 1412 equal to the number of imaged seed sorters 1020 included in the OL&S subsystem 13, i.e., equal to the number of imaging stages 1148 included in the imaging stage assembly 1152. For example, if the OL&S subsystem 13 includes four imaged seed sorters 1020 to accommodate four imaging stages 1148, and each imaged seed sorter 1020 includes five sorting channels 1304 and collared exit ports 1312, the seed repository retention fixture 1384 will include five collared port manifolds 1408, each having four collared entry ports 1412. Still more specifically, via the second transfer tubes 1416, each collared exit port 1312 of each individual imaged seed sorter 1020 is connected to a collared entry port 1412 of a different collared port manifold 1408 and corresponding seed repository 1024. Therefore, during operation, as described below, the master controller system 1028 can control each imaged seed sorter 1020 to selectively divert each imaged seed received from the respective imaging stage 1148 to any of the seed repositories 1024 based on the particular phenotypes, i.e., characteristics and/or traits (such as, damage, disease, color, size, and the like), of each seed as determined by the I&A subsystem 12.

Referring now to FIGS. 17A, 17B and 17C, as described above, each diverter plug 1308 and the cueing plug 1306 is connected to a respective one of the plug actuators 1356 to selectively move the diverter plugs 1308 between the 'Seed Diverting' position and the 'Seed By-pass' position, and the cueing plug 1306 between the 'Cueing' position and the 'Access' position. More particularly, based on the phenotype of each seed as identified by the I&A subsystem 12 and master controller system 1028, the master controller system 1028 controls the operation of the plug actuators 1356 such that each individual seed will be sorted to a selected one of the seed repositories 1024, via the imaged seed sorters 1020.

Once a set of seeds is loaded, or deposited, onto the imaging stage assembly (i.e., once a respective seed is simultaneously loaded onto each of the imaging stages 1148) and the multi-spectral image data for each seed is collected, the trap door bottoms 1200 are moved from the 'Seed Imaging' position to the 'Seed Off-load' position. This allows each seed in the set of seeds slide off the respective trap door bottom 1200, via gravity, vacuum and/or forced air, and into the mouth 1236 of the respective corresponding imaged seed sorter 1020. Prior to, or substantially simultaneously with, the trap door bottoms 1200 being moved to the 'Seed Off-load' position, the master controller system 1028 commands the plug actuator 1356 for the cueing plug 1306 to move the cueing plug 1306 to the 'Cueing' position. Therefore, as each seed slides along the bottom 1380 of the respective imaged seed sorter mouth 1236, each seed will be blocked from entering the respective imaged seed sorter housing 1300, i.e., each seed will be retained, or cued, within the respective imaged seed sorter mouth 1236.

While the seeds are cued within the seed sorter mouths 1236, a subsequent set of seed can be loaded on the imaging stages 1148, as described above. Additionally, while the seeds are cued within the seed sorter mouths 1236, the image data for each cued seed is analyzed by the master controller system 1028, and the identified phenotype, i.e., characteristics and/or traits (such as, damage, disease, color, size, and the like) is linked to each respective seed. Based on the respective identified phenotype, the master controller system 1028 then determines to which of the seed repositories 1024 each seed is to be sorted. Then, based on the particular identified seed repository 1024 to which each individual seed is to be sorted, the master controller system 1028 commands a particular one of the plug actuators 1356 for each respective imaged seed sorter 1020 to move the corresponding diverter plug 1308 to the 'Seed Diverting' position. That is, the diverter plug 1308 of the sorting channel 1304 connected, via the second transfer tubes 1416, to the particular identified seed repository 1024 is moved to the 'Seed Diverting' position. Once the identified diverter plug 1308 for each respective imaged seed sorter 1020 is moved to the 'Seed Diverting' position, the master controller system 1028 commands the appropriate plug actuators 1356 to move the cueing plugs 1306 to the 'Access' position, thereby allowing the seeds access to the respective imaged seed sorter housings 1300.

More specifically, when the cueing plugs 1306 are moved to the 'Access' position, the seeds are allowed to slide, via gravity, vacuum and/or forced air, through the respective imaged seed sorter front openings 1378 onto the respective sorting ramps 1344. Each seed will then slide along the respective sloping imaged seed sorter sorting ramp 1344 and into the catch cavity 1360 of the respective diverter plug 1308 that has been moved to the 'Seed Diverting' position. Subsequently, due to gravity, vacuum and/or forced air, each seed will travel though the respective sorting channel 1304 and second transfer tube 1416 into the particular identified seed repository 1024.

Thus, in operation, the multi-spectral image data for each seed in the set of seeds is analyzed to identify one or more particular phenotypes of each individual seed in the set. The trap door bottoms 1200 are then moved from the 'Seed Imaging' position to the 'Seed Off-load' position such that each seed in the set of seeds substantially slides off the respective trap door bottom 1200 and into the mouth 1236 of the respective corresponding imaged seed sorter 1020, where the seeds are cued, via the respective cueing plugs 1306. Then, based on the identified one or more particular phenotypes of each individual seed, the master controller system 1028 moves a selected one of the diverting plugs 1308 of each corresponding imaged seed sorter 1020 to the 'Seed Diverting' position. The cueing plugs 1306 are then moved to the "Access' position and each seed slides along the bottom 1380 of the respective imaged seed sorter mouth 1236 and onto the respective imaged seed sorter angled sorting ramp 1344. Each seed will then slide along the respective imaged seed sorter angled sorting ramp 1344 and into the catch cavity 1360 of the respective diverter plug 1308 that has been moved to the 'Seed Diverting' position. Subsequently, due to gravity, vacuum and/or forced air, each seed will travel though the respective sorting channel 1304 and second transfer tube into the particular identified seed repository 1024.

Once a set of seeds are imaged and sorted, a new set of seeds are loaded onto the imaging stage assembly and the imaging, analyzing and sorting process is repeated. In various embodiments, the seed sorting system 10 can singulate, load, image, analyze and sort a set of seeds approximately every three to five seconds or faster.

It should be understood that each respective seed is sorted to a particular one of the seed repositories 1024 based on the one or more identified phenotypes of each respective individual seed. Therefore, all within a set of seeds having substantially the same one or more identified phenotypes will be sorted to the same seed repository 1024, while all seeds within a set identified to be absent the one or more other phenotypes will be sorted to a different selected seed repository 1024. Similarly, all seeds within a set that are determined to be too small, e.g., seed fragments, will be sorted to still another selected seed repository 1024, while all seeds within a set that are determined to be too large, e.g., double seeds, will be sorted to still another selected seed repository 1024. Still further, in various embodiments, if after a seed has been imaged and analyzed, it is inconclusive whether the seed possesses or does not possess a particular phenotype, the respective seed can be sorted to yet another selected seed repository 1024. Thus, each seed repository 1024 is designated to receive only a single type of seeds, i.e., only seeds possessing the desired phenotype, only seeds lacking the desired phenotype, only seeds where it is uncertain whether they possess the desired phenotype, only seeds that fail to meet a minimum size criteria, and only seeds that exceed a maximum size criteria.

As set forth above, in various embodiments, the master controller system 1028 can execute various algorithms to perform multi-variate analysis on the multi-spectral image data collected via the imaging theater 1012 and imaging device(s) 1016, to identify particular phenotype(s) of each seed. The master controller system 1028 can then control the operation of the OL&S subsystem 13 to selectively sort the seeds into the seed repositories 1024, based on the identified phenotype(s). For example, in various embodiments, the seeds may comprise corn seeds for doubled haploid breeding wherein diploid seeds have a blue anthocyanin marker in the germ area. In such embodiments, the master controller system 1028 can perform multi-variate analysis on the collected multi-spectral image data to identify whether each seed possesses the blue anthocyanin marker. The master controller system 1028 can then sort the seeds possessing the marker to a particular seed repository 1024, sort the seeds not possessing the marker to a different seed repository 1024, sort seeds where it is undetermined whether they possess the maker to yet another seed repository 1024 and sort the seed that do not meet or exceed a size threshold to still another seed repository.

Figure 18:
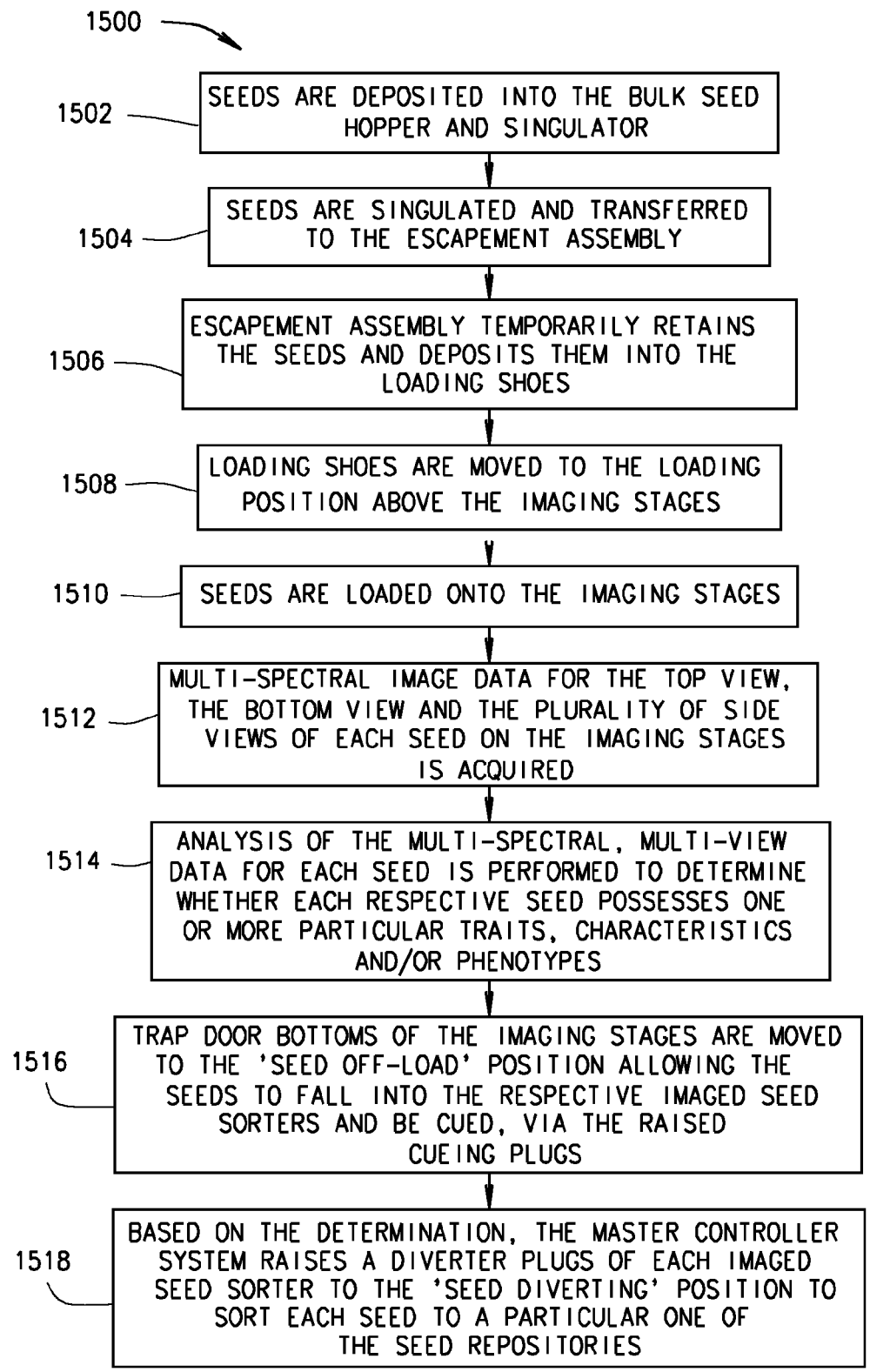
FIG. 18 is an exemplary flow chart illustrating the general operation of the seed sorter system shown in FIG. 13A, in accordance with the various embodiments of the present disclosure.

FIG. 18 illustrates a flow chart 1500 of the general operation of the seed sorter system 10, in accordance with the various embodiments illustrated in FIGS. 1 and 13A through 17C. Initially, a plurality of seeds are deposited into the seed hopper 1056 of the bulk seed hopper and singulator 1004, as indicated at 1502. The seeds are then singulated, via the singulation wheel 1060, and transferred to the escapement assembly 1052, via the tube shuttle 1044 and first transfer tubes 1048, as indicated at 1504. The escapement assembly 1052 temporarily retains the seeds and then deposits each seed into the catch funnel 1120 of a respective one of the loading shoes 1108, as indicated at 1506. Subsequently, the top aperture cover 1132 of each loading shoe 1108 is moved to the 'Closed' position to retain the seeds within the respective catch funnels 1120, and the loading shoes 1108 are moved to the 'Seed Loading' position above the imaging stages 1148, as indicated at 1508. The bottom aperture cover 1136 of each loading shoe 1108 is then moved to the 'Open' position to deposit each seed onto a respective one of the imaging stages 1148, as indicated at 1510.

Once the seeds are loaded onto the imaging stages 1148, operation of the upper and lower light ring assemblies 1152 and 1160 is synchronized with the operation of the imaging devices 1016 to collect the multi-spectral image data of each seed and transmit the image data to the master controller system 1028, as indicated at 1512. More specifically, multi-spectral image data is acquired for the top view of each seed, the bottom view of each seed reflected from the bottom mirror assemblies 1164 and the plurality of side views of each seed reflected from each of the respective annular mirror fixture imaging mirrors 1212.

In various embodiments, the multi-spectral image data comprises images of the top, bottom and sides of each seed acquired at eight different spectral wavelengths, e.g., approximately 400 nm, 450 nm, 500 nm, 550 nm, 600 nm, 650 nm, 700 nm and 750 nm, via eight band pass filters of the optic filter device 1192. The multi-spectral, multi-view data for each seed is then analyzed by the master controller system 1028 to determine whether each respective seed possesses one or more particular phenotypes, such as a blue anthocyanin marker in the germ area of each seed indicating whether each respective seed is a diploid, as indicated a 1514. In various embodiments, multi-variate analysis can be employed by the master controller system 1028 to analyze the collected multi-spectral image data.

The trap door bottoms 1200 of the imaging stages 1148 are then moved to the 'Seed Off-load' position to allow each seed to fall into the mouth 1236 of each respective imaged seed sorter 1020 and be cued, via each respective raised cueing plug 1306, as indicated at 1518. While the seeds are cued, based on the determination whether each respective seed possesses the one or more particular phenotypes, the master controller system 1028 raises a particular one of the diverter plugs 1308 of each imaged seed sorter 1020 to the 'Seed Diverting' position and lowers the cueing plugs 1306 to the 'Access' position. Accordingly, each seed is diverted through the respective sorting channel 1304 and into the corresponding seed repository 1024, as indicated at 1516.

Referring now to FIGS. 19, 20A, 20B and 20C, FIG. 19 provides a flow chart 1600 illustrating an exemplary analysis process executed by the master controller system 1028 on the multi-spectral image data collected by the I&S subsystem 12 and master controller system 1028. In various embodiments, the master controller system 1028 parses the image data collected for each seed into 'top view' data (i.e., data acquired by each imaging device 1016 directly from the top portion of each respective seed and imaging stage 1148), 'bottom view' data (i.e., data acquired by each imaging device 1016 that is reflected from the respective bottom mirror assemblies 1164), and a plurality of 'side view' data sets (i.e., a plurality of set of data acquired by each imaging device 1016, wherein each set relates to image data reflected from a particular one of the image mirrors 1212). In various embodiments, to analyze the multi-spectral image data collected via the I&A subsystem 12, the master controller system 1028 analyzes the 'top view' data first. In doing so, the master controller system 1028 first develops a background mask, and applies the background mask to the image data of each of the 'top view' images acquired at each of the various spectral wavelengths to remove approximately all the data points, e.g., pixels, that are considered to be background data, i.e., non-seed related data, as indicated at 1602. An exemplary pictorial illustration of a 'top view' image after the background mask has been applied as shown in FIG. 20A. In various embodiments, the background mask can be constructed using any one of the various spectral wavelength images, e.g., the image with the best signal-to-noise ratio, to mathematically determine which data points represent background data.

After the background mask has been applied, the master controller system 1028 applies a first size threshold mask to each of the images to filter out any data remaining in each image that is too small to be a seed or a whole, in-tact seed, as indicated at 1604. An exemplary pictorial illustration of a 'top view' image after the background and first size threshold masks have been applied is shown in FIG. 20B. For example, noise along the edges or in the corners of each image may remain after the background mask is applied or parts of broken seeds can be present, or image data of the respective imaging stage 1148 may remain. Such extraneous data is removed by the first size threshold mask. In various embodiments, the first size threshold mask is predetermined based on known size parameters of the type of seeds being analyzed and sorted by the seed sorter system 10.

After the first size threshold mask is applied, the master controller system 1028 applies a fill and erosion mask to each of the images, as indicated at 1606. The fill and erosion mask mathematically determines if the remaining image data of seed includes any 'dark' spots within each seed image. Such 'dark' spots can be present due to color contrast of each respective seed or shadows caused by the contour of each respective seed. The fill and erosion mask 'fills in' such dark spots and also fills or removes pixels around the edges of each seed image caused by such things as noise and/or background 'bleed-through'. Thus, the fill and erosion mask 'fills in' dark spots within each seed image and 'cleans up' the edges of each seed image. An exemplary pictorial illustration of a 'top view' image after the background mask, the first size threshold mask and the fill and erosion mask has been applied is shown in FIG. 20C.

The erosion and fill mask can sometimes remove, or filter out, pixels such that the resulting image of a seed includes a large object and a much smaller object at the border of the seed. Therefore, the master controller system 1028 applies a second size threshold mask to remove the smaller objects, as indicated at 1608. In various embodiments, the second size threshold mask is predetermined based on known size parameters of the type of seeds being analyzed and sorted by the seed sorter system 10.

Thus, the background, first and second size threshold, and fill and erosion masks remove all data points, i.e., pixels, not related to one of the seeds in the respective imaging stages 1148 for the 'top view' image data of each of the 'top view' images acquired at each of the various spectral wavelengths. The master controller system 1028 then performs mathematical analysis on the various 'top view' images to determine whether the remaining image data for each individual seed includes data indicative of a desired phenotype, as indicated at 1610. The master controller system 1028 can employ any mathematical analysis technique or process suitable to make such a determination. For example, in various embodiments, the master controller system 1028 employs multivariate analysis to determine whether the remaining multi-spectral image data for each individual seed includes data indicative of an anthocyainin marker in the germ of the seed.

More particularly, multivariate analysis is performed for each seed on each data point, or pixel, of the multi-spectral image data remaining after application of the first and second size threshold, and the fill and erosion masks to obtain a resultant value that is compared to a predetermined first threshold value. Whether the resultant value is above or below the first threshold is indicative of the desired phenotype, e.g., whether the pixel is indicative of an anthocyainin marker in the germ of the seed. The resultant values above the first threshold and/or below the first threshold are compiled to obtain a total number of resultant values above the first threshold and/or a total number of resultant values below the first threshold for the first set of multi-spectral images.

After the 'top view' image data has been analyzes, as described above, the master controller system 1028 sequentially analyzes the 'bottom view' image data and the plurality of 'side view' sets of image data in the same manner as described above with regard to analysis of the multi-spectral 'top view' image data. Thus, analysis of the 'top view', the 'bottom view' image data and the plurality of 'side view' sets of image data provides a plurality of sets of resultant values, e.g., ten sets resultant values, above the first threshold and/or a plurality of sets of resultant values, e.g., ten sets resultant values, below the first threshold.

Once the master controller system 1028 has analyzed the plurality of sets of multi-spectral image data and generated the respective sets of resultant values, the master controller system 1028 sums the sets of resultant values and compares the sum to a predetermined second threshold value. More specifically, the master controller system 1028 combines the sets of resultant values above the first threshold and/or combines the sets of resultant values below the first threshold to obtain an aggregate sum of resultant values above the first threshold and/or an aggregate sum of resultant values below the first threshold. The aggregate sum of resultant values above the first threshold and/or the aggregate sum of resultant values below the first threshold are then compared to the second threshold in order to identify whether each respective seed possess the desired phenotype, e.g., the blue anthocyanin marker.

For example, if the aggregate sum of the resultant values is above the second threshold, the seed is identified as a diploid. But, if the aggregate sum of the resultant values is below the second threshold, the seed is identified as a haploid, and if the aggregate sum of the resultant values is equal to the second threshold, the seed is identifies as an unknown.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. A method for determining whether a seed exhibits a desired phenotype, said method comprising:
   directing light onto a seed from at least two directional angles and at a plurality of sequentially changing spectral wavelengths;
   collecting image data from at least three portions of the seed selected from a top portion, a bottom portion and at least one side portion of the seed, at each of the spectral wavelengths; and
   analyzing the collected image data to determine whether the seed exhibits a desired phenotype.

2. The method of claim 1, wherein analyzing the collected image data comprises determining whether the seed includes a fluorescent or visual marker.

3. The method of claim 1, wherein analyzing the collected image data comprises determining whether the seed includes an anthocyanin marker in the germ of the respective seed.

4. The method of claim 1, wherein collecting image data from at least three portions of the seed selected from a top portion, a bottom portion and at least one side portion of the seed, at each of the spectral wavelengths comprises:
   collecting image data from the top portion of the seed at each of the spectral wavelengths utilizing an imaging device; and
   collecting image data from the at least one side portion of the seed at each of the spectral wavelengths utilizing the imaging device.

5. The method of claim 1, wherein analyzing the collected image data comprises performing multi-variate analysis on the collected image data to determine whether the seed exhibits the desired phenotype.

6. The method of claim 1, further comprising selectively depositing the seed into a respective selected one of a plurality of seed repositories based on the determination of whether the seed exhibits the desired phenotype.

7. A system for sorting a plurality of seeds based on identified phenotypes of the seeds, said system comprising an imaging and analysis subsystem structured and operable to collect image data of a top portion of a seed, a bottom portion of the seed, and at least one side portion of the seed, and to analyze the collected image data to determine whether the seed exhibits a desired phenotype, the imaging and analysis subsystem having an imaging device configured to collect the image data of at least two of said portions of the seed selected from the top portion of the seed, the bottom portion of the seed, and the at least one side portion of the seed.

8. The system of claim 7, further comprising a load and transport subsystem including a bulk seed hopper and singulator connected to an escapement assembly via a plurality of seed transfer tubes, wherein:
   the bulk seed hopper and singulator is structured and operable to singulate the seed from a plurality of seeds in a seed hopper and deposit the seed into a respective one of a plurality of chambers of the escapement assembly; and the escapement assembly is structured and operable to temporarily retain the seed within the respective escapement assembly chamber.

9. The system of claim 8, wherein the load and transport subsystem further comprises one or more on-loaders, each on-loader including a plurality of seed loading shoes that each include a seed catch funnel, wherein:

the escapement assembly is structured and operable to deposit the respective seed into a respective corresponding one of the loading shoe seed catch funnels when the loading shoes are in a 'Home' position; and each on-loader is structured and operable to selectively move the seed loading shoes between the 'Home' position and a 'Loading' position for transferring the seed to the imaging and analysis subsystem.

10. The system of claim 9, wherein each loading shoe includes a damping ring attached to each respective loading shoe at the bottom of each respective catch funnel, each damping ring structured to stabilize a seed substantially at a center of a transparent window of a trap door bottom of a respective one of a plurality of mirrored imaging stages of the imaging and analysis subsystem upon transferring the seed to the imaging and analysis subsystem.

11. The system of claim 7, wherein the imaging and analysis subsystem includes an imaging theater, wherein the imaging theater includes:

a plurality of mirrored imaging stages, each mirrored imaging stage structured to receive a seed from a respective one of a plurality of seed loading shoes, thereby loading each mirrored imaging stage with a seed; and a plurality of upper ring lights positioned above the mirrored imaging stages and a plurality of lower ring lights positioned below the mirrored imaging stages, the upper and lower ring lights structured and operable to substantially simultaneously direct light, at a plurality of sequentially changing spectral wavelengths, on a top portion and a bottom portion of each loaded mirrored imaging stage.

12. The system of claim 11, wherein each upper ring light comprises an upper fiber optic light ring, each lower ring light comprises a lower fiber optic light ring, and the imaging and analysis subsystem further includes a controllable light source operatively coupled with an optic filter device connected to each of the upper and lower ring lights via fiber optic cables, wherein the controllable light source and optic filter device are operable to:

transmit light through the fiber optic cables to each of the upper and lower fiber optic light rings to substantially simultaneously direct light at the top and bottom portions of each loaded mirrored imaging stage; and sequentially change the spectral wavelength of the transmitted light to each of a plurality of selected wavelengths to substantially simultaneously direct light at the top and bottom portions of each loaded mirrored imaging stage at each of the selected spectral wavelengths.

13. The system of claim 11, wherein each mirrored imaging stage comprises:

an annular mirror fixture having a plurality of angled image mirrors mounted around an interior wall of each respective annular mirror fixture; and a trap-door bottom including a transparent window on which a seed is located during image data collection, the trap-door bottom movable between a 'Seed Imaging' position for collecting the image data and a 'Seed Off-Load' position for transferring the imaged seed to a seed loading, transporting and sorting station.

14. The system of claim 13, wherein the imaging theater further includes one or more bottom mirror assemblies positioned below the mirrored imaging stages, each bottom mirror assembly including a plurality of bottom mirrors mounted at an angle to posts of the respective bottom mirror assembly.

15. The system of claim 14, wherein the imaging device is structured and operable to:

collect the image data of the top portion of the seed, at each of the spectral wavelengths;

collect the image data of the at least one side portion of the seed, at each of the spectral wavelengths, reflected from the plurality of angled image mirrors mounted to the annular mirror fixture; and collect the image data of the bottom portion of the seed, at each of the spectral wavelengths, reflected from the plurality of angled bottom mirrors of each respective bottom mirror assembly.

16. The system of claim 15, further comprising a master controller system structured and operable to perform multivariate analysis on the collected image data to determine whether the seed exhibits the desired phenotype.

17. The system of claim 7, further comprising an off-loading and sorting subsystem that includes a plurality of seed repositories and a plurality of imaged seed sorters, each imaged seed sorter structured and operable to:

receive a seed from a respective corresponding one of a plurality of imaging stages of the imaging and analysis subsystem; and selectively divert the seed into a respective selected one of the seed repositories based on a determination made by the imaging and analysis subsystem whether the seed exhibits the desired phenotype.

18. The system of claim 17, wherein each imaged seed sorter comprises:

a housing;

a plurality of sorting channels enclosed within the housing, each sorting channel terminating at a respective one of a plurality of collared exit ports, each collared exit port having a respective one of a plurality of transfer tubes connected thereto, each transfer tube terminating at a respective one of the seed repositories; and a plurality of diverter plugs, each diverter plug slidably mounted within a top portion of a respective sorting channel, and structured and operable to move between a 'Seed By-pass' position and a 'Seed Diverting' position, in which the received seed is diverted into the respective corresponding sorting channel and subsequently into the respective corresponding seed repository.

19. A method for determining whether individual ones of a plurality of seeds exhibit a desired phenotype, said method comprising:

loading a seed onto a mirrored imaging stage having a transparent bottom;

reflecting image data from a mirror for a top portion, a bottom portion, and/or at least one side portion of the seed loaded onto the mirrored imaging stage;

collecting image data for the top portion, the bottom portion and the at least one side portion of the seed, including the reflected image data;

analyzing the collected image data to determine whether each seed exhibits a desired phenotype.

20. The method of claim 19, wherein analyzing the collected image data comprises determining whether the seed includes a fluorescent or visual marker.

21. The method of claim 19, wherein analyzing the collected image data comprises determining whether the seed includes an anthocyainin marker in the germ of the seed.

22. The method of claim 19, wherein loading a seed onto a mirrored imaging stage comprises:
singulating the seed from a plurality of seeds in a bulk seed hopper;
depositing the seed into a chamber of an escapement assembly; and
temporarily retaining the seed within the escapement assembly chamber.

23. The method of claim 22, wherein loading a seed onto a mirrored imaging stage further comprises:
transferring the seed from the escapement assembly chamber into a seed loading shoe positioned at a 'Home' position directly beneath the escapement assembly;
translating the loading shoe from the 'Home' position to a 'Loading' position directly above the mirrored imaging stage; and
transferring the seed from the loading shoe onto the mirrored imaging stage.

24. The method of claim 23, wherein transferring the seed from the loading shoe onto the mirrored imaging stage comprises:
transferring the seed through a seed catch funnel extending through the loading shoe; and
stabilizing the seed substantially at a center of a transparent window of a trap door bottom of the mirrored imaging stage utilizing a damping ring attached to the loading shoe at a bottom end of the catch funnel.

25. The method of claim 19, further comprising directing light at a plurality of sequentially changing spectral wavelengths on a top portion and a bottom portion of the loaded mirrored imaging stage.

26. The method of claim 25, wherein directing light at a plurality of sequentially changing spectral wavelengths on a top portion and a bottom portion of the loaded mirrored imaging stage comprises:
transmitting light through fiber optic cables from a controllable light source to an upper fiber optic light ring located above the mirrored imaging stage and a lower fiber optic light ring located below the mirrored imaging stage; and
sequentially changing the spectral wavelength of the transmitted light to each of the plurality of selected wavelengths.

27. The method of claim 19, wherein collecting image data for the top portion, the bottom portion and the at least one side portion of the seed comprises:
collecting image data for the top portion of the seed utilizing an imaging device positioned above the mirrored imaging stage; and
collecting image data for the at least one side portion of the seed utilizing a plurality of image mirrors mounted at an angle within an annular mirror fixture of the mirrored imaging stage such that the image data for the at least one side portion is reflected from a respective one of the image mirrors to the imaging device positioned above the mirrored imaging stage.

28. The method of claim 27, wherein collecting image data for the top portion, the bottom portion and the at least one side portion of the seed further comprises collecting image data from the bottom portion of the seed utilizing one or more bottom mirror assemblies positioned below the mirrored imaging stage such that the image data for the bottom portion of the seed is reflected from a plurality of bottom mirrors mounted at an angle within the one or more bottom mirror assemblies to the one or more imaging devices positioned above the mirrored imaging stage.

29. The method of claim 19, wherein analyzing the collected image data comprises performing multi-variate analysis on the collected image data to determine whether the seed exhibits the desired phenotype.

30. The method of claim 19, further comprising selectively depositing the seed into a respective selected one of a plurality of seed repositories, which includes:
moving a trap door bottom of the mirrored imaging stage from a 'Seed Imaging' position, in which the image data is collected, to a 'Seed Off-load' position, whereby the seed is allowed to slide off the trap door bottom into a mouth of an imaged seed sorter; and
selectively operating a diverter plug of the imaged seed sorter to selectively divert the seed to the respective selected seed repository.

31. The method of claim 1, wherein collecting image data includes collecting image data from the top portion of the seed, the bottom portion of the seed, and the at least one side portion of the seed, at each of the spectral wavelengths, using an imaging device.

32. The method of claim 31, wherein collecting image data includes substantially simultaneously collecting image data from the top portion of the seed, the bottom portion of the seed, and the at least one side portion of the seed using the imaging device.

33. The system of claim 7, further comprising:
a load and transport subsystem structured and operable to singulate the seed from a plurality of seeds and transport the seed to the imaging and analysis system; and
an off-loading and sorting subsystem structured and operable to sort the seed to a repository based on whether the seed exhibits the desired phenotype.

34. The system of claim 33, further comprising a transparent imaging surface for supporting the seed in the imaging and analysis subsystem to allow for collecting image data of the top portion, the bottom portion, and the at least one side portion of the seed.

35. The system of claim 34, wherein the transparent imaging surface includes a multi-well seed tray.

36. The system of claim 34, wherein the transparent imaging surface includes an imaging stage.

37. The system of claim 7, wherein the imaging device of the imaging and analysis subsystem is structured and operable to substantially simultaneously collect image data of the top portion, the bottom portion, and the at least one side portion of the seed.

38. The method of claim 19, further comprising:
substantially simultaneously directing light at a plurality of sequentially changing spectral wavelengths on a top portion and a bottom portion of the loaded mirrored imaging stage; and
substantially simultaneously collecting image data for the top portion, the bottom portion, and the at least one side portion of the seed, at each of the spectral wavelengths.

* * * * *